(12) United States Patent
Velasquez et al.

(10) Patent No.: US 11,806,419 B2
(45) Date of Patent: Nov. 7, 2023

(54) APTAMERS FOR ODOR CONTROL APPLICATIONS

(71) Applicant: The Procter & Gamble Company, Cincinnati, OH (US)

(72) Inventors: Juan Esteban Velasquez, Cincinnati, OH (US); Amy Violet Trejo, Mason, OH (US); Gregory Allen Penner, Toronto (CA); Stevan David Jones, Hyde Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 624 days.

(21) Appl. No.: 16/850,840

(22) Filed: Apr. 16, 2020

(65) Prior Publication Data

US 2020/0330353 A1    Oct. 22, 2020

Related U.S. Application Data

(60) Provisional application No. 62/834,425, filed on Apr. 16, 2019.

(51) Int. Cl.
*A61K 8/60* (2006.01)
*A61K 8/34* (2006.01)
*A61Q 15/00* (2006.01)

(52) U.S. Cl.
CPC .............. *A61K 8/606* (2013.01); *A61K 8/34* (2013.01); *A61Q 15/00* (2013.01)

(58) Field of Classification Search
CPC ...... A61K 8/606; A61Q 15/00; C12N 15/115; C12N 2310/16
USPC ..................... 435/6.1, 91.1, 91.31, 455, 458; 514/44 A; 536/23.1, 24.5
See application file for complete search history.

(56) References Cited

U.S. PATENT DOCUMENTS

| | | |
|---|---|---|
| 2,946,725 A | 7/1960 | Norris |
| 3,070,510 A | 12/1962 | Cooley |
| 3,429,963 A | 2/1969 | Shedlovsky |
| 3,506,720 A | 4/1970 | Model et al. |
| 3,535,421 A | 10/1970 | Briner |
| 3,538,230 A | 11/1970 | Pader |
| 3,678,154 A | 7/1972 | Widder |
| 3,689,637 A | 9/1972 | Pader |
| 3,696,191 A | 10/1972 | Weeks |
| 3,711,604 A | 1/1973 | Colodney et al. |
| 3,737,533 A | 6/1973 | Moon et al. |
| 3,862,307 A | 1/1975 | Di |
| 3,911,104 A | 10/1975 | Harrison |
| 3,935,306 A | 1/1976 | Roberts et al. |
| 3,959,458 A | 5/1976 | Agricola |
| 3,988,443 A | 10/1976 | Ploger et al. |
| 3,991,177 A | 11/1976 | Vidra et al. |
| 4,040,858 A | 8/1977 | Wason |
| 4,051,234 A | 9/1977 | Gieske |
| 4,058,595 A | 11/1977 | Colodney |
| 4,138,477 A | 2/1979 | Gaffar |
| 4,154,815 A | 5/1979 | Pader |
| 4,183,914 A | 1/1980 | Gaffar |
| 4,304,766 A | 12/1981 | Chang |
| 4,355,022 A | 10/1982 | Rabussay |
| 4,590,066 A | 5/1986 | Parran, Jr. et al. |
| 4,627,977 A | 12/1986 | Gaffar |
| 4,661,341 A | 4/1987 | Benedict et al. |
| 4,846,650 A | 7/1989 | Benedict et al. |
| 4,877,603 A | 10/1989 | Degenhardt |
| 4,980,153 A | 12/1990 | Jackson et al. |
| 4,992,420 A | 2/1991 | Neeser |
| 5,000,939 A | 3/1991 | Dring et al. |
| 5,037,637 A | 8/1991 | Gaffar et al. |
| 5,626,838 A | 5/1997 | Cavanaugh, Jr. |
| 5,827,505 A | 10/1998 | Hughes et al. |
| 5,939,052 A | 8/1999 | White, Jr. et al. |
| 6,251,372 B1 | 6/2001 | Witt et al. |
| 6,707,929 B2 | 3/2004 | Marapane |
| 7,079,158 B2 | 7/2006 | Lambertsen |
| 7,104,800 B2 | 9/2006 | Ortiz-Valero |
| 7,435,794 B2 | 10/2008 | Lukyanov et al. |
| 8,119,162 B2 | 2/2012 | Miksa |
| 8,168,600 B2 | 5/2012 | Dokka |
| 8,241,651 B2 | 8/2012 | Lahann |
| 8,338,115 B2 | 12/2012 | Adler |
| 8,360,973 B2 | 1/2013 | Bazin |
| 8,484,155 B2 | 7/2013 | Yamaguchi |
| 8,871,920 B2 | 10/2014 | Purschke |
| 9,457,071 B2 | 10/2016 | Hide |
| 9,518,265 B2 | 12/2016 | Hohlig |
| 9,709,576 B2 | 7/2017 | Hide |

(Continued)

FOREIGN PATENT DOCUMENTS

| | | |
|---|---|---|
| CN | 104586362 A | 5/2015 |
| CN | 105441213 A | 3/2016 |

(Continued)

OTHER PUBLICATIONS

Gao et al (Anal Bioanal Chem, vol. 408, pp. 4567-4573 (2016)) (Year: 2016)*
"Jack Florek '17 presents at ACS in San Francisco", Emmanuel College, retrieved from http://gerdonlab.blogs.emmanuel.edu/2017/04/04/jack-florek-17-presents-acs-san-francisco/, Oct. 15, 2018, 6 pages.
All Office Actions; U.S. Appl. No. 16/270,911.
Bawazer et al., "Efficient Selection of Biomineralizing DNA Aptamers Using Deep Sequencing and Population Clustering", ACS Nano, vol. 8, No. 1, 2014, pp. 1-10.
Database WPI, XP002785798, Week 201649, 2017, Thomson Scientific, London GB, AN 2016-20069A.
Eifler, Electronic Nose-Based Fusarium Detection and Deoxynivalenol Aptamer Development, Dissertation, Jul. 2014, 106 pages.

(Continued)

*Primary Examiner* — Jane J Zara
(74) *Attorney, Agent, or Firm* — Alexandra S. Anoff

(57) ABSTRACT

Nucleic acid aptamers having a high binding affinity and specificity for malodorous molecules and the use of such aptamers to reduce the intensity of the undesirable smells in personal care compositions.

8 Claims, 15 Drawing Sheets

Specification includes a Sequence Listing.

(56) References Cited

U.S. PATENT DOCUMENTS

| | | |
|---|---|---|
| 9,732,348 B2 | 8/2017 | Cauchard |
| 9,902,961 B2 | 2/2018 | Dausse |
| 9,976,145 B2 | 5/2018 | Jarosch |
| 9,996,674 B2 | 6/2018 | Segman |
| 10,001,496 B2 | 6/2018 | Jung |
| 10,231,531 B2 | 3/2019 | Witchell |
| 10,650,289 B2 | 5/2020 | Szegedy |
| 10,676,396 B2 | 6/2020 | Johannsmann et al. |
| 2002/0065452 A1 | 5/2002 | Bazin |
| 2002/0150287 A1 | 10/2002 | Kobayashi |
| 2002/0183988 A1 | 12/2002 | Skaanning |
| 2003/0014324 A1 | 1/2003 | Donovan |
| 2004/0236592 A1 | 11/2004 | Aleles |
| 2006/0085274 A1 | 4/2006 | Sottery |
| 2006/0149151 A1 | 7/2006 | Ladjevardi |
| 2006/0178904 A1 | 8/2006 | Aghassian |
| 2007/0054261 A1 | 3/2007 | Sherman |
| 2007/0058858 A1 | 3/2007 | Harville |
| 2008/0097814 A1 | 4/2008 | Koustoumbardis |
| 2008/0152600 A1 | 6/2008 | Huang et al. |
| 2010/0106679 A1 | 4/2010 | Yamaguchi |
| 2010/0254581 A1 | 10/2010 | Neeser |
| 2011/0016001 A1 | 1/2011 | Schieffelin |
| 2012/0041282 A1 | 2/2012 | Nichol |
| 2012/0190627 A1 | 7/2012 | Delattre |
| 2012/0320191 A1 | 12/2012 | Meschkat |
| 2013/0323242 A1 | 12/2013 | Everett |
| 2014/0028822 A1 | 1/2014 | Khadavi |
| 2014/0081095 A1 | 3/2014 | Krishnan |
| 2014/0216492 A1 | 8/2014 | Magri |
| 2014/0378810 A1 | 12/2014 | Davis |
| 2015/0045631 A1 | 2/2015 | Ademola |
| 2015/0217465 A1 | 8/2015 | Krenik |
| 2015/0329863 A1 | 11/2015 | Cauchard et al. |
| 2015/0353933 A1 | 12/2015 | Miyakawa et al. |
| 2016/0061602 A1 | 3/2016 | Fessi |
| 2016/0326530 A1 | 11/2016 | Dausse et al. |
| 2017/0004558 A1 | 1/2017 | Abramowitz |
| 2017/0107515 A1 | 4/2017 | Eberly et al. |
| 2017/0270593 A1 | 9/2017 | Sherman |
| 2018/0040052 A1 | 2/2018 | Robinson |
| 2018/0040053 A1 | 2/2018 | Robinson |
| 2018/0116583 A1 | 5/2018 | Cook |
| 2018/0140248 A1 | 5/2018 | Chandra |
| 2018/0223285 A1 | 8/2018 | Hohlig |
| 2018/0225673 A1 | 8/2018 | Dubey |
| 2018/0235535 A1 | 8/2018 | Cook |
| 2018/0247365 A1 | 8/2018 | Cook |
| 2018/0253866 A1 | 9/2018 | Jain |
| 2018/0349979 A1 | 12/2018 | Robinson |
| 2019/0035149 A1 | 1/2019 | Chen |
| 2019/0048348 A1 | 2/2019 | Velasquez |
| 2019/0048349 A1 | 2/2019 | Velasquez et al. |
| 2019/0112593 A1 | 4/2019 | Penner |
| 2019/0209077 A1 | 7/2019 | Charraud |
| 2019/0350514 A1 | 11/2019 | Purwar |
| 2019/0355115 A1 | 11/2019 | Niebauer |
| 2019/0355119 A1 | 11/2019 | Hu |
| 2020/0000697 A1 | 1/2020 | Velasquez et al. |
| 2020/0002703 A1 | 1/2020 | Velasquez |
| 2020/0221995 A1 | 7/2020 | Mathiaszyk et al. |
| 2021/0106696 A1 | 4/2021 | Dalma-weiszhausz et al. |

FOREIGN PATENT DOCUMENTS

| | | |
|---|---|---|
| FR | 3020465 A1 | 10/2015 |
| GB | 490384 A | 8/1938 |
| JP | 3163309 U | 9/2010 |
| KR | 101456942 B1 | 11/2014 |
| RU | 2306921 C1 | 9/2007 |
| WO | 9960167 A1 | 11/1999 |
| WO | 0191602 A2 | 12/2001 |
| WO | 02083737 A1 | 10/2002 |
| WO | 2006055902 A2 | 5/2006 |
| WO | 2010006215 A1 | 1/2010 |
| WO | 2011085727 A1 | 7/2011 |
| WO | 2015140722 A1 | 9/2015 |
| WO | 2016176203 A1 | 11/2016 |
| WO | 2017139417 A1 | 8/2017 |
| WO | 2017207455 A1 | 12/2017 |
| WO | 2018202065 A1 | 11/2018 |

OTHER PUBLICATIONS

Fujii et al.,"Pesticide vapor sensing using an aptamer, nanopore, and agarose gel on a chip", Lab on a Chip, vol. 17, No. 14, 2017, pp. 2421-2425.

Gao et al., "Post-Selex optimization of aptamers", Analytical and Bioanalytical Chemistry, Springer, vol. 408, No. 17, 2016, pp. 4567-4573.

Geron, "Introducing Capsule Networks", O'Reilly, https://www.oreilly.com/content/introducing-capsule-networks/, Feb. 6, 2018, pp. 1-7.

Hasegawa et al., "Methods for Improving Aptamer Binding Affinity", Molecules, vol. 21, No. 4, 2016, pp. 1-15.

Hurot et al., "Bio-Inspired Strategies for Improving the Selectivityand Sensitivity of Artificial Noses: A Review", Sensors, vol. 20, No. 6, 2020, pp. 1-28.

International Search Report and Written Opinion; Application Ser. No. PCT/US2020/028469; dated Jul. 20, 2020, 12 pages.

Janas et al., "The selection of aptamers specific for membrane molecular targets", Cellular & Molecular Biology Letters, vol. 16, No. 1, 2011, pp. 25-39.

John et al., "ANYL 154: DNA aptamers that bind with high affinity to hydroxyapatite", ACS National Meeting & Exposition; 253rd National Meeting of the American-Chemical-Society (ACS) on Advanced Materials, Technologies, Systems, and Processes, American Chemical So, vol. 253, Apr. 2017, page ANYL154.

Komarova et al., "Selection, Characterization, and Application ofssDNA Aptamer against Furaneol", Molecules, vol. 23, No. 12, 2018, pp. 1-15.

Kuznetsov et al., "Aptamer based vanillin sensor using an ion-sensitive field-effect transistor", Microchimica Acta, vol. 185, No. 1, 2017, 26 pages.

Li et al., "VEGF induces proliferation of human hair follicle dermal papilla cells through VEGFR-2-mediated activation of ERK", Experimental Cell Research, vol. 318, No. 14, 2012, pp. 1633-1640.

Low et al., "DNA aptamers bind specifically and selectively to (1-3)-beta-d-glucans", Biochemical and Biophysical Research Communications, vol. 378, No. 4, 2009, pp. 701-705.

Nonaka et al., "Screening and improvement of an anti-VEGF DNA aptamer", Molecules, vol. 15, No. 1, 2010, pp. 215-225.

Pillaiyar et al., "Downregulation of melanogenesis: drug discovery and therapeutic options", Drug Discovery Today, vol. 22, No. 2, Feb. 2017, pp. 282-298.

Ramos et al., "Female Pattern Hair Loss: A Clinical and Pathophysiological Review", ABD: Anais Brasileiros De Dermatologia, vol. 90, No. 4, Jul.-Aug. 2015, pp. 1-29.

Schwartz et al., "The role of oxidative damage in poor scalp health: ramifications to causality and associated hair growth", International Journal of Cosmetic Science, vol. 37, No. Suppl. 2, 2015, pp. 9-15.

Shibata et al., "The cell wall galactomannan antigen from Malassezia furfur and Malassezia pachydermatis contains -1,6-linked linear galactofuranosyl residues and its detection has diagnostic potential", Microbiology, vol. 155, No. 10, 2009, pp. 3420-3429.

Tang et al., "Improved detection of deeply invasive candidiasis with DNA aptamers specific binding to (1-3)-[beta]-D-glucans from Candida albicans", European Journal of Clinical Microbiology & Infectious diseases, vol. 35, No. 4, 2016, pp. 587-595.

Unpublished U.S. Appl. No. 16/953,385, filed on Nov. 20, 2020, to Supriya Punyani et al.

Velegraki et al., "Malassezia Infections in Humans and Animals: Pathophysiology, Detection and Treatment", PLOS Pathogens, vol. 11, No. 1, Jan. 2015, pp. 1-6.

\* cited by examiner

Sense Primer | Random sequence | Antisense primer

```
              (1)  1         10        20        30        40
Mal-1-87  (1)  ATGGAGATCTAGTAGCGCGGAACGATAAAACGGATCACGA
Mal-3-4   (1)  ATGGAGATCTAGTAGCGCGGAACGACAAAACGGATCACGA (1)  1         10        20        30        40
Mal-2-30  (1)  CTTAAATTTACAAAAAACGAACCAGCGATCGAAGATAGAG
Mal-2-95  (1)  CTTAAATTTACAAAAAACGAACCAGCGATCGAAGATAGAG
Mal-3-65  (1)  CTTAAATTTACAAAAAACGAACCAGCGATCGAAGATAGAG (1)  1         10        20        30        40
Mal-3-1   (1)  GAACGGAATCGACACATTCACGACGAAGAGAATAGAGGCA
Mal-4-44  (1)  GAACGGAATCGACACATTCACGACGAAGAGAATAGAGGCA
Mal-3-8   (1)  GAACGGAATCGACACATTCACGACGAAGAGAATAGAGGCA
```

Figure 5

```
              (1)  1         10        20        30        44
Mal-4-63  (1)  --ACACGTGGTTAGGAGAAGGAGACTCGATT-ATTCAT-TTCCA
Mal-4-85  (1)  CGACACGTCGTGAAG-GAAAGA---TCGATTTATTCATGTTCCT
```

Figure 6

```
              (1)  1         10        20        30        45
Mal-1-59  (1)  -----AGCTGAGGATTGAGAACTGAATCCGAGCGCGGATATCAAA
Mal-3-96  (1)  GTAATAACTG-GGTTTGAGACGTGGAA---AGCGCGG-TATCAAA (1)
Mal-3-45  (1)  ACCTTGTCTATTCA-TGATCAAAATAAAAA--AT-GCGAAGCGA-
Mal-4-17  (1)  ACCTTGTCTATTCA-TGATCAAAATAAAAA--AT-GCGAAGCGA-
Mal-4-2   (1)  -----GTCTGTTCAATCCACAAGAGAAACAGGATCGCGAAGCCAG
```

Figure 7

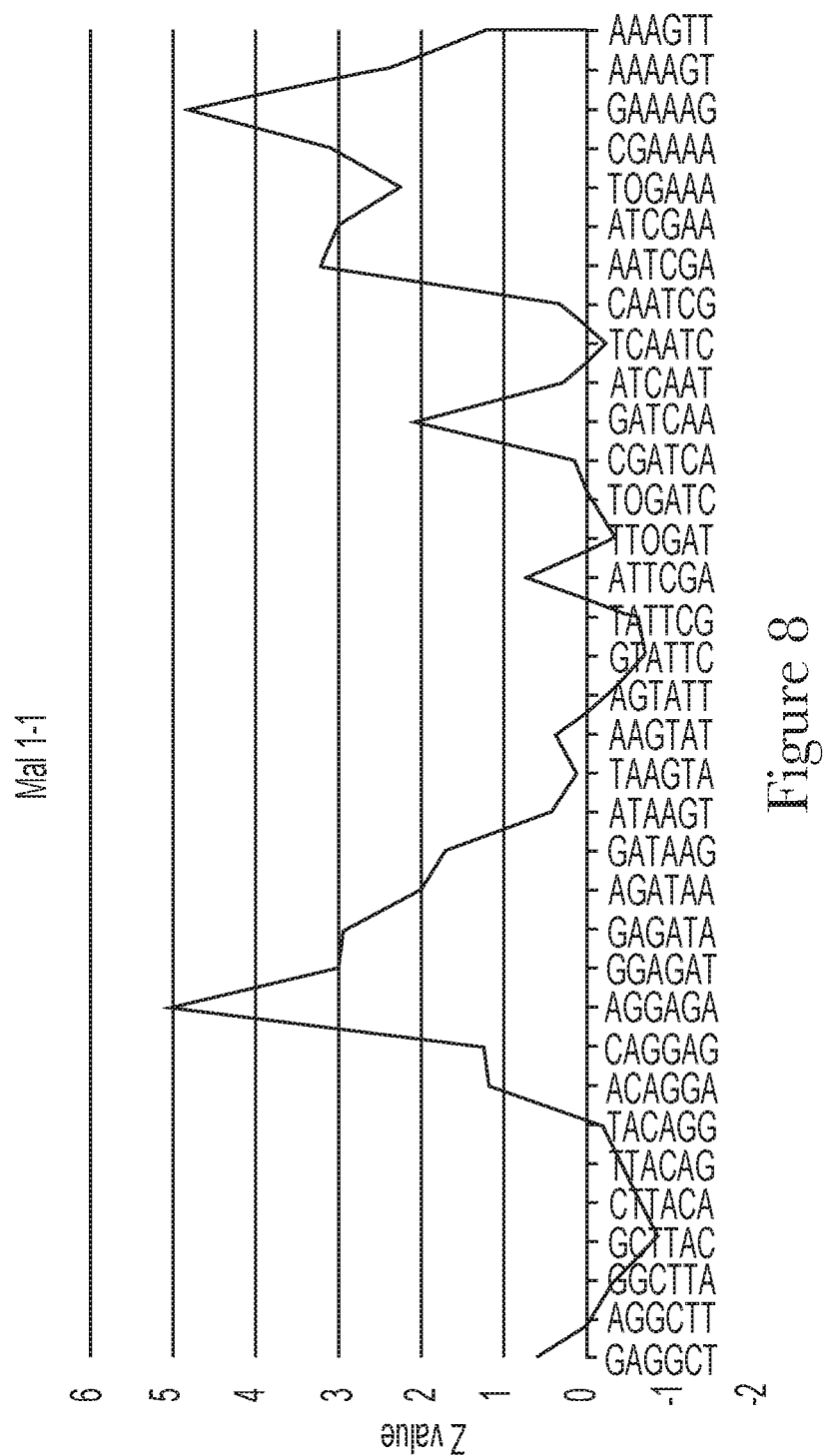

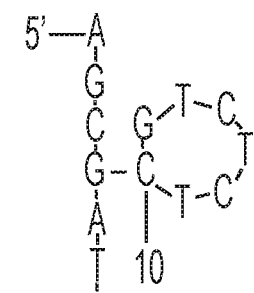
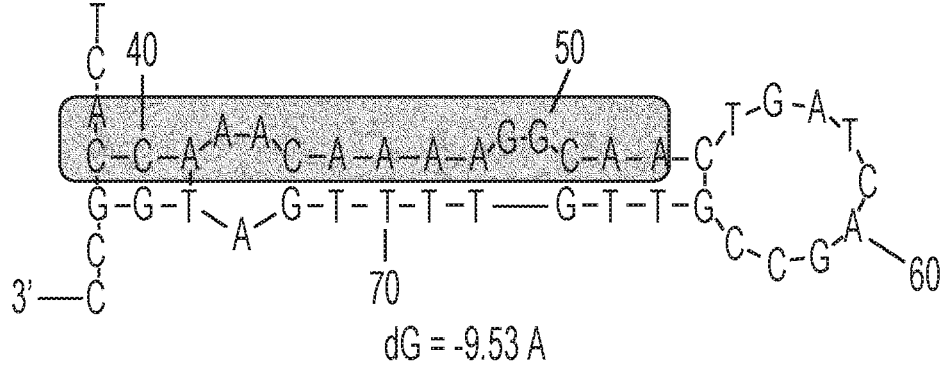
Figure 11

APTAMERS FOR ODOR CONTROL APPLICATIONS

FIELD OF THE INVENTION

The present invention generally relates to nucleic acid aptamers that have a high binding affinity and specificity for malodorous molecules. This invention also relates to the use of such aptamers to reduce the intensity of the undesirable smells in personal care compositions.

BACKGROUND OF THE INVENTION

Aptamers are short single-stranded oligonucleotides, with a specific and complex three-dimensional shape, that bind to target molecules. The molecular recognition of aptamers is based on structure compatibility and intermolecular interactions, including electrostatic forces, van der Waals interactions, hydrogen bonding, and $\pi$-$\pi$ stacking interactions of aromatic rings with the target material. The targets of aptamers include, but are not limited to, peptides, proteins, nucleotides, amino acids, antibiotics, low molecular weight organic or inorganic compounds, and even whole cells. The dissociation constant of the complexes of aptamers and the corresponding target materials typically varies between micromolar and picomolar levels, which is comparable to the affinity of antibodies to their antigens. Aptamers can also be designed to have high specificity, enabling the discrimination of target molecules from closely related derivatives.

Aptamers are usually designed in vitro from large libraries of random nucleic acids by Systematic Evolution of Ligands by Exponential Enrichment (SELEX). The SELEX method was first introduced in 1990 when single stranded RNAs were selected against low molecular weight dyes (Ellington, A. D., Szostak, J. W., 1990. Nature 346: 818-822). A few years later, single stranded DNA aptamers and aptamers containing chemically modified nucleotides were also described (Ellington, A. D., Szostak, J. W., 1992. Nature 355: 850-852; Green, L. S., et al., 1995. Chem. Biol. 2: 683-695). Since then, aptamers for hundreds of microscopic targets, such as cations, small molecules, proteins, cells, or tissues have been selected. A compilation of examples from the literature is included in the database at the website: http://www.aptagen.com/aptamer-index/aptamer-list.aspx. However, a need still exists for aptamers that selectively bind to malodor molecules. These aptamers could be used to reduce the intensity of the undesirable smells in personal care compositions, such as antiperspirants and deodorants.

SUMMARY OF THE INVENTION

In this invention, we have demonstrated the use of FRELEX for the selection of aptamers against different malodor molecular targets and the use of such aptamers to reduce the intensity of the undesirable smells. FRELEX is a method that builds upon the principles of SELEX but does not require immobilization of the target molecules for aptamer selection (WO 2017/035666 A1 and Lecocq Soizic, et al. "Aptamers as biomarkers for neurological disorders. Proof of concept in transgenic mice." 5 Jan. 2018 PLOS ONE, https://doi.org/10.1371/journal.pone.0190212).

In the present invention, an aptamer composition is provided. The aptamer composition comprises at least one oligonucleotide composed of nucleotides selected from the group consisting of: deoxyribonucleotides, ribonucleotides, derivatives of deoxyribonucleotides, derivatives of ribonucleotides, and mixtures thereof; wherein said aptamer composition has a binding affinity for one or more volatile organic compounds selected from the group consisting of: sulfur containing compounds, nitrogen-containing compounds, carboxylic acids, esters, aldehydes, ketones, alcohols, hydrocarbons, and mixtures thereof.

In the present invention, the aptamer composition may have a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof.

In the present invention, the aptamer composition may comprise at least one oligonucleotide selected from the group consisting of SEQ ID NO 1, SEQ ID NO 2, SEQ ID NO 102, SEQ ID NO 103, SEQ ID NO 201, SEQ ID NO 217, SEQ ID NO 301, SEQ ID NO 302, SEQ ID NO 407, SEQ ID NO 408, SEQ ID NO 409, SEQ ID NO 410, SEQ ID NO 411, SEQ ID NO 412, SEQ ID NO 413, and SEQ ID NO 415.

In the present invention, the aptamer composition may comprise at least one oligonucleotide comprising one or more motifs selected from the group consisting of SEQ ID NO 401, SEQ ID NO 402, SEQ ID NO 403, SEQ ID NO 404, SEQ ID NO 405, and SEQ ID NO 406.

In the present invention, a personal care composition is provided. The personal care composition may comprise at least one nucleic acid aptamer; wherein said at least one nucleic acid aptamer has a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof.

BRIEF DESCRIPTION OF THE DRAWINGS

For a more complete understanding of the disclosure, reference should be made to the following detailed description and drawing Figures.

FIG. 5—Alignment of exemplary sequences with at least 90% nucleotide sequence identity that are identified during the selection process.

FIG. 6—Alignment of exemplary sequences with at least 70% nucleotide sequence identity that are identified during the selection process.

FIG. 7—Alignment of exemplary sequences with at least 50% nucleotide sequence identity that are identified during the selection process.

FIG. 8—Motif analysis of random region of aptamer Mal-1-1.

FIG. 11—The predicted secondary structures of aptamer Mal-2-1 and its conserved motif.

DETAILED DESCRIPTION OF THE INVENTION

I. Definitions

Figures 1, 2:
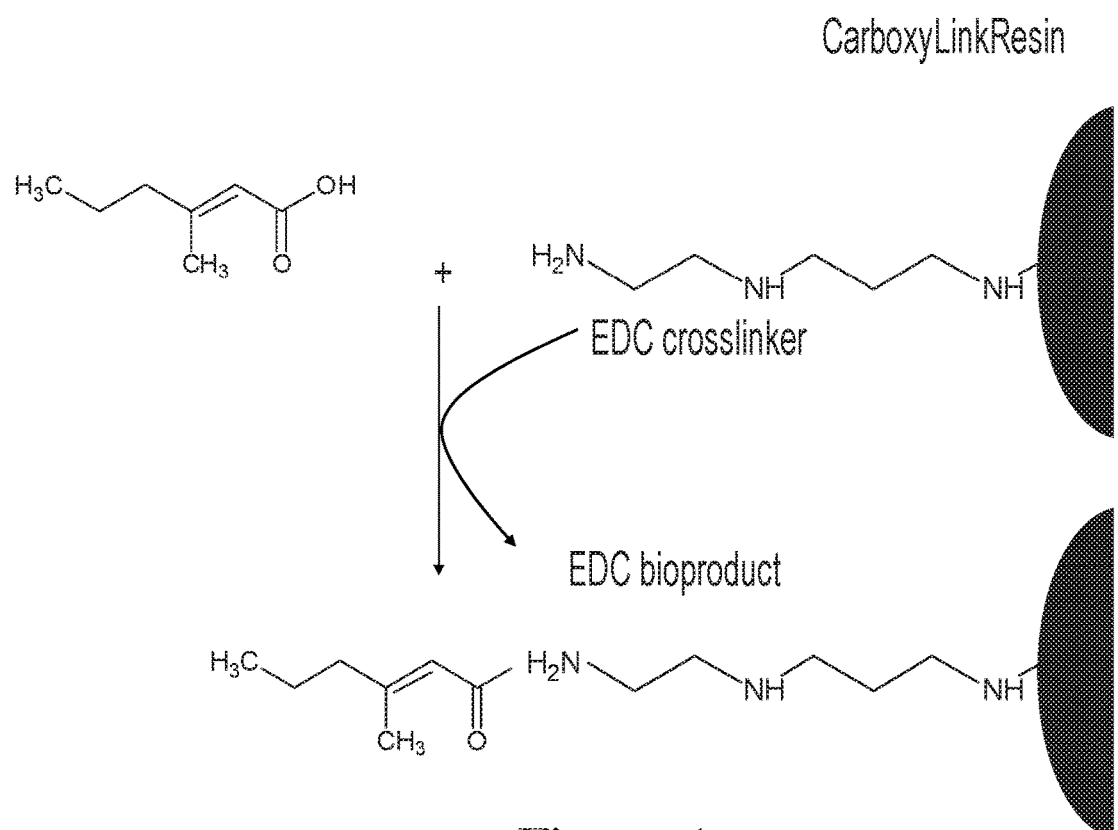
FIG. 1—Schematic of a Traditional Immobilization Strategy of (E)-3-Methyl-2-Hexenoic Acid for SELEX.
FIG. 2—Schematic of the DNA library.

As used herein, the term "aptamer" refers to a single stranded oligonucleotide or a peptide that has a binding affinity for a specific target.

As used herein, the term "nucleic acid" refers to a polymer or oligomer of nucleotides. Nucleic acids are also referred as "ribonucleic acids" when the sugar moiety of the nucleotides is D-ribose and as "deoxyribonucleic acids" when the sugar moiety is 2-deoxy-D-ribose.

As used herein, the term "nucleotide" usually refers to a compound consisting of a nucleoside esterified to a monophosphate, polyphosphate, or phosphate-derivative group via the hydroxyl group of the 5-carbon of the sugar moiety. Nucleotides are also referred as "ribonucleotides" when the sugar moiety is D-ribose and as "deoxyribonucleotides" when the sugar moiety is 2-deoxy-D-ribose.

As used herein, the term "nucleoside" refers to a glycosylamine consisting of a nucleobase, such as a purine or pyrimidine, usually linked to a 5-carbon sugar (e.g. D-ribose or 2-deoxy-D-ribose) via a β-glycosidic linkage. Nucleosides are also referred as "ribonucleosides" when the sugar moiety is D-ribose and as "deoxyribonucleosides" when the sugar moiety is 2-deoxy-D-ribose.

As used herein, the term "nucleobase", refers to a compound containing a nitrogen atom that has the chemical properties of a base. Non-limiting examples of nucleobases are compounds comprising pyridine, purine, or pyrimidine moieties, including, but not limited to adenine, guanine, hypoxanthine, thymine, cytosine, and uracil.

As used herein, the term "oligonucleotide" refers to an oligomer composed of nucleotides.

As used herein, the term "identical" or "sequence identity," in the context of two or more oligonucleotides, nucleic acids, or aptamers, refers to two or more sequences that are the same or have a specified percentage of nucleotides that are the same, when compared and aligned for maximum correspondence, as measured using sequence comparison algorithms or by visual inspection.

As used herein, the term "substantially homologous" or "substantially identical" in the context of two or more oligonucleotides, nucleic acids, or aptamers, generally refers to two or more sequences or subsequences that have at least 40%, 60%, 80%, 90%, 95%, 96%, 97%, 98% or 99% nucleotide identity, when compared and aligned for maximum correspondence, as measured using sequence comparison algorithms or by visual inspection.

As used herein, the term "epitope" refers to the region of a target that interacts with the aptamer. An epitope can be a contiguous stretch within the target or can be represented by multiple points that are physically proximal in a folded form of the target.

As used herein the term "binding affinity" may be calculated using the following equation: Binding Affinity=Amount of aptamer bound to one or more malodor molecule/Total amount of aptamer incubated with the malodor molecule.

As used herein, the term "motif" refers to the sequence of contiguous, or series of contiguous, nucleotides occurring in a library of aptamers with binding affinity towards a specific target and that exhibits a statistically significant higher probability of occurrence than would be expected compared to a library of random oligonucleotides. The motif sequence is frequently the result or driver of the aptamer selection process.

By "consumer product composition", as used herein, it is meant compositions for treating hair (human, dog, and/or cat), including bleaching, coloring, dyeing, conditioning, growing, removing, retarding growth, shampooing, and styling; personal cleansing; color cosmetics; products relating to treating skin (human, dog, and/or cat), including creams, lotions, ointments, and other topically applied products for consumer use; products relating to orally administered materials for enhancing the appearance of hair, skin, and/or nails (human, dog, and/or cat); shaving; body sprays; fine fragrances such as colognes and perfumes; compositions for treating fabrics, hard surfaces and any other surfaces in the area of fabric and home care, including air care, car care, dishwashing, fabric conditioning (including softening), fabric freshening, laundry detergents, laundry and rinse additive and/or care, hard surface cleaning and/or treatment, and other cleaning for consumer or institutional use; products relating to disposable absorbent and/or non-absorbent articles including adult incontinence garments, bibs, diapers, training pants, infant and toddler care wipes; hand soaps; products relating to oral care compositions including toothpastes, tooth gels, mouth rinses, denture adhesives, and tooth whitening; personal health care medications; products relating to grooming including shave care compositions and composition for coating, or incorporation into, razors or other shaving devices; and compositions for coating, or incorporation into, wet or dry bath tissue, facial tissue, disposable handkerchiefs, disposable towels and/or wipes, incontinence pads, panty liners, sanitary napkins, and tampons and tampon applicators; and combinations thereof.

By "oral care composition", as used herein, is meant a product, which in the ordinary course of usage, is not intentionally swallowed for purposes of systemic administration of therapeutic agents, but is rather retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

II. Aptamer Compositions

Nucleic acid aptamers are single-stranded oligonucleotides with specific secondary and tertiary structures that can bind to targets with high affinity and specificity. In the present invention, an aptamer composition may comprise at least one oligonucleotide composed of nucleotides selected from the group consisting of: deoxyribonucleotides, ribonucleotides, derivatives of deoxyribonucleotides, derivatives of ribonucleotides, and mixtures thereof; wherein said aptamer composition has a binding affinity for one or more volatile organic compounds selected from the group consisting of: sulfur containing compounds, nitrogen-containing compounds, carboxylic acids, esters, aldehydes, ketones, alcohols, hydrocarbons, and mixtures thereof.

In another embodiment of the present invention, said one or more volatile organic compounds are selected from the group consisting of: 3-methyl-3-sulfanylhexan-1-ol, 3-sulfanylhexan-1-ol, methanethiol, dimethyl sulfide, dimethyl disulfide, dimethyl trisulfide, hydrogen sulfide, carbon disulfide, 3-methylthio-propanal, dimethyl sulfone; (E)-3-methyl-2-hexenoic acid, 3-methyl-3-hydroxy hexanoic acid, nonanoic acid, octanoic acid, 4-ethyloctanoic acid, heptanoic acid, hexanoic acid, 2-ethylhexanoic acid, pentanoic acid, isovaleric acid, butyric acid, 3-methyl butanoic acid, propanoic acid, acetic acid, formic acid, other 3-methyl carboxylic acids, other carboxylic acids; methyl acetate, ethyl acetate, benzyl acetate, ethyl butanoate, octyl formate, 2-ethylhexyl-salicylate, γ-nonalactone, other esters of carboxylic acids; ammonia, methylamine, ethylamine, trimethylamine, pyrazine, pyridine, 2-methylpyridine, 2-ethylpyridine, 2,3,5-trimethylpyridine, pyrrole, 1-methyl pyrrole, acetonitrile, N,N-dimethylformamide, 1-(2-aminophenyl) ethenone, 4-morpholine ethanamine, 4-cyanocyclohexene, indole, 3-methyl indole, other nitrogen-containing compounds; propanal, 1,2-methyl propanal, butanal, 2-methyl butanal, 3-methyl butanal, pentanal, (E)-2-pentenal, hexanal, (E)-2-hexenal, heptanal, octanal, (E)-2-octenal, nonanal, 2-nonenal, decanal, 2,6-nonadienal, undecanal, dodecanal, tridecanal, benzaldehyde, other aldehydes; diacetyl (2,3-butanedione); 2-methoxyphenol, propanone, butanone, pentan-2-one, pentan-3-one, cyclopentanone, hexan-2-one, cyclohexanone, heptan-2-one, heptan-3-one, oct-1-en-3-one, 2,3-octadione, nonan-2-one, androstenone, 1-phenylethanone, acetophenone, furan, 2-methylfuran, 3-methylfuran, 2,5-diethylfuran, other ketones; ethanol, 2-ethoxyethanol, 2-butoxyethanol, propan-2-ol, 2-methyl-1-propanol, butanol, 3-methyl-1-butanol, pentan-1-ol, pentan-2-ol, hexan-1-ol, oct-1-en-3-ol, 2-butyl-1-octanol, nonan-1-ol, decan-1-ol, cyclodecanol, undecane-1-ol, 2-heptadecanol, benzyl alcohol, 2-phenylethanol, furfuryl alcohol, other alcohols; isoprene, pentane, cyclopentane, hexane, cyclohexane, heptane, octane, octa-1-ene, octa-2,4-diene, nonane, decane, tridecane, tetradecane, hexadecane, octadecane, nonadecane, eicosane, methylbenzene, 1-methyl-4-(1-methylethyl)benzene, naphthalene, other hydrocarbons; dichloromethane, 1,1,1-trichloroethane, chlorobenzene, 1,4-dichlorobenze, other chlorinated hydrocarbons; diphenyl ether, other ethers; and mixtures thereof. In yet another embodiment, said aptamer composition has a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof.

In the present invention, said aptamer composition may comprise at least one oligonucleotide selected from the group consisting of oligonucleotides with at least 50% nucleotide sequence identity to sequences selected from the group consisting of SEQ ID NO 1 to SEQ ID NO 400 and SEQ ID NO 407 to SEQ ID NO 415. In the present invention, said aptamer composition may comprise at least one oligonucleotide selected from the group consisting of oligonucleotides with at least 70% nucleotide sequence identity to sequences selected from the group consisting of SEQ ID NO 1 to SEQ ID NO 400 and SEQ ID NO 407 to SEQ ID NO 415. In the present invention, said aptamer composition may comprise at least one oligonucleotide selected from the group consisting of oligonucleotides with at least 90% nucleotide sequence identity to sequences selected from the group consisting of SEQ ID NO 1 to SEQ ID NO 400 and SEQ ID NO 407 to SEQ ID NO 415. In the present invention, said aptamer composition may comprise at least one oligonucleotide selected from the group consisting of SEQ ID NO 1 to SEQ ID NO 400 and SEQ ID NO 407 to SEQ ID NO 415. A non-limiting example of oligonucleotides with at least 90% nucleotide sequence identity to SEQ ID NO 87 is SEQ ID NO 204 (see FIG. 5). Non-limiting examples of oligonucleotides with at least 90% nucleotide sequence identity to SEQ ID NO 130 are SEQ ID NO 195 and SEQ ID NO 265. Non-limiting examples of oligonucleotides with at least 90% nucleotide sequence identity to SEQ ID NO 201 are SEQ ID NO 208 and SEQ ID NO 344. A non-limiting example of oligonucleotides with at least 70% nucleotide sequence identity to SEQ ID NO 363 is SEQ ID NO 385 (see FIG. 6). A non-limiting example of oligonucleotides with at least 50% nucleotide sequence identity to SEQ ID NO 59 is SEQ ID NO 296 (see FIG. 7). Non-limiting examples of oligonucleotides with at least 50% nucleotide sequence identity to SEQ ID NO 245 are SEQ ID NO 302 and SEQ ID NO 317.

In another embodiment of the present invention, said aptamer composition may comprise at least one oligonucleotide selected from the group consisting of SEQ ID NO 1, SEQ ID NO 2, SEQ ID NO 102, SEQ ID NO 103, SEQ ID NO 201, SEQ ID NO 217, SEQ ID NO 301, SEQ ID NO 302, SEQ ID NO 407, SEQ ID NO 408, SEQ ID NO 409, SEQ ID NO 410, SEQ ID NO 411, SEQ ID NO 412, SEQ ID NO 413, SEQ ID NO 414, and SEQ ID NO 415. In the present invention, said aptamer composition may comprise at least one oligonucleotide selected from the group consisting of oligonucleotides with at least 50% nucleotide sequence identity to sequences selected from the group consisting of SEQ ID NO 1, SEQ ID NO 2, SEQ ID NO 102, SEQ ID NO 103, SEQ ID NO 201, SEQ ID NO 217, SEQ ID NO 301, SEQ ID NO 302, SEQ ID NO 407, SEQ ID NO 408, SEQ ID NO 409, SEQ ID NO 410, SEQ ID NO 411, SEQ ID NO 412, SEQ ID NO 413, SEQ ID NO 414, and SEQ ID NO 415. In the present invention, said aptamer composition may comprise at least one oligonucleotide selected from the group consisting of oligonucleotides with at least 70% nucleotide sequence identity to sequences selected from the group consisting of SEQ ID NO 1, SEQ ID NO 2, SEQ ID NO 102, SEQ ID NO 103, SEQ ID NO 201, SEQ ID NO 217, SEQ ID NO 301, SEQ ID NO 302, SEQ ID NO 407, SEQ ID NO 408, SEQ ID NO 409, SEQ ID NO 410, SEQ ID NO 411, SEQ ID NO 412, SEQ ID NO 413, SEQ ID NO 414, and SEQ ID NO 415. In the present invention, said aptamer composition may comprise at least one oligonucleotide selected from the group consisting of oligonucleotides with at least 90% nucleotide sequence identity to sequences selected from the group consisting of SEQ ID NO 1, SEQ ID NO 2, SEQ ID NO 102, SEQ ID NO 103, SEQ ID NO 201, SEQ ID NO 217, SEQ ID NO 301, SEQ ID NO 302, SEQ ID NO 407, SEQ ID NO 408, SEQ ID NO 409, SEQ ID NO 410, SEQ ID NO 411, SEQ ID NO 412, SEQ ID NO 413, SEQ ID NO 414, and SEQ ID NO 415. A non-limiting example of oligonucleotide with at least 90% nucleotide sequence identity to SEQ ID NO 102 is SEQ ID NO 306. Non-limiting examples of oligonucleotides with at least 90% nucleotide sequence identity to SEQ ID NO 103 are SEQ ID NO 261 and SEQ ID NO 305. Non-limiting examples of oligonucleotides with at least 90% nucleotide sequence identity to SEQ ID NO 201 are SEQ ID NO 208 and SEQ ID NO 344. A non-limiting example of oligonucleotide with at least 50% nucleotide sequence identity to SEQ ID NO 201 is SEQ ID NO 196. Non-limiting examples of oligonucleotides with at least 50% nucleotide sequence identity to SEQ ID NO 302 are SEQ ID NO 245 and SEQ ID NO 317.

In the present invention, said aptamer composition may comprise at least one oligonucleotide selected from the group consisting of oligonucleotides containing at least 10 contiguous nucleotides from sequences selected from the group consisting of SEQ ID NO 1 to SEQ ID NO 400. In the present invention, said aptamer composition may comprise at least one oligonucleotide selected from the group consisting of oligonucleotides containing at least 20 contiguous nucleotides from sequences selected from the group consisting of SEQ ID NO 1 to SEQ ID NO 400. In the present invention, said aptamer composition may comprise at least one oligonucleotide selected from the group consisting of oligonucleotides containing at least 40 contiguous nucleotides from sequences selected from the group consisting of SEQ ID NO 1 to SEQ ID NO 400. In the present invention, said aptamer composition may comprise at least one oligonucleotide selected from the group consisting of oligonucleotides containing at least 60 contiguous nucleotides from sequences selected from the group consisting of SEQ ID NO 1 to SEQ ID NO 400. In the present invention, said aptamer composition may comprise at least one oligonucleotide selected from the group consisting of oligonucleotides containing at least 70 contiguous nucleotides from sequences selected from the group consisting of SEQ ID NO 1 to SEQ ID NO 400. Non-limiting examples of oligonucleotides containing at least 10 contiguous nucleotides from SEQ ID NO 1 are SEQ ID NO 407, SEQ ID NO 408, SEQ ID NO 409, and SEQ ID NO 410. Non-limiting examples of oligonucleotides containing at least 10 contiguous nucleotides from SEQ ID NO 2 are SEQ ID NO 411 and SEQ ID NO 412. A non-limiting example of oligonucleotide containing at least 10 contiguous nucleotides from SEQ ID NO 3 is SEQ ID NO 413. Non-limiting examples of oligonucleotides containing at least 10 contiguous nucleotides from SEQ ID NO 4 are SEQ ID NO 414 and SEQ ID NO 415.

In another embodiment of the present invention, said at least one oligonucleotide may comprise one or more motifs selected from the group consisting of SEQ ID NO 401, SEQ ID NO 402, SEQ ID NO 403, SEQ ID NO 404, SEQ ID NO 405, and SEQ ID NO 406. In the present invention, said aptamer composition may comprise at least one oligonucleotide comprising a sequence of nucleotides with at least 70% nucleotide sequence identity to sequences selected from the group consisting of SEQ ID NO 401, SEQ ID NO 402, SEQ ID NO 403, SEQ ID NO 404, SEQ ID NO 405, and SEQ ID NO 406. In the present invention, said aptamer composition may comprise at least one oligonucleotide comprising a sequence of nucleotides with at least 80% nucleotide sequence identity to sequences selected from the group consisting of SEQ ID NO 401, SEQ ID NO 402, SEQ ID NO 403, SEQ ID NO 404, SEQ ID NO 405, and SEQ ID NO 406. In the present invention, said aptamer composition may comprise at least one oligonucleotide comprising a sequence of nucleotides with at least 90% nucleotide sequence identity to sequences selected from the group consisting of SEQ ID NO 401, SEQ ID NO 402, SEQ ID NO 403, SEQ ID NO 404, SEQ ID NO 405, and SEQ ID NO 406.

Chemical modifications can introduce new features into the aptamers such as different molecular interactions with the target, improved binding capabilities, enhanced stability of oligonucleotide conformations, or increased resistance to nucleases. In the present invention, said at least one oligonucleotide of said aptamer composition may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methyl-cytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, bromouracil, 5-iodouracil, and mixtures thereof.

Modifications of the phosphate backbone of the oligonucleotides can also increase the resistance against nuclease digestion. In the present invention, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In the present invention, the nucleosides of said oligonucleotides may be linked by natural phosphate diesters.

In the present invention, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In the present invention, said derivatives of ribonucleotides or said derivatives of deoxyribonucleotides may be selected from the group comprising: locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

In the present invention, the nucleotides at the 5'- and 3'-ends of said at least one oligonucleotide may be inverted. In the present invention, at least one nucleotide of said at least one oligonucleotide may be fluorinated at the 2' position of the pentose group. In the present invention, the pyrimidine nucleotides of said at least one oligonucleotide may be fluorinated at the 2' position of the pentose group. In the present invention, said aptamer composition may comprise at least one polymeric material, wherein said at least one polymeric material is covalently linked to said at least one oligonucleotide. In the present invention, said at least one polymeric material may be polyethylene glycol.

In the present invention, said at least one oligonucleotide may be between about 10 and about 200 nucleotides in length. In the present invention, said at least one oligonucleotide may be less than about 100 nucleotides in length. In the present invention, said at least one oligonucleotide may be less than about 50 nucleotides in length.

In the present invention, said at least one oligonucleotide may be covalently or non-covalently attached to another material. In the present invention, said at least one oligonucleotide may be non-covalently attached to another material via molecular interactions. Examples of molecular interactions are electrostatic forces, van der Waals interactions, hydrogen bonding, and π-π stacking interactions of aromatic rings. In the present invention, said at least one oligonucleotide may be covalently attached to another material using one or more linkers or spacers. Non-limiting examples of linkers are chemically labile linkers, enzyme-labile linkers, and non-cleavable linkers. Examples of chemically labile linkers are acid-cleavable linkers and disulfide linkers. Acid-cleavable linkers take advantage of low pH to trigger hydrolysis of an acid-cleavable bond, such as a hydrazone bond, to release the active ingredient or payload. Disulfide linkers can release the active ingredients under reducing environments. Examples of enzyme-labile linkers are peptide linkers that can be cleaved in the present of proteases and β-glucuronide linkers that are cleaved by glucuronidases releasing the payload. Non-cleavable linkers can also release the active ingredient if the aptamer is degraded by nucleases.

In the present invention, said at least one oligonucleotide may be covalently or non-covalently attached to one or more nanomaterials. Non-limiting examples of nanomaterials are gold nanoparticles, nano-scale iron oxides, carbon nanomaterials (such as single-walled carbon nanotubes and graphene oxide), mesoporous silica nanoparticles, quantum dots, liposomes, poly (lactide-co-glycolic acids) nanoparticles, polymeric micelles, dendrimers, serum albumin nanoparticles, and DNA-based nanomaterials. These nanomaterials can serve as carriers for large volumes of personal care active ingredients, while the aptamers can facilitate the delivery of the nanomaterials with the actives to the expected target.

Nanomaterials can have a variety of shapes or morphologies. Non-limiting examples of shapes or morphologies are spheres, rectangles, polygons, disks, toroids, cones, pyramids, rods/cylinders, and fibers. In the context of the present invention, nanomaterials usually have at least one spatial dimension that is less than about 100 μm and more preferably less than about 10 μm. Nanomaterials comprise materials in solid phase, semi-solid phase, or liquid phase.

Aptamers can also be peptides that bind to targets with high affinity and specificity. These peptide aptamers can be part of a scaffold protein. Peptide aptamers can be isolated from combinatorial libraries and improved by directed mutation or rounds of variable region mutagenesis and selection. In the present invention, said aptamer composition may comprise at least one peptide or protein; wherein said aptamer composition has a binding affinity for one or more volatile organic compounds selected from the group consisting of: sulfur containing compounds, nitrogen-containing compounds, carboxylic acids, esters, aldehydes, ketones, alcohols, hydrocarbons, and mixtures thereof. In the present invention, said one or more volatile organic compounds may be selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof.

III. Methods of Designing Aptamer Compositions

The method of designing nucleic acid aptamers known as *Systematic Evolution of Ligands by Exponential Enrichment* (SELEX) has been broadly studied and improved for the selection of aptamers against small molecules and proteins (WO 91/19813). In brief, in the conventional version of SELEX, the process starts with the synthesis of a large library of oligonucleotides consisting of randomly generated sequences of fixed length flanked by constant 5'- and 3'-ends that serve as primers. The oligonucleotides in the library are then exposed to the target ligand and those that do not bind the target are removed. The bound sequences are eluted and amplified by PCR (polymerase chain reaction) to prepare for subsequent rounds of selection in which the stringency of the elution conditions is usually increased to identify the tightest-binding oligonucleotides. In addition to conventional SELEX, there are improved versions such as capillary electrophoresis-SELEX, magnetic bead-based SELEX, cell-SELEX, automated SELEX, complex-target SELEX, among others. A review of aptamer screening methods is found in (1) Kim, Y. S. and M. B. Gu, "Advances in Aptamer Screening and Small Molecule Aptasensors", Adv. Biochem. Eng. Biotechnol., 2014 140:29-67 (Biosensors based on Aptamers and Enzymes) and (2) Stoltenburg, R., et al. (2007) "SELEX-A (r)evolutionary method to generate high-affinity nucleic acid ligands" Biomol. Eng. 2007 24(4): 381-403, the contents of which are incorporated herein by reference. Although the SELEX method has been broadly applied, it is neither predictive nor standardized for every target. Instead, a method must be developed for each particular target in order for the method to lead to viable aptamers.

Traditional SELEX approaches require for the target molecules to be immobilized in order to partition aptamers that bind to the targets from aptamers that do not bind to them. This methodology presents a significant constraint regarding the identification of aptamers that bind to small molecules as the process of immobilization of a such targets involves their conjugation to a larger supporting structure and the modification of their chemical structure.

In this instance, the small molecule targets were (E)-3-methyl-2-hexenoic acid, 3-methyl-3-hydroxy hexanoic acid, 3-methyl-3-sulfanylhexan-1-ol, and 3-sulfanylhexan-1-ol. For instance, for the targets containing a carboxylic acid, a standard chemical approach to conjugate these molecules to a support would be to use EDC mediated conjugation of the carboxylic group to a primary amine on a solid support such as CarboxyLink Resin (Fisher Scientific, Catalog number: 20266). An example of this type of immobilization chemistry is schematically outlined for (E)-3-methyl-2-hexenoic acid in FIG. 1.

The use of such a process would change the nature of the target molecule. In particular, the carboxylic group would be lost as a charged group capable of binding to positively charged nucleotides within an aptamer. The remaining charged groups would be either weakly positively charged (methyl groups) or weakly negatively charged (ketone group). As such, it is clear that the use of a method such as FRELEX (WO 2017/035666 A1 and Lecocq Soizic, et al. "Aptamers as biomarkers for neurological disorders. Proof of concept in transgenic mice." 5 Jan. 2018 PLOS ONE, https://doi.org/10.1371/journal.pone.0190212) is advantageous in terms of maintaining the structure of the target molecule. The applicants have found that FRELEX can be used for the design of aptamers with high binding affinity and specificity for small molecules such as (E)-3-methyl-2-hexenoic acid, 3-methyl-3-hydroxy hexanoic acid, 3-methyl-3-sulfanylhexan-1-ol, and 3-sulfanylhexan-1-ol.

Selection Library

In SELEX and FRELEX, the initial candidate library is generally a mixture of chemically synthesized DNA oligonucleotides, each comprising a long variable region of n nucleotides flanked at the 3' and 5' ends by conserved regions or primer recognition regions for all the candidates of the library. These primer recognition regions allow the central variable region to be manipulated during SELEX and FRELEX in particular by means of PCR.

The length of the variable region determines the diversity of the library, which is equal to $4^n$ since each position can be occupied by one of four nucleotides A, T, G or C. For long variable regions, huge library complexities arise. For instance, when n=50, the theoretical diversity is $4^{50}$ or $10^{30}$, which is an inaccessible value in practice as it corresponds to more than $10^5$ tons of material for a library wherein each sequence is represented once. The experimental limit is around $10^{15}$ different sequences, which is that of a library wherein all candidates having a variable region of 25 nucleotides are represented. If one chooses to manipulate a library comprising a 30-nucleotide variable region whose theoretical diversity is about $10^{18}$, only $\frac{1}{1000}$ of the possibilities will thus be explored. In practice, that is generally sufficient to obtain aptamers having the desired properties. Additionally, since the polymerases used are unreliable and introduce errors at a rate on the order of $10^{-4}$, they contribute to significantly enrich the diversity of the sequence pool throughout the SELEX or FRELEX processes. One candidate in 100 will be modified in each amplification cycle for a library with a random region of 100 nucleotides in length, thus leading to the appearance of $10^{13}$ new candidates for the overall library.

In the present invention, the starting mixture of oligonucleotides may comprise more than about $10^6$ different oligonucleotides and more preferably between about $10^{13}$ to about $10^{15}$ different oligonucleotides. In the present invention, the length of the variable region may be between about 10 and about 100 nucleotides. In the present invention, the length of the variable region may be between about 20 and about 60 nucleotides. In the present invention, the length of the variable region may be about 40 nucleotides. Random regions shorter than 10 nucleotides may be used, but may be constrained in their ability to form secondary or tertiary structures and in their ability to bind to target molecules. Random regions longer than 100 nucleotides may also be used but may present difficulties in terms of cost of synthesis. The randomness of the variable region is not a constraint of the present invention. For instance, if previous knowledge exists regarding oligonucleotides that bind to a given target, libraries spiked with such sequences may work as well or better than completely random ones.

In the design of primer recognition sequences, care should be taken to minimize potential annealing among sequences, fold back regions within sequences, or annealing of the same sequence itself. In the present invention, the length of primer recognition sequences may be between about 10 and about 40 nucleotides. In the present invention, the length of primer recognition sequences may be between about 12 and about 30 nucleotides. In the present invention, the length of primer recognition sequences may be between about 18 and about 26 nucleotides, i.e., about 18, 19, 20, 21, 22, 23, 24, 25 or 26 nucleotides. The length and sequence of the primer recognition sequences determine their annealing temperature. In the present invention, the primer recognition sequences of said oligonucleotides may have an annealing temperature between about 60° C. and about 72° C.

Aptamers can be ribonucleotides (RNA), deoxynucleotides (DNA), or their derivatives. When aptamers are ribonucleotides, the first SELEX or FRELEX step may consist in transcribing the initial mixture of chemically synthesized DNA oligonucleotides via the primer recognition sequence at the 5' end. After selection, the candidates are converted back into DNA by reverse transcription before being amplified. RNA and DNA aptamers having comparable characteristics have been selected against the same target and reported in the art. Additionally, both types of aptamers can be competitive inhibitors of one another, suggesting potential overlapping of interaction sites.

New functionalities, such as hydrophobicity or photoreactivity, can be incorporated into the oligonucleotides by modifications of the nucleobases before or after selection. Modifications at the C-5 position of pyrimidines or at the C-8 or N-7 positions of purines are especially common and compatible with certain enzymes used during the amplification step in SELEX or FRELEX. In the present invention, said oligonucleotides may comprise natural or non-natural nucleobases. Natural nucleobases are adenine, cytosine, guanine, thymine, and uracil. Non-limiting examples of non-natural nucleobases are hypoxanthine, xanthine, 7-methylguanine, 5,6-dihydrouracil, 5-5-methylcytosine, 5-hydroxymethylcytosine, thiouracil, 1-methylhypoxanthine, 6-methylisoquinoline-1-thione-2-yl, 3-methoxy-2-naphthyl, 5-propynyluracil-1-yl, 5-methylcytosin-1-yl, 2-aminoadenin-9-yl, 7-deaza-7-iodoadenin-9-yl, 7-deaza-7-propynyl-2-aminoadenin-9-yl, phenoxazinyl, phenoxazinyl-G-clam, 5-bromouracil, 5-iodouracil, and mixtures thereof. Some non-natural nucleobases, such as 5-bromouracil or 5-iodouracil, can be used to generate photo-crosslinkable aptamers, which can be activated by UV light to form a covalent link with the target.

In the present invention, the nucleosides of said oligonucleotides may be linked by a chemical motif selected from the group comprising natural phosphate diester, chiral phosphorothionate, chiral methyl phosphonate, chiral phosphoramidate, chiral phosphate chiral triester, chiral boranophosphate, chiral phosphoroselenoate, phosphorodithioate, phosphorothionate amidate, methylenemethylimino, 3'-amide, 3' achiral phosphoramidate, 3' achiral methylene phosphonates, thioformacetal, thioethyl ether, fluorophosphate, and mixtures thereof. In the present invention, the nucleosides of said oligonucleotides may be linked by natural phosphate diesters.

In the present invention, the sugar moiety of the nucleosides of said oligonucleotides may be selected from the group comprising ribose, deoxyribose, 2'-fluoro deoxyribose, 2'-O-methyl ribose, 2'-O-(3-amino)propyl ribose, 2'-O-(2-methoxy)ethyl ribose, 2'-O-2-(N,N-dimethylaminooxy)ethyl ribose, 2'-O-2-[2-(N,N-dimethylamino)ethyloxy]ethyl ribose, 2'-O—N,N-dimethylacetamidyl ribose, N-morpholinophosphordiamidate, α-deoxyribofuranosyl, other pentoses, hexoses, and mixtures thereof.

In the present invention, said derivatives of ribonucleotides or said derivatives of deoxyribonucleotides may be selected from the group comprising locked oligonucleotides, peptide oligonucleotides, glycol oligonucleotides, threose oligonucleotides, hexitol oligonucleotides, altritol oligonucleotides, butyl oligonucleotides, L-ribonucleotides, arabino oligonucleotides, 2'-fluoroarabino oligonucleotides, cyclohexene oligonucleotides, phosphorodiamidate morpholino oligonucleotides, and mixtures thereof.

When using modified nucleotides during the SELEX or FRELEX processes, they should be compatible with the enzymes used during the amplification step. Non-limiting examples of modifications that are compatible with commercial enzymes include modifications at the 2' position of the sugar in RNA libraries. The ribose 2'-OH group of pyrimidine nucleotides can be replaced with 2'-amino, 2'-fluoro, 2'-methyl, or 2'-O-methyl, which protect the RNA from degradation by nucleases. Additional modifications in the phosphate linker, such as phosphorothionate and boranophosphate, are also compatible with the polymerases and confer resistance to nucleases.

In the present invention, at least one nucleotide of said oligonucleotides may be fluorinated at the 2' position of the pentose group. In the present invention, the pyrimidine nucleotides of said oligonucleotides may be at least partially fluorinated at the 2' position of the pentose group. In the present invention, all the pyrimidine nucleotides of said oligonucleotides may be fluorinated at the 2' position of the pentose group. In the present invention, at least one nucleotide of said oligonucleotides may be aminated at the 2' position of the pentose group.

Another approach, recently described as two-dimensional SELEX, simultaneously applies in vitro oligonucleotide selection and dynamic combinatorial chemistry (DCC), e.g., a reversible reaction between certain groups of the oligonucleotide (amine groups) and a library of aldehyde compounds. The reaction produces imine oligonucleotides, which are selected on the same principles as for conventional SELEX. It is thus possible to identify for a target hairpin RNA modified aptamers that differ from natural aptamers.

A very different approach relates to the use of optical isomers. Natural oligonucleotides are D-isomers. L-analogs are resistant to nucleases but cannot be synthesized by polymerases. According to the laws of optical isomerism, an L-series aptamer can form with its target (T) a complex having the same characteristics as the complex formed by the D-series isomer and the enantiomer (T') of the target (T). Consequently, if compound T' can be chemically synthesized, it can be used to perform the selection of a natural aptamer (D). Once identified, this aptamer can be chemically synthesized in an L-series. This L-aptamer is a ligand of the natural target (T).

Selection Step

Single stranded oligonucleotides can fold to generate secondary and tertiary structures, resembling the formation of base pairs. The initial sequence library is thus a library of three-dimensional shapes, each corresponding to a distribution of units that can trigger electrostatic interactions, create hydrogen bonds, etc. Selection becomes a question of identifying in the library the shape suited to the target, i.e., the shape allowing the greatest number of interactions and the formation of the most stable aptamer-target complex. For small targets (dyes, antibiotics, etc.) the aptamers identified are characterized by equilibrium dissociation constants in the micromolar range, whereas for protein targets $K_d$ values below $10^{-9}$ M are not rare.

Selection in each round occurs by means of physical separation of oligonucleotides associated with the target from free oligonucleotides. Multiple techniques may be applied (chromatography, filter retention, electrophoresis, etc.). The selection conditions are adjusted (relative concentration of target/candidates, ion concentration, temperature, washing, etc.) so that a target-binding competition occurs between the oligonucleotides. Generally, stringency is increased as the rounds proceed in order to promote the capture of oligonucleotides with the highest affinity. In addition, counter-selections or negative selections are carried out to eliminate oligonucleotides that recognize the support or unwanted targets (e.g., filter, beads, etc.).

The SELEX and FRELEX processes for the selection of target-specific aptamers are characterized by repetition of five main steps: (1) binding of oligonucleotides to the target, (2) partition or removal of oligonucleotides with low binding affinity, (3) elution of oligonucleotides with high binding affinity, (4) amplification or replication of oligonucleotides with high binding affinity, and (5) conditioning or preparation of the oligonucleotides for the next cycle. This selection process is designed to identify the oligonucleotides with the greatest affinity and specificity for the target material.

In the present invention, a method of designing an aptamer composition may comprise the step of contacting: a) a mixture of oligonucleotides, b) a selection buffer, and c) one or more volatile organic compounds selected from the group consisting of: sulfur containing compounds, nitrogen-containing compounds, carboxylic acids, esters, aldehydes, ketones, alcohols, hydrocarbons, and mixtures thereof. In the present invention, said one or more volatile organic compounds may be selected from the group consisting of: 3-methyl-3-sulfanylhexan-1-ol, 3-sulfanylhexan-1-ol, methanethiol, dimethyl sulfide, dimethyl disulfide, dimethyl trisulfide, hydrogen sulfide, carbon disulfide, 3-methylthiopropanal, dimethyl sulfone; (E)-3-methyl-2-hexenoic acid, 3-methyl-3-hydroxy hexanoic acid, nonanoic acid, octanoic acid, 4-ethyloctanoic acid, heptanoic acid, hexanoic acid, 2-ethylhexanoic acid, pentanoic acid, isovaleric acid, butyric acid, 3-methyl butanoic acid, propanoic acid, acetic acid, formic acid, other 3-methyl carboxylic acids, other carboxylic acids; methyl acetate, ethyl acetate, benzyl acetate, ethyl butanoate, octyl formate, 2-ethylhexyl-salicylate, γ-nonalactone, other esters of carboxylic acids; ammonia, methylamine, ethylamine, trimethylamine, pyrazine, pyridine, 2-methylpyridine, 2-ethylpyridine, 2,3,5-trimethylpyridine, pyrrole, 1-methyl pyrrole, acetonitrile, N,N-dimethylformamide, 1-(2-aminophenyl) ethenone, 4-morpholine ethanamine, 4-cyanocyclohexene, indole, 3-methyl indole, other nitrogen-containing compounds; propanal, 1,2-methyl propanal, butanal, 2-methyl butanal, 3-methyl butanal, pentanal, (E)-2-pentenal, hexanal, (E)-2-hexenal, heptanal, octanal, (E)-2-octenal, nonanal, 2-nonenal, decanal, 2,6-nonadienal, undecanal, dodecanal, tridecanal, benzaldehyde, other aldehydes; diacetyl (2,3-butanedione); 2-methoxyphenol, propanone, butanone, pentan-2-one, pentan-3-one, cyclopentanone, hexan-2-one, cyclohexanone, heptan-2-one, heptan-3-one, oct-1-en-3-one, 2,3-octadione, nonan-2-one, androstenone, 1-phenyl-ethanone, acetophenone, furan, 2-methylfuran, 3-methylfuran, 2,5-diethylfuran, other ketones; ethanol, 2-ethoxyethanol, 2-butoxyethanol, propan-2-ol, 2-methyl-1-propanol, butanol, 3-methyl-1-butanol, pentan-1-ol, pentan-2-ol, hexan-1-ol, oct-1-en-3-ol, 2-butyl-1-octanol, nonan-1-ol, decan-1-ol, cyclodecanol, undecane-1-ol, 2-heptadecanol, benzyl alcohol, 2-phenylethanol, furfuryl alcohol, other alcohols; isoprene, pentane, cyclopentane, hexane, cyclohexane, heptane, octane, octa-1-ene, octa-2,4-diene, nonane, decane, tridecane, tetradecane, hexadecane, octadecane, nonadecane, eicosane, methylbenzene, 1-methyl-4-(1-methylethyl)benzene, naphthalene, other hydrocarbons; dichloromethane, 1,1,1-trichloroethane, chlorobenzene, 1,4-dichlorobenze, other chlorinated hydrocarbons; diphenyl ether, other ethers; and mixtures thereof. In the present invention, said one or more volatile organic compounds may be selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof. In the present invention, said mixture of oligonucleotides may comprise oligonucleotides composed of nucleotides selected from the group consisting of: deoxyribonucleotides, ribonucleotides, derivatives of deoxyribonucleotides, derivatives of ribonucleotides, and mixtures thereof.

SELEX and FRELEX cycles are usually repeated several times until oligonucleotides with high binding affinity are identified. The number of cycles depends on multiple variables, including target features and concentration, design of the starting random oligonucleotide library, selection conditions, ratio of target binding sites to oligonucleotides, and the efficiency of the partitioning step. In the present invention, said contacting step may be performed at least 5 times. In the present invention, said contacting step may be performed between 6 and 15 times. In the present invention, said method further may comprise the step of removing the oligonucleotides that do not bind said target material during said contacting step.

Oligonucleotides are oligo-anions, each unit having a charge and hydrogen-bond donor/acceptor sites at a particular pH. Thus, the pH and ionic strength of the selection buffer are important and should represent the conditions of the intended aptamer application. In the present invention, the pH of said selection buffer may be between about 2 and about 9. In the present invention, the pH of said selection buffer may be between about 5 and about 8.

Cations do not only facilitate the proper folding of the oligonucleotides, but also can provide benefits to the hair or the scalp. In the present invention, said selection buffer may comprise cations. Non-limiting examples of cations are $Mg^{2+}$, $Ca^{2+}$, $Sn^{2+}$, $Sn^{4+}$, $Zn^{2+}$, $Al^{3+}$, $Cu^{2+}$, $Fe^{2+}$, and $Fe^{3+}$.

In order for the aptamers to maintain their structures and function during their application, the in vitro selection process can be carried out under conditions similar to those for which they are being developed. In the present invention, said selection buffer may comprise a solution or suspension of a personal care composition selected from the group comprising sprays, liquids, pastes, Newtonian or non-Newtonian fluids, gels, and sols. In the present invention, said selection buffer may comprise a solution of a deodorant chassis.

In the present invention, said selection buffer may comprise at least one surfactant. In the present invention, said at least one surfactant may be selected from the group consisting of anionic surfactants, amphoteric or zwitterionic surfactants, and mixtures thereof. Non-limiting examples of anionic surfactants are alkyl and alkyl ether sulfates or sulfonates, including ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof. Non-limiting amphoteric surfactants include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate, including cocoamphoacetate, cocoamphodiacetate, lauroamphoacetate, lauroamphodiacetate, and mixtures thereof. Non-limiting examples of zwitterionic surfactants include those surfactants broadly described as derivatives of aliphatic quaternaryammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate, and betains.

Negative selection or counter-selection steps can minimize the enrichment of oligonucleotides that bind to undesired targets or undesired epitopes within a target. In the present invention, said method of designing an aptamer composition may further comprise the step of contacting: a) a mixture of oligonucleotides, b) a selection buffer, and c) one or more undesired targets. Methods for negative selection or counter-selection of aptamers against unbound targets have been published in WO201735666, the content of which is incorporated herein by reference.

In the present invention, the method of designing an aptamer composition may comprise the steps of: a) synthesizing a mixture of oligonucleotides; and b) contacting: i. said mixture of oligonucleotides, ii. a selection buffer, and iii. a target material selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof, to produce a target solution. In the present invention, said steps may be performed repetitively at least 5 times. In the present invention, said steps may be performed between 6 and 15 times.

Post-Selection Modification

To enhance stability of the aptamers, chemical modifications can be introduced in the aptamer after the selection process. For instance, the 2'-OH groups of the ribose moieties can be replaced by 2'-fluoro, 2'-amino, or 2'-O-methyl groups. Furthermore, the 3'- and 5'-ends of the aptamers can be capped with different groups, such as streptavidin-biotin, inverted thymidine, amine, phosphate, polyethylene-glycol, cholesterol, fatty acids, proteins, enzymes, fluorophores, among others, making the oligonucleotides resistant to exonucleases or providing some additional benefits. Other modifications are described in previous sections of the present disclosure.

Unlike backbone modifications which can cause aptamer-target interaction properties to be lost, it is possible to conjugate various groups at one of the 3'- or 5'-ends of the oligonucleotide in order to convert it into a delivery vehicle, tool, probe, or sensor without disrupting its characteristics. This versatility constitutes a significant advantage of aptamers.

Incorporation of modifications to aptamers can be performed using enzymatic or chemical methods. Non-limiting examples of enzymes used for modification of aptamers are terminal deoxynucleotidyl transferases (TdT), T4 RNA ligases, T4 polynucleotide kinases (PNK), DNA polymerases, RNA polymerases, and other enzymes known by those skilled in the art. TdTs are template-independent polymerases that can add modified deoxynucleotides to the 3' terminus of deoxyribonucleotides. T4 RNA ligases can be used to label ribonucleotides at the 3'-end by using appropriately modified nucleoside 3',5'-bisphosphates. PNK can be used to phosphorylate the 5'-end of synthetic oligonucleotides, enabling other chemical transformations (see below). DNA and RNA polymerases are commonly used for the random incorporation of modified nucleotides throughout the sequence, provided such nucleotides are compatible with the enzymes.

Non-limiting examples of chemical methods used for modification of aptamers are periodate oxidation of ribonucleotides, EDC activation of 5'-phosphate, random chemical labeling methods, and other chemical methods known by those skilled in the art, incorporated herein.

During periodate oxidation, meta- and ortho-periodates cleave the C—C bonds between vicinal diols of 3'-ribonucleotides, creating two aldehyde moieties that enable the conjugation of labels or active ingredients at the 3'-end of RNA aptamers. The resulting aldehydes can be easily reacted with hydrazide- or primary amine-containing molecules. When amines are used, the produced Schiff bases can be reduced to more stable secondary amines with sodium cyanoborohydride ($NaBH_4$).

When EDC activation of 5'-phosphate is used, the 5'-phosphate of oligonucleotides is frequently activated with EDC (1-Ethyl-3-[3-dimethylaminopropyl]carbodiimide hydrochloride) and imidazole to produce a reactive imidazolide intermediate, followed by reaction with a primary amine to generate aptamers modified at the 5' end. Because the 5' phosphate group is required for the reaction, synthetic oligonucleotides can be first treated with a kinase (e.g. PNK).

Random chemical labeling can be performed with different methods. Because they allow labeling at random sites along the aptamer, a higher degree of modification can be achieved compared to end-labeling methods. However, since the nucleobases are modified, binding of the aptamers to their target can be disrupted. The most common random chemical modification methods involve the use of photoreactive reagents, such as phenylazide-based reagents. When the phenylazide group is exposed to UV light, it forms a labile nitrene that reacts with double bonds and C—H and N—H sites of the aptamers.

Additional information about methods for modification of aptamers is summarized in Hermanson G. T., "Bioconjugate Techniques", pp. 969-1002, 2nd Edition, Academic Press, San Diego, 2008, the content of which is incorporated herein by reference.

After selection, in addition to chemical modifications, sequence truncations can be performed to remove regions that are not essential for binding or for folding into the structure. Moreover, aptamers can be linked together to provide different features or better affinity. Thus, any truncations or combinations of the aptamers described herein are incorporated as part of the current invention.

IV. Application of Aptamer Compositions in Personal Care Compositions

The aptamers of the current invention can be used in personal care compositions to provide one or more benefits. Personal care compositions may include antiperspirants and deodorants.

The aptamers of the current invention may be used in antiperspirant and/or deodorant compositions. Antiperspirant and deodorant compositions can be formulated in many forms. For example, an antiperspirant composition can be, without limitation, a roll on product, a body spray, a stick including soft solid sticks and invisible solids, or an aerosol. Each of the antiperspirant compositions described below can include aptamers as described herein. Any antiperspirant and/or deodorant composition disclosed herein may comprise at least one aptamer, wherein the at least one aptamer comprises from about 0.001% to about 1% of the composition, by weight of the composition. In another embodiment, said antiperspirant and/or deodorant composition may comprise at least one aptamer, wherein the at least one aptamer comprises from about 0.005% to about 0.5% of the composition, by weight of the composition. In yet another embodiment, said antiperspirant and/or deodorant composition may comprise at least one aptamer, wherein the at least one aptamer comprises from about 0.01% to about 0.1% of the composition, by weight of the composition.

A. Roll-On and Clear Gel

A roll-on antiperspirant composition can comprise, for example, water, emollient, solubilizer, deodorant actives, antioxidants, preservatives, or combinations thereof. A clear gel antiperspirant composition can comprise, for example, water, emollient, solubilizer, deodorant actives, antioxidants, preservatives, ethanol, or combinations thereof.

Water

The roll-on composition can include water. Water can be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the deodorant composition.

Emollients

Roll-on compositions can comprise an emollient system including at least one emollient, but it could also be a combination of emollients. Suitable emollients are often liquid under ambient conditions. Depending on the type of product form desired, concentrations of the emollient(s) in the deodorant compositions can range from about 1% to about 95%, from about 5% to about 95%, from about 15% to about 75%, from about 1% to about 10%, from about 15% to about 45%, or from about 1% to about 30%, by weight of the deodorant composition.

Emollients suitable for use in the roll-on compositions include, but are not limited to, propylene glycol, polypropylene glycol (like dipropylene glycol, tripropylene glycol, etc.), diethylene glycol, triethylene glycol, PEG-4, PEG-8, 1,2 pentanediol, 1,2 hexanediol, hexylene glycol, glycerin, C2 to C20 monohydric alcohols, C2 to C40 dihydric or polyhydric alcohols, alkyl ethers of polyhydric and monohydric alcohols, volatile silicone emollients such as cyclopentasiloxane, nonvolatile silicone emollients such as dimethicone, mineral oils, polydecenes, petrolatum, and combinations thereof. One example of a suitable emollient comprises PPG-15 stearyl ether. Other examples of suitable emollients include dipropylene glycol and propylene glycol.

Deodorant Actives

Suitable deodorant actives can include any topical material that is known or otherwise effective in preventing or eliminating malodor associated with perspiration. Suitable deodorant actives may be selected from the group consisting of antimicrobial agents (e.g., bacteriocides, fungicides), malodor-absorbing material, and combinations thereof. For example, antimicrobial agents may comprise cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichloro-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof. The concentration of the optional deodorant active may range from about 0.001%, from about 0.01%, of from about 0.1%, by weight of the composition to about 20%, to about 10%, to about 5%, or to about 1%, by weight of the composition.

Odor Entrappers

The composition can include an odor entrapper. Suitable odor entrappers for use herein include, for example, solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Cyclodextrin molecules are described in U.S. Pat. Nos. 5,714,137, and 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition.

Buffering Agent

The composition can include a buffering agent which may be alkaline, acidic or neutral. The buffer can be used in the composition for maintaining the desired pH. The composition may have a pH from about 3 to about 10, from about 4 to about 9, from about 5 to about 8, from about 6 to about 7, or it may have a pH of about 6.5. One unique feature of the polyvinyl amine malodor control polymers is its ability to maintain active nitrogen sites at high pH levels which can help enhance the antibacterial effect which comes, at least in part, from the nitrogen sites.

Suitable buffering agents include, for example, hydrochloric acid, sodium hydroxide, potassium hydroxide, and combinations thereof.

The compositions can contain at least about 0%, alternatively at least about 0.001%, alternatively at least about 0.01%, by weight of the composition, of a buffering agent. The composition may also contain no more than about 1%, alternatively no more than about 0.75%, alternatively no more than about 0.5%, by weight of the composition, of a buffering agent.

Solubilizer

The composition can contain a solubilizer. A suitable solubilizer can be, for example, a surfactant, such as a no-foaming or low-foaming surfactant. Suitable surfactants are nonionic surfactants, cationic surfactants, amphoteric surfactants, zwitterionic surfactants, and mixtures thereof.

Suitable solubilizers include, for example, hydrogenated castor oil, polyoxyethylene 2 stearyl ether, polyoxyethylene 20 stearyl ether, and combinations thereof. One suitable hydrogenated castor oil that may be used in the present composition is polyoxyethylene hydrogenated castor oil.

When the solubilizing agent is present, it is typically present at a level of from about 0.01% to about 5%, alternatively from about 0.01% to about 3%, alternatively from about 0.05% to about 1%, alternatively from about 0.01% to about 0.05%, by weight of the composition.

Preservatives

The composition can include a preservative. The preservative is included in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase shelf-life.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hills America; formal-dehyde; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative can range from about 0.0001% to about 0.5%, alternatively from about 0.0002% to about 0.2%, alternatively from about 0.0003% to about 0.1%, by weight of the composition.

B. Body Spray

A body spray can contain, for example, a carrier, perfume, a deodorant active, odor entrappers, propellant, or combinations thereof. The body spray compositions can be applied as a liquid.

Carrier

A carrier suitable for use in a body spray can include, water, alcohol, or combinations thereof. The carrier may be present in an amount of about 1% to about 99.5%, about 25% to about 99.5%, about 50% to about 99.5%, about 75% to about 99.5% about 80% to about 99.5%, from about 15% to about 45%, or any combination of the end points and points encompassed within the ranges, by weight of the composition. A suitable example of an alcohol can include ethanol.

Propellant

The compositions described herein can include a propellant. Some examples of propellants include compressed air, nitrogen, inert gases, carbon dioxide, and mixtures thereof. Propellants may also include gaseous hydrocarbons like propane, n-butane, isobutene, cyclopropane, and mixtures thereof. Halogenated hydrocarbons like 1,1-difluoroethane may also be used as propellants. Some non-limiting examples of propellants include 1,1,1,2,2-pentafluoroethane, 1,1,1,2-tetrafluoroethane, 1,1,1,2,3,3,3-heptafluoropropane, trans-1,3,3,3-tetrafluoroprop-1-ene, dimethyl ether, dichlorodifluoromethane (propellant 12), 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Some other propellants suitable for use include, but are not limited to, A-46 (a mixture of isobutane, butane and propane), A-31 (isobutane), A-17 (n-butane), A-108 (propane), AP70 (a mixture of propane, isobutane and n-butane), AP40 (a mixture of propane, isobutene and n-butane), AP30 (a mixture of propane, isobutane and n-butane), and 152A (1,1 diflouroethane). The propellant may have a concentration from about 15%, 25%, 30%, 32%, 34%, 35%, 36%, 38%, 40%, or 42% to about 70%, 65%, 60%, 54%, 52%, 50%, 48%, 46%, 44%, or 42%, or any combination thereof, by weight of the total fill of materials stored within the container.

C. Invisible Solid

Invisible solid antiperspirant compositions as described herein can contain a primary structurant, an antiperspirant active, a perfume, and additional chassis ingredient(s). The antiperspirant composition can further comprise other optional ingredient(s). The compositions can be in the form of a solid stick. The compositions can have a product hardness of about 600 gram force or more. The compositions may be free of dipropylene glycol, added water, castor wax, or any combination thereof. The antiperspirant composition may be anhydrous. The antiperspirant composition may be free of added water.

Hardness

The invisible solid can have a product hardness of least about 600 gram·force, more specifically from about 600 gram·force to about 5,000 gram·force, still more specifically from about 750 gram·force to about 2,000 gram·force, and yet more specifically from about 800 gram·force to about 1,400 gram·force.

The term "product hardness" or "hardness" as used herein is a reflection of how much force is required to move a penetration cone a specified distance and at a controlled rate into an antiperspirant composition under the test conditions described herein below. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45-degree angle penetration cone through the composition for a distance of 10 mm at a speed of 2 mm/second. The standard cone is available from Texture Technology Corp., as part number TA-15, and has a total cone length of about 24.7 mm, angled cone length of about 18.3 mm, and a maximum diameter of the angled surface of the cone of about 15.5 mm. The cone is a smooth, stainless steel construction and weighs about 17.8 grams.

Primary Structurants

The invisible solid can comprise a suitable concentration of a primary structurant to help provide the antiperspirant with the desired viscosity, rheology, texture and/or product hardness, or to otherwise help suspend any dispersed solids or liquids within the composition.

The term "solid structurant" as used herein means any material known or otherwise effective in providing suspending, gelling, viscosifying, solidifying, and/or thickening properties to the composition or which otherwise provide structure to the final product form. These solid structurants include gelling agents, and polymeric or non-polymeric or inorganic thickening or viscosifying agents. Such materials will typically be solids under ambient conditions and include organic solids, crystalline or other gellants, inorganic particulates such as clays or silicas, or combinations thereof.

The concentration and type of solid structurant selected for use in the antiperspirant compositions will vary depending upon the desired product hardness, rheology, and/or other related product characteristics. For most structurants suitable for use herein, the total structurant concentration ranges from about 5% to about 35%, more typically from about 10% to about 30%, or from about 7% to about 20%, by weight of the composition.

Non-limiting examples of suitable primary structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, baysberry, synthetic waxes such as Fischer-Tropsch waxes, and microcrystalline wax; polyethylenes with molecular weight of 200 to 1000 daltons; solid triglycerides; behenyl alcohol, or combinations thereof.

Other non-limiting examples of primary structurants suitable for use herein are described in U.S. Pat. Nos. 5,976,514 and 5,891,424, the descriptions of which are incorporated herein by reference.

Antiperspirant Active

The antiperspirant stick compositions can comprise a particulate antiperspirant active suitable for application to human skin. The concentration of antiperspirant active in the composition should be sufficient to provide the desired perspiration wetness and odor control from the antiperspirant stick formulation selected.

The antiperspirant stick compositions can comprise an antiperspirant active at concentrations of from about 0.5% to about 60%, and more specifically from about 5% to about 35%, by weight of the composition. These weight percentages are calculated on an anhydrous metal salt basis exclusive of water and any complexing agents such as, for example, glycine, and glycine salts. The antiperspirant active as formulated in the composition can be in the form of dispersed particulate solids having an average particle size or equivalent diameter of less than about 100 microns, more specifically less than about 20 microns, and even more specifically less than about 10 microns.

The antiperspirant active for use in the anhydrous antiperspirant compositions of the present invention can include any compound, composition or other material having antiperspirant activity. More specifically, the antiperspirant actives may include astringent metallic salts, especially inorganic and organic salts of aluminum, zirconium and zinc, as well as mixtures thereof. Even more specifically, the antiperspirant actives may include aluminum-containing and/or zirconium-containing salts or materials, such as, for example, aluminum halides, aluminum chlorohydrate, aluminum hydroxyhalides, zirconyl oxyhalides, zirconyl hydroxyhalides, and mixtures thereof.

Aluminum salts for use in the anhydrous antiperspirant stick compositions include those that conform to the formula:

$$Al_2(OH)_aCl_b \cdot xH_2O,$$

wherein a is from about 2 to about 5;
the sum of a and b is about 6;
x is from about 1 to about 6; and
a, b, and x may have non-integer values.

More specifically, aluminum chlorohydroxides referred to as "5/6 basic chlorohydroxide" can be used, wherein a=5, and "2/3 basic chlorohydroxide", wherein a=4.

Processes for preparing aluminum salts are disclosed in U.S. Pat. Nos. 3,887,692; 3,904,741; 4,359,456; and British Patent Specification 2,048,229, the disclosures of which are incorporated herein by reference for the purpose of describing processes for preparing aluminum salts.

Mixtures of aluminum salts are described in British Patent Specification 1,347,950, which description is also incorporated herein by reference.

Zirconium salts for use in the anhydrous antiperspirant stick compositions include those which conform to the formula:

$$ZrO(OH)_{2-a}Cl_a \cdot xH_2O,$$

wherein a is from about 1.5 to about 1.87;
x is from about 1 to about 7; and
a and x may both have non-integer values.

These zirconium salts are described in Belgian Patent 825,146, Schmitz, issued Aug. 4, 1975, which description is incorporated herein by reference. Zirconium salts that additionally contain aluminum and glycine, commonly known as "ZAG complexes," are believed to be especially beneficial. These ZAG complexes contain aluminum chlorohydroxide and zirconyl hydroxy chloride conforming to the above-described formulas. Such ZAG complexes are described in U.S. Pat. No. 3,792,068; Great Britain Patent Application 2,144,992; and U.S. Pat. No. 4,120,948, disclosures of which are incorporated herein by reference for the limited purpose of describing ZAG complexes.

Also suitable for use herein are enhanced efficacy aluminum-zirconium chlorohydrex-amino acid which typically has the empirical formula $Al_nZr(OH)_{[3n+4-m(n+1)]}(Cl)_{[m(n+1)]}-AA_q$ where n is 2.0 to 10.0, preferably 3.0 to 8.0; m is about 0.48 to about 1.11 (which corresponds to M:Cl approximately equal to 2.1-0.9), preferably about 0.56 to about 0.83 (which corresponds to M:Cl approximately equal to 1.8-1.2); q is about 0.8 to about 4.0, preferably about 1.0 to 2.0; and AA is an amino acid such as glycine, alanine, valine, serine, leucine, isoleucine, β-alanine, cysteine, β-amino-n-butyric acid, or γ-amino-n-butyric acid, preferably glycine. These salts also generally have some water of hydration associated with them, typically on the order of 1 to 5 moles per mole of salt (typically, about 1% to about 16%, more typically about 4% to about 13% by weight). These salts are generally referred to as aluminum-zirconium trichlorohydrex or tetrachlorohydrex when the Al:Zr ratio is between 2 and 6 and as aluminum-zirconium pentachlorohydrex or octachlorohydrex when the Al:Zr ratio is between 6 and 10. The term "aluminum-zirconium chlorohydrex" is intended to embrace all of these forms. The preferred aluminum-zirconium salt is aluminum-zirconium chlorohydrex-glycine. Additional examples of suitable high efficacy antiperspirant actives can include Aluminum Zirconium Pentachlorohydrex Glycine, Aluminum Zirconium Octachlorohydrex Glycine, or a combination thereof. These high efficacy actives are more fully described in U.S. App. Pub. No. 2007/0003499 by Shen et al. filed Jun. 30, 2005.

There may be some antiperspirants and/or deodorant embodiments that are substantially free of or completely free of aluminum.

Additional Chassis Ingredients
Additional Structurant

The antiperspirant composition can further comprise an additional structurant. The additional structurant may be present in an amount from 1% to about 10%, by weight of the composition. The additional structurant(s) will likely be present at an amount less than the primary structurant.

Non-limiting examples of suitable additional structurants include stearyl alcohol and other fatty alcohols; hydrogenated castor wax (e.g., Castorwax MP80, Castor Wax, etc.); hydrocarbon waxes include paraffin wax, beeswax, carnauba, candelilla, spermaceti wax, ozokerite, ceresin, bayberry, synthetic waxes such as Fisher-Tropsch waxes, and microcrystalline wax; polyethylenes with molecular weight of 200 to 1000 daltons; and solid triglycerides; behenyl alcohol, or combinations thereof.

Other non-limiting examples of additional structurants suitable for use herein are described in U.S. Pat. Nos. 5,976,514 and 5,891,424.

Solvent

The antiperspirant composition can comprise a solvent at concentrations ranging from about 20% to about 80%, and more specifically from about 30% to about 70%, by weight of the composition. The solvent can be a volatile silicone which may be cyclic or linear.

"Volatile silicone" as used herein refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976), which descriptions are incorporated herein by reference.

The volatile silicone can be a cyclic silicone having from 3 to 7, and more specifically from 5 to 6, silicon atoms, and still more specifically 5, like cyclopentasiloxane. These cyclic silicone materials will generally have viscosities of less than about 10 centistokes at 25° C.

Linear volatile silicone materials suitable for use in the antiperspirant compositions include those represented by the formula:

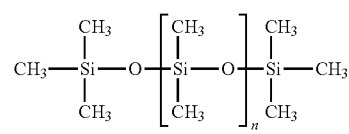

wherein n is from 1 to 7, and more specifically from 2 to 3. These linear silicone materials will generally have viscosities of less than about 5 centistokes at 25° C.

Specific examples of volatile silicone solvents suitable for use in the antiperspirant compositions include, but are not limited to, Cyclomethicone D-5; GE 7207 and GE 7158 (commercially available from General Electric Co.); Dow Corning 344; Dow Corning 345; Dow Corning 200; and DC1184 (commercially available from Dow Corning Corp.); and SWS-03314 (commercially available from SWS Silicones).

Non-Volatile Organic Fluids

Non-volatile organic fluids may be present, for example, in an amount of about 15% or less, by weight of the composition.

Non-limiting examples of nonvolatile organic fluids include mineral oil, PPG-14 butyl ether, isopropyl myristate, petrolatum, butyl stearate, cetyl octanoate, butyl myristate, myristyl myristate, C12-15 alkylbenzoate (e.g., Finsolv™), octyldodecanol, isostearyl isostearate, octododecyl benzoate, isostearyl lactate, isostearyl palmitate, and isobutyl stearate.

Other Optional Ingredients

The anhydrous antiperspirant compositions can further comprise any optional material that is known for use in antiperspirant and deodorant compositions or other personal care compositions or products, or which is otherwise suitable for topical application to human skin.

One example of optional materials are clay mineral powders such as talc, mica, sericite, silica, magnesium silicate, synthetic fluorphlogopite, calcium silicate, aluminum silicate, bentonite and montomorillonite; pearl pigments such as alumina, barium sulfate, calcium secondary phosphate, calcium carbonate, titanium oxide, finely divided titanium oxide, zirconium oxide, zinc oxide, hydroxy apatite, iron oxide, iron titrate, ultramarine blue, Prussian blue, chromium oxide, chromium hydroxide, cobalt oxide, cobalt titanate, titanium oxide coated mica; organic powders such as polyester, polyethylene, polystyrene, methyl methacrylate resin, cellulose, 12-nylon, 6-nylon, styrene-acrylic acid copolymers, poly propylene, vinyl chloride polymer, tetrafluoroethylene polymer, boron nitride, fish scale guanine, laked tar color dyes, laked natural color dyes; and combinations thereof.

Talc, if used at higher levels can produce a significant amount of white residue which has been found to be a consumer negative for product acceptance. Therefore it is best to limit the composition to less than 10%, less than about 8%, less than about 6%, or less than about 3%, by weight of the composition.

Nonlimiting examples of other optional materials include emulsifiers, distributing agents, antimicrobials, pharmaceutical or other topical active, preservatives, surfactants, and so forth. Examples of such optional materials are described in U.S. Pat. Nos. 4,049,792; 5,019,375; and 5,429,816; which descriptions are incorporated herein by reference.

D. Soft Solid

Soft solid composition can comprise volatile silicone, antiperspirant active, gellant, residue masking material, or combinations thereof. In addition, soft solids generally have a hardness value after dispensing of about 500 gram force or less.

Volatile Silicone Solvent

The soft solid can comprises a volatile silicone solvent at concentrations ranging from about 20% to about 80%, preferably from about 30% to about 70%, more preferably from about 45% to about 70%, by weight of the composition. The volatile silicone of the solvent may be cyclic or linear.

"Volatile silicone" as used herein refers to those silicone materials which have measurable vapor pressure under ambient conditions. Nonlimiting examples of suitable volatile silicones are described in Todd et al., "Volatile Silicone Fluids for Cosmetics", Cosmetics and Toiletries, 91:27-32 (1976), which descriptions are incorporated herein by reference. Preferred volatile silicone materials are those having from about 3 to about 7, preferably from about 4 to about 5, silicon atoms.

Cyclic volatile silicones are preferred for use in the antiperspirant compositions herein, and include those represented by the formula:

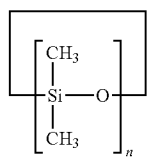

wherein n is from about 3 to about 7, preferably from about 4 to about 5, most preferably 5. These cyclic silicone materials will generally have viscosities of less than about 10 centistokes at 25° C.

Linear volatile silicone materials suitable for use in the antiperspirant compositions include those represented by the formula:

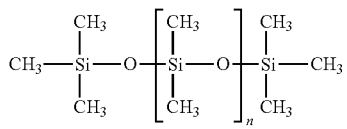

wherein n is from about 1 to about 7, preferably from about 2 to about 3. These linear silicone materials will generally have viscosities of less than about 5 centistokes at 25° C.

Specific examples of volatile silicone solvents suitable for use in the antiperspirant compositions include, but are not limited to, Cyclomethicone D-5 (commercially available from G. E. Silicones), Dow Corning 344, Dow Corning 345 and Dow Corning 200 (commercially available from Dow Corning Corp.), GE 7207 and 7158 (commercially available from General Electric Co.) and SWS-03314 (commercially available from SWS Silicones Corp.).

Gellant Material

The soft solid can include a gellant material comprising fatty alcohols having from about 20 to about 60 carbon atoms, or combinations thereof, at concentrations ranging from about 0.1% to about 8% by weight of the composition. The gellant material, when combined with the volatile silicone solvent described hereinbefore, provides the composition with a physically stable structure within which the particulate antiperspirant materials are dispersed, and maintained as such over an extended period of time.

Specifically, the gellant material can comprise saturated or unsaturated, substituted or unsubstituted, fatty alcohols or mixtures of fatty alcohols having from about 20 to about 60 carbons atoms, preferably from about 20 to about 40 carbon atoms. Preferred are combinations of the fatty alcohols. The fatty alcohol gellants are preferably saturated, unsubstituted monohydric alcohols or combinations thereof, which have a melting point of at less than about 110° C., more preferably from about 60° to about 110° C., even more preferably between about 100° C. and 110° C.

It has been found that this fatty alcohol-based gellant material, when combined with volatile silicone solvents provides a stable structure for maintaining a dispersion of particulate antiperspirant material in a topical formulation without the necessity of using conventional particulate thickening agents. This gellant material is especially useful in maintaining the physical stability of particulate dispersions containing higher concentrations of volatile silicone solvents.

It was also found that penetration force values for the antiperspirant compositions can be controlled by adjusting total fatty alcohol concentrations. In controlling penetration force values in this manner, there is no longer a need to use organic solvents or thickening agents to control penetration force values, which solvents or thickening agents often add cost to the formulation, introduce additional compatibility issues, and often contribute undesirable cosmetics such as prolonged stickiness, difficulty in ease of spreading, increased dry-down times and reduced dry feel after application.

Specific concentrations of the gellant materials can be selected according to the desired penetration force value. For roll-on formulations having a penetration force value of from about 20 gram·force to about 100 gram·force, gellant material concentrations preferably range from about 0.1% to about 3%, preferably from about 1.5% to about 3%, by weight of the antiperspirant composition. For other cream formulations, including those formulations suitable for use in cream applicator devices, which have a penetration force value of from about 100 gram·force to about 500 gram·force, gellant material concentrations preferably range from about 3% to about 8%, preferably from about 3% to about 6%, by weight of the antiperspirant composition.

Specific examples of fatty alcohol gellants for use in the antiperspirant compositions that are commercially available include, but are not limited to, Unilin® 425, Unilin® 350, Unilin®550 and Unilin® 700 (supplied by Petrolite)

Residue Masking Material

The soft solid compositions can further comprise a non-volatile emollient as a residue masking material. Such materials and their use in antiperspirant products are well known in the antiperspirant art, and any such material may be incorporated into the composition of the present invention, provided that such optional material is compatible with the essential elements of the composition, or does not unduly impair product performance or cosmetics.

Concentrations of the optional residue masking material can range from about 0.1% to about 40%, preferably from about 1% to about 10%, by weight of the antiperspirant composition. These optional materials can be liquid at ambient temperatures, and can be nonvolatile. The term "nonvolatile" as used in this context refers to materials which have a boiling point under atmospheric pressure of at least about 200° C. Nonlimiting examples of suitable residue masking materials for use in the antiperspirant products include butyl stearate, diisopropyl adipate, petrolatum, non-volatile silicones, octyldodecanol, phenyl trimethicone, isopropyl myristate, C12-15 ethanol benzoates and PPG-14 Butyl Ether. Residue masking materials are described, for example, in U.S. Pat. No. 4,985,238, which description is incorporated herein by reference.

Other Materials

The soft solid compositions can further comprise one, or more, other materials which modify the physical characteristics of the compositions or serve as additional "active" components when deposited on the skin. Many such materials are known in the antiperspirant art and can be used in the antiperspirant compositions herein, provided that such optional materials are compatible with the essential materials described herein, or do not otherwise unduly impair product performance.

Non limiting examples of materials can include active components such as bacteriostats and fungiostats, and "non-active" components such as colorants, perfumes, cosmetic powders, emulsifiers, chelants, distributing agents, preservatives, and wash-off aids. Examples of such optional materials are described in U.S. Pat. No. 4,049,792; Canadian Patent 1,164,347; U.S. Pat. Nos. 5,019,375; and 5,429,816; which descriptions are incorporated herein by reference.

E. Aerosol

An aerosol composition can comprise a concentrate, a propellant, or a combination thereof. Alcohol is a predominant component of the concentrates provided herein. Useful alcohols include $C_1$-$C_3$ alcohols, with the preferred alcohol being ethanol. In certain examples, the alcohol is employed at a concentration level of from at least about 40%, 50% or 55% to about 80%, by weight of the concentrate.

An antiperspirant active is dissolved in the alcohol, at a level of from about 1% to about 15%, by weight of the concentrate. Various antiperspirant actives can be employed, including, for example, aluminum chloride, aluminum chlorohydrate, aluminum chlorohydrex, aluminum chlorohydrex PG, aluminum chlorohydrex PEG, aluminum dichlorohydrate, aluminum dichlorohydrex PG, aluminum dichlorohydrex PEG, aluminum sesquichlorohydrate, aluminum sesquichlorohydrex PG, aluminum sesquichlorohydrex PEG, aluminum sulfate, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium trichlorohydrate, aluminum zirconium tetrachlorohydrate GLY, and aluminum zirconium trichlorohydrate GLY. In one example, aluminum chlorohydrex PG is the chosen antiperspirant active.

The antiperspirant concentrates can also include an oil or a mixture of two or more oils. Useful oils include, for example, volatile silicone oils and non-volatile organic oils. "Volatile silicone", as used herein, refers to those silicone materials that have measurable vapor pressure under ambient conditions. Non-limiting examples of suitable volatile silicones are described in Todd et al., "Volatile Silicone Fluids for Cosmetics", Cosmetics and Toiletries, 91:27-32 (1976). The volatile silicone can be a cyclic silicone having from at least about 3 silicone atoms or from at least about 5 silicone atoms but no more than about 7 silicone atoms or no more than about 6 silicone atoms. For example, volatile silicones can be used which conform to the formula:

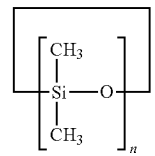

wherein n is from about 3 or from about 5 but no more than about 7 or no more than about 6. These volatile cyclic silicones generally have a viscosity of less than about 10 centistokes at 25° C. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.). SWS-03314, SWS-03400, F-222, F-223, F-250, F-251 (available from SWS Silicones Corp.); Volatile Silicones 7158, 7207, 7349 (available from Union Carbide); MASIL SF-V (available from Mazer) and combinations thereof. Suitable volatile silicone oils can also include linear silicone oils such as, for example, DC200 (1 cSt), DC200 (0.65 cSt), and DC2-1184, all of which are available from Dow Corning Corp. In certain examples, the volatile silicone oil can have a viscosity of less than 10 centistokes at 25° C.

Non-volatile organic, emollient oils can also be employed. A representative, non-limiting list of emollient oils includes CETIOL CC (dicaprylyl carbonate), CETIOL OE (dicaprylyl ether), CETIOL S (diethylhexylcyclohexane), and CETIOL B (dibutyl adipate), all of which are available from Cognis, and LEXFEEL 7 (neopentyl glycol diheptanoate) from Inolex. In certain examples, the organic emollient oils have a viscosity of less than 50 centistokes at 25° C. The term "organic emollient oil" as used herein means silicon-free emollient oils that are liquid at 25° C., and that are safe and light to skin and can be miscible with volatile silicone oils (as described above) and the antiperspirant active-alcohol solution in the concentration ranges described below.

The oil or mixture of oils is generally included in the concentrate formulas at a level of from about 5% to about 45%, by weight of the concentrate. This viscosity ranges noted above in connection with the different classes of oil can facilitate desired spray rates and patterns, and can help minimize nozzle clogging. To provide desired skin feel, minimal nozzle clogging, and good concentrate stability, the ratio of alcohol to volatile silicone oil is preferably greater than 1.0, 1.35, or 1.5. And in examples having both a volatile silicone oil and an organic emollient oil, the ratio of alcohol to total oil is preferably greater than or equal to about 0.90. The oils in certain examples are miscible with the alcohol and antiperspirant active solution. Although various levels of miscibility are acceptable, the oils are preferably miscible enough with the alcohol and antiperspirant active solution to yield a concentrate having a clear appearance.

The antiperspirant compositions can also include residue-masking agents and propellants as discussed above.

In the present invention, a personal care composition may comprise at least one nucleic acid aptamer; wherein said at least one nucleic acid aptamer has a binding affinity for a compound selected from the group consisting of: dimethyl sulfide, dimethyl disulfide, methanethiol; (E)-3-methyl-2-hexenoic acid, 3-methyl-3-hydroxy hexanoic acid, 3-methyl-3-sulfanylhexan-1-ol, 3-sulfanylhexan-1-ol, 2-nonenal, 4-hydroxy-2-nonenal, diacetyl (2,3-butanedione), isovaleric acid, butanoic acid, acetic acid, propanoic acid, butyric acid, other 3-methyl carboxylic acids, and mixtures thereof. In another embodiment of the present invention, said at least one nucleic acid aptamer has a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof. In yet another embodiment, said at least one nucleic acid aptamer has a binding affinity for 3-methyl-3-sulfanylhexan-1-ol.

In the present invention, a method of decreasing underarm odor may comprise administering a personal care composition to the underarm area; wherein said personal care composition comprises at least one nucleic acid aptamer that has a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, 2-nonenal, diacetyl (2,3-butanedione), isovaleric acid, butanoic acid, acetic acid, propanoic acid, butyric acid, other 3-methyl carboxylic acids, and mixtures thereof. In another embodiment of the present invention, said at least one nucleic acid aptamer has a binding affinity for a compound selected from the group consisting of: (E)-3-methyl-2-hexenoic acid, 3-methyl-3-hydroxy hexanoic acid, 3-methyl-3-sulfanylhexan-1-ol, 3-sulfanylhexan-1-ol, and mixtures thereof.

V. Application of Aptamer Compositions in Other Consumer Product Applications The aptamers of the current invention can be used in consumer product compositions to provide one or more benefits. In certain aspects of the present invention, a consumer product composition comprises at least one nucleic acid aptamer; preferably wherein said at least one nucleic acid aptamer has a binding affinity for a compound selected from the group consisting of: 3-methyl-3-sulfanylhexan-1-ol, 3-sulfanylhexan-1-ol, methanethiol, dimethyl sulfide, dimethyl disulfide, dimethyl trisulfide, hydrogen sulfide, carbon disulfide, 3-methylthio-propanal, dimethyl sulfone; (E)-3-methyl-2-hexenoic acid, 3-methyl-3-hydroxy hexanoic acid, nonanoic acid, octanoic acid, 4-ethyloctanoic acid, heptanoic acid, hexanoic acid, 2-ethylhexanoic acid, pentanoic acid, isovaleric acid, butyric acid, 3-methyl butanoic acid, propanoic acid, acetic acid, formic acid, other 3-methyl carboxylic acids, other carboxylic acids; methyl acetate, ethyl acetate, benzyl acetate, ethyl butanoate, octyl formate, 2-ethylhexyl-salicylate, γ-nonalactone, other esters of carboxylic acids; ammonia, methylamine, ethylamine, trimethylamine, pyrazine, pyridine, 2-methylpyridine, 2-ethylpyridine, 2,3,5-trimethylpyridine, pyrrole, 1-methyl pyrrole, acetonitrile, N,N-dimethylformamide, 1-(2-aminophenyl) ethenone, 4-morpholine ethanamine, 4-cyanocyclohexene, indole, 3-methyl indole, propanal, 1,2-methyl propanal, butanal, 2-methyl butanal, 3-methyl butanal, pentanal, (E)-2-pentenal, hexanal, (E)-2-hexenal, heptanal, octanal, (E)-2-octenal, nonanal, 2-nonenal, decanal, 2,6-nonadienal, undecanal, dodecanal, tridecanal, benzaldehyde, other aldehydes; diacetyl (2,3-butanedione); 2-methoxyphenol, propanone, butanone, pentan-2-one, pentan-3-one, cyclopentanone, hexan-2-one, cyclohexanone, heptan-2-one, heptan-3-one, oct-1-en-3-one, 2,3-octadione, nonan-2-one, androstenone, 1-phenyl-ethanone, acetophenone, furan, 2-methylfuran, 3-methylfuran, 2,5-diethylfuran, ethanol, 2-ethoxyethanol, 2-butoxyethanol, propan-2-ol, 2-methyl-1-propanol, butanol, 3-methyl-1-butanol, pentan-1-ol, pentan-2-ol, hexan-1-ol, oct-1-en-3-ol, 2-butyl-1-octanol, nonan-1-ol, decan-1-ol, cyclodecanol, undecane-1-ol, 2-heptadecanol, benzyl alcohol, 2-phenylethanol, furfuryl alcohol, other alcohols; isoprene, pentane, cyclopentane, hexane, cyclohexane, heptane, octane, octa-1-ene, octa-2,4-diene, nonane, decane, tridecane, tetradecane, hexadecane, octadecane, nonadecane, eicosane, methylbenzene, 1-methyl-4-(1-methylethyl)benzene, naphthalene, other hydrocarbons; dichloromethane, 1,1,1-trichloroethane, chlorobenzene, 1,4-dichlorobenze, other chlorinated hydrocarbons; diphenyl ether, other ethers; and mixtures thereof; and more preferably wherein said at least one nucleic acid aptamer has a binding affinity for a compound selected from the group consisting of: dimethyl sulfide, dimethyl disulfide, methanethiol; (E)-3-methyl-2-hexenoic acid, 3-methyl-3-hydroxy hexanoic acid, 3-methyl-3-sulfanylhexan-1-ol, 3-sulfanylhexan-1-ol, 2-nonenal, 4-hydroxy-2-nonenal, diacetyl (2,3-butanedione), isovaleric acid, butanoic acid, acetic acid, propanoic acid, butyric acid, other 3-methyl carboxylic acids, and mixtures thereof.

In another embodiment, the consumer product composition is selected from the group comprising: compositions for treating fabrics, hard surfaces and any other surfaces in the area of fabric and home care, including air care, car care, dishwashing, fabric conditioning (including softening), fabric freshening, laundry detergents, laundry and rinse additive and/or care, hard surface cleaning and/or treatment, and other cleaning for consumer or institutional use; personal cleansing compositions; compositions for treating hair (human, dog, and/or cat), including bleaching, coloring, dyeing, conditioning, growing, removing, retarding growth, shampooing, and styling; products relating to treating skin (human, dog, and/or cat), including creams, lotions, ointments, and other topically applied products for consumer use; body sprays; fine fragrances such as colognes and perfumes; products relating to disposable absorbent and/or non-absorbent articles including adult incontinence garments, bibs, diapers, training pants, infant and toddler care wipes; hand soaps; products relating to oral care compositions including toothpastes, tooth gels, mouth rinses, denture adhesives, and tooth whitening; personal health care medications; products relating to grooming including shave care compositions and composition for coating, or incorporation into, razors or other shaving devices; and compositions for coating, or incorporation into, wet or dry bath tissue, facial tissue, disposable handkerchiefs, disposable towels and/or wipes, incontinence pads, panty liners, sanitary napkins, and tampons and tampon applicators; and combinations thereof.

In another embodiment, the consumer product composition of the present invention comprises a surfactant and a nucleic acid aptamer as described herein. The consumer product compositions of the present invention may comprise greater than about 0.1% by weight of a surfactant or mixture of surfactants. Surfactant levels cited herein are on a 100% active basis, even though common raw materials such as sodium lauryl sulphate may be supplied as aqueous solutions of lower activity. Suitable surfactant levels are from about 0.1% to about 25%, from about 0.25% to about 10%, or from about 0.5% to about 5% by weight of the total composition. Suitable surfactants for use herein include anionic surfactants, amphoteric surfactants, nonionic surfactants, zwitterionic surfactants, cationic surfactants, and mixtures thereof, though anionic, amphoteric, nonionic and zwitterionic surfactants (and mixtures thereof) are preferred.

VI. Examples

Examples 1-3. Clear Gel Antiperspirant/Deodorant Compositions

Examples 1-3 below are clear gel antiperspirant/deodorant compositions with an inventive aptamer.

| RMS/GCAS # | Common/Trade name | Ex. 1 - Formula % | Ex. 2 - Formula % | Ex. 3 - Formula % |
| --- | --- | --- | --- | --- |
| 98846025 | Aluminum Zirconium and Water Premx | 55 | 0 | 0 |
| 10032106 | Bottled Water | QS | QS | QS |
| 95596037s | Ethanol 200 Proof | 12 | 5 | 12 |
| | Aptamer- SEQ ID NO: 1 | 0.1-0.01% | 0.1-0.01% | 0.1-0.01% |
| 10048070 | Sodium Chloride | 0 | 3 | 0 |
| 10200013 95595978 | Cyclopentasiloxane & PEG/PPG-18/18 DIMET | 8 | 0 | 8 |
| 10047959 11100297 | Cyclopentasiloxane | 3 | 0 | 7 |
| 10045439 | Dipropylene Glycol | 8 | 20 | 20 |
| 10047976 | Dimethicone 10 cst | 6 | 8 | 14 |
| 10045441s | Dimethicone 50 cst | 0 | 6 | 0 |
| 1285637 | Dimethicone (and) PEG/PPG-18/18 Dimethicone (Dowsil ES-5227) | 0 | 5 | 5 |
| 96404738s | Perfume | | 0.75 | 0.75 |
| | Total | | 100 | 100 |

Examples 4-7. Soft Solid Antiperspirant/Deodorant Compositions

Examples 4-7 below are soft solid antiperspirant/deodorant compositions with an inventive aptamer.

| Common/Trade name | Ex. 4: Soft Solid made via batch process - Formula % | Ex. 5: Invisible Solid made via batch process - Formula % | Ex. 6: Invisible Solid made via Split Stream - Formula % | Ex. 7: Invisible Solid made via batch process - Formula % |
| --- | --- | --- | --- | --- |
| Aluminum Zirconium Trichlorohydrex Glycine Powder | 26.5 | 24.0 | — | 0 |
| Aluminum Zirconium Tetrachlorohydrex Gly | — | — | 25.6 | 0 |
| Aptamer - SEQ ID NO: 1 | 0.1-0.01% | 0.1-0.01% | 0.1-0.01% | 0.1-0.01% |
| Cyclopentasiloxane | QS | QS | QS | 0 |
| 10 cs Dimethicone | 5 | 5 | 5 | 35 |

| Common/Trade name | Ex. 4: Soft Solid made via batch process - Formula % | Ex. 5: Invisible Solid made via batch process - Formula % | Ex. 6: Invisible Solid made via Split Stream - Formula % | Ex. 7: Invisible Solid made via batch process - Formula % |
|---|---|---|---|---|
| CO-1897 Stearyl Alcohol NF | — | 12.3 | 13.25 | 16 |
| Ozokerite Wax SP-1026 Type | — | 1.0 | 1.0 | 4 |
| Hydrogenated Castor Oil MP80 Deodorized | — | 2.75 | 2.90 | 0 |
| Behenyl Alcohol | — | 0.2 | 0.2 | 0.2 |
| Tribehenin | 4.5 | — | — | 0 |
| C18-36 acid triglyceride | 1.125 | — | — | 0 |
| C12-15 Alkyl Benzoate | — | 8.5 | 8.5 | 2 |
| Performathox 450 ethoxylate | 1.0 | 1.0 | 2.0 | 0 |
| PPG-14 Butyl Ether | 0.5 | 6.5 | 6.5 | 3 |
| White Petrolatum | 3 | 3 | 3 | 5 |
| Mineral Oil | — | 8.0 | 8.0 | 8 |
| Fragrance | 0.75 | 0.75 | 0.75 | 2.0 |
| Talc Imperial 250 USP | — | 3 | 2.5 | 6 |
| Fragrance Complexed Beta-cyclodextrin | 2.0 | 3.0 | — | 3 |
| Polyacrylate Microcapsule | 2.0 | — | 2.0 | 0 |
| Tapioca Starch | 1.0 | 0.8 | 1.5 | 15 |

Example 4-7 are prepared by a split stream process. In the hot stream tank, the waxes (stearyl alcohol, castor wax, ozokerite, behenyl alcohol), emollients (C12-15 Alkyl benzoate), performathox 450 ethoxylate and a lesser portion of the cyclopentasiloxane are added into one tank, mixed, and then heated to 88° C. to melt the waxes. In the cold stream tank, the powders (actives, talc, cyclodextrins, spray-dried microcapsules, starch delivery vehicle), fragrances, PPG-14 butyl ether, and a greater portion of the cyclopentasiloxane are added and mixed and maintained at a temperature of less than 50° C. Once each of the hot and cold streams each is relatively homogenous, each of the process streams are simultaneously fed into a static mixer where the two streams are combined for about 5 seconds or less, ensuring a homogenous personal care composition while minimizing the mix time above the wax crystallization temperature. The antiperspirant composition then exits the static mixer into individual canisters where the product is allowed to cool to room temperature. QS indicates that this material is used to bring the total to 100%.

Examples 8-9. Aerosol Antiperspirant/Deodorant Compositions

Examples 8 and 9 below are aerosol antiperspirant/deodorant compositions with an inventive aptamer.

| Common/Trade name | Ex. 8 - Formula % | Ex. 9 - Formula % |
|---|---|---|
| Aluminum ChloroHydrate | 29 | 29 |
| Aluminum Starch OctenylSuccinate | 10 | 10 |
| Aptamer - SEQ ID NO: 1 | 0.1-0.01% | 0.1-0.01% |
| Mineral Oil | 2 | 2 |
| C12-15 Alkyl Benzoate | 4 | 4 |
| PPG-14 Butyl Ether | 2 | 2 |
| Disteardimonium Hectorite | 2 | 2 |
| Cyclopentasiloxane | 33 | 0 |
| Dimethicone 5 cst | 0 | 33 |
| Dimethicone 50 cst | 4 | 4 |
| Dimethicone (and) Dimethiconol | 5 | 5 |
| Triethyl Citrate | 0.7 | 0.7 |
| Datura BCD | 8 | 8 |
| Total | 100 | 100 |

Examples 10-14. Natural Solid Antiperspirant/Deodorant Compositions

Examples 10-14 below are natural solid deodorant compositions with an inventive aptamer.

| | Ex. 10 - Formula % | Ex. 11 - Formula % | Ex. 12 - Formula % | Ex. 13 - Formula % | Ex. 14 - Formula % |
|---|---|---|---|---|---|
| Caprylic/Capric Triglyceride | 43.4 | 44.7 | 42.7 | 46.9 | 46.15 |
| Aptamer - SEQ ID NO: 1 | 0.1-0.01% | 0.1-0.01% | 0.1-0.01% | 0.1-0.01% | 0.1-0.01% |
| Arrowroot Powder | 19 | 23 | 23 | 19 | — |
| Stearyl Alcohol | 11.5 | 10.7 | 10.7 | — | — |
| Ozokerite | — | — | 1.5 | 11 | 11.75 |
| Castor Wax | 3 | 3 | 3 | — | — |

-continued

|  | Ex. 10 - Formula % | Ex. 11 - Formula % | Ex. 12 - Formula % | Ex. 13 - Formula % | Ex. 14 - Formula % |
|---|---|---|---|---|---|
| Baking Soda | 12 | 12 | 6 | 6 | — |
| Magnesium Hydroxide | — | — | 6 | 6 | 12.0 |
| Shea Butter | 2 | 2 | 2 | 2 | 2 |
| Coconut Oil | 4.5 | 4.5 | 4.5 | 4.5 | 4.5 |
| Perfumes | 0.6 | 0.6 | 0.6 | 0.6 | 0.6 |
| Cyclodextrin | 4 | — | — | 4 | 4 |
| Tapioca Starch | — | — | — | — | 19.0 |

Any of the examples herein may be made as one of ordinary skill in the art would understand.

Example 15. Aptamers Design

A. Aptamer Selection

A.1. Preparation of the Immobilization Field for FRELEX

An immobilization field was prepared by synthesizing a random library of eight nucleotides with a disulfide group on the 5'-end (immobilization field library) (IDT DNA). The library was dissolved at a concentration of 10 µM in 1×PBS buffer. The surface of a gold coated glass slide with dimensions of 7 mm×10 mm×0.3 mm was used. This surface was treated with five sequential 10 µL drops of the immobilization field library. The slide was then allowed to incubate for 1 hour in the dark and in the presence of humidity to complete the conjugation of the immobilization field library onto the gold surface. After this incubation period, the remaining solution was removed, and the surface was allowed to dry at room temperature.

The remaining surface was then blocked with short PEG molecules having the following general structure: $CH_3O$—$(CH_2CH_2O)_n$—$CH_2CH_2SH$ and an average molecular weight of 550 daltons. The PEG molecules were applied at a concentration of 286 µM in 1×PBS buffer and allowed to incubate overnight prior to removal. This process was repeated in a second blocking step with an incubation period of 30 minutes at room temperature. Following the blocking steps, the chip was washed with 1× HEPES buffer (10 mM HEPES, pH 7.4, 120 mM NaCl, 5 mM KCl, 5 mM $MgCl_2$) for 5 minutes while shaking at room temperature.

A.2. Library Preparation

A DNA library containing about 10 nmoles oligonucleotides was purchased from Trilink biotechnologies. The oligonucleotides were composed of a random region of 40 nucleotides flanked by two conserved regions, i.e. a 5' forward primer recognition sequence (5'-AGCGTCTCTC-GATCTCATTCTCA-3') SEQ ID NO 416 and a 3' reverse primer recognition sequence (5'- GTTGTTTTGATGGCCC-3') SEQ ID NO 417. The library was solubilized in 100 µL of $H_2O$ and split into aliquots of 16.6 µL (1.66 nmoles or $10^{15}$ different sequences). Each individual oligonucleotide in the library had the sequence 5'-AGCGTCTCTCGATCT-CATTCTCA($N_{40}$)GTTGTTTTGATGGCCC-3', or 5'-AGCGTCTCTCGATCTCATTCT-CANNNNNNNNNNNNNNNNNNNNNNNNNNNNNNNN NNNNNNNN GTTGTTTTGATGGCCC-3', wherein N is any deoxynucleotide (A, C, G, or T) SEQ ID NO 418. A schematic of the oligonucleotides in the library is illustrated in FIG. 2.

Before selection, a 16.6 µL-aliquot of the library was mixed with 5 µL of 10× citrate buffer (0.5 M citric acid/sodium citrate dihydrate, pH 5.5) and 23.4 µL of water. Then, the solution was heated to 85° C. for 10 min, followed by cooling in an iced 1 M NaCl bath for 15 min, followed by addition of 5 µL of 10× salt stock solution (4.66 M NaCl, 0.12 KCl, 0.041 M $CaCl_2$). Finally, the library was incubated at room temperature for 10 min before continuing with the selection process. FIG. 2 shows a schematic of the DNA library.

A.3. FRELEX Selection

FRELEX (WO 2017035666 A1) is a two-step aptamer selection process that does not require immobilization of the target. In the first step of FRELEX (negative selection), oligonucleotides within the library are selected for their ability to bind to the Immobilization Field (A.1). During this phase of selection, molecules for which the desired aptamers should have low affinity can be added. Aptamers binding to such molecules are inhibited from binding to the Immobilization Field and thus discarded.

In the second step of FRELEX (positive selection), oligonucleotides that have bound to the Immobilization Field during the negative selection are recovered and combined with the positive target. This mixture is then exposed to a fresh Immobilization Field. In this phase, oligonucleotides that do not bind to the Immobilization Field are retained, as those aptamers that bind to the positive target are inhibited from binding to this field. This process is repeated reiteratively.

Figure 3:
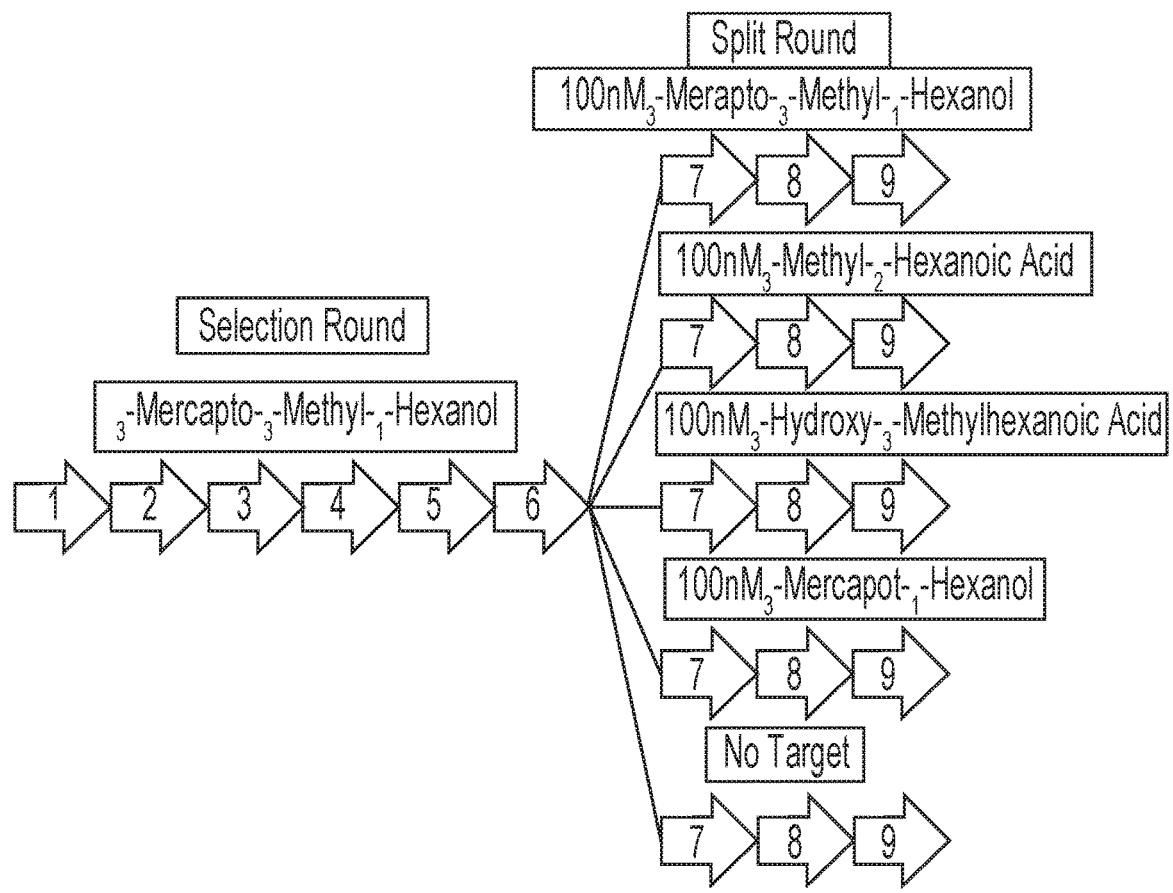
FIG. 3—Aptamer selection strategy.

An overview of the entire selection strategy used for this enablement of the invention is provided in FIG. 3. FRELEX as described herein was applied for selection for 3-mercapto-3-methyl-1-hexanol (target 1) for the first six selection rounds. Then, five aliquots of single stranded sense DNA were prepared from this selection library. Each aliquot was then assigned to a different target: 3-mercapto-3-methyl-1-hexanol (target 1 or primary target), 3-methyl-2-hexenoic acid (target 2), 3-hydroxy-3-methylhexanoic acid (target 3), 3-mercapto-1-hexanol (target 4), and a final split channel containing no target molecule. The library aliquots were exposed to their respective target at 100 nM using the FRELEX selection method described above. Three selection rounds were performed on the five split library aliquots. Each selection split is referred to as a channel, and libraries are maintained within a channel. That is, the selection round 7 library derived from selection against 3-mercapto-3-methyl-1-hexanol was used for selection round 8 only against the same target. FIG. 3 shows the aptamer selection strategy.

For the negative selection steps, the single stranded DNA library was added to the Immobilization Field and incubated at room temperature for 30 min and with gentle shaking (50 rpm). The unbound DNA was removed from the chip surface and discarded. Then, the chip was washed twice with 50 µL of 10× TE buffer (pH 7.3). To elute the bound DNA oligonucleotides from the Immobilization Field, the chip was submerged into an aliquot of 600 μL of 1× selection buffer (50 mM citric acid/sodium citrate dihydride, 466 mM NaCl, 12 mM KCl, 4.1 mM CaCl$_2$), pH 5.5) and incubated at 95° C. for 15 min. The supernatant was recovered and the elution step was repeated with another aliquot of 600 μL of 1× selection buffer. The two elution solutions were combined, purified with a GeneJET PCR purification kit, and the DNA eluted from the column with 30 μL of water.

For the positive selection steps, the 30 μL DNA library solution was mixed with 5 μL of 10× citrate buffer (0.5 M citric acid/sodium citrate dihydride, pH 5.5), 5 μL of 10× salt stock solution (4.66 M NaCl, 0.12 KCl, 0.041 M CaCl$_2$)), 5 μL of a 10× target molecule solution (1 μM; final concentration 100 nM), and 5 μL of water. The solution was incubated at room temperature for 10 min to allow the binding of the target molecule to the aptamers. Then, the solution was applied to the surface of the Immobilization Field and incubated at room temperature for 30 min with gentle shaking (50 rpm). The DNA solution was recovered from the chip. The surface of the chip was washed twice with aliquots of 50 μL of 1× selection buffer and the solutions were also recovered. All the collected solutions were combined, purified using a GeneJET PCR purification kit using the manufacturer's protocol, and the DNA eluted from the column with 400 μL of water.

A.4. Library Recovery after Each Selection Round

Figure 4:
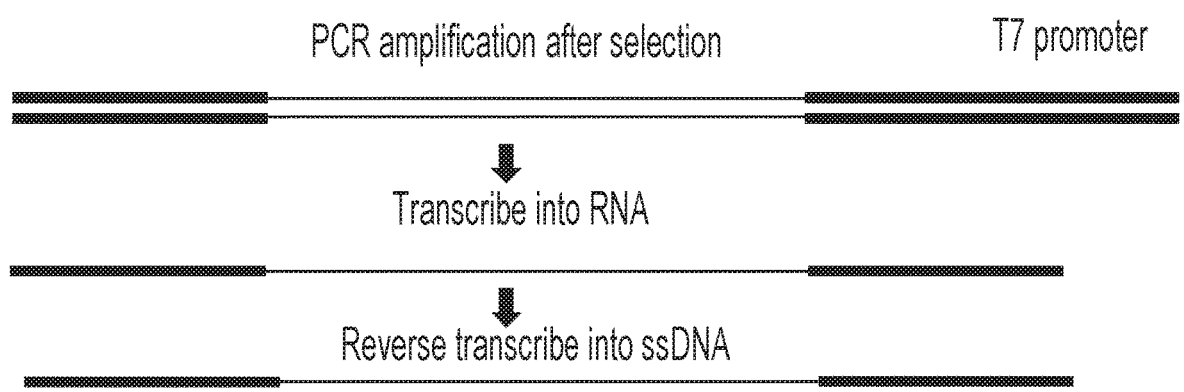
FIG. 4—Schematic of the DNA library recovery after each selection round.

After each selection round, the single stranded DNA oligonucleotides were amplified and recovered as follows (see FIG. 4). First, a T7 RNA polymerase promoter was incorporated into the 3' end of the library during a PCR amplification step by using a 3'-primer encoding such promoter and Taq polymerase. Then, the library was transcribed into the RNA antisense strand and the remaining double stranded library was removed with a DNase treatment. The resulting RNA oligonucleotides were subsequently reverse transcribed back into single stranded DNA oligonucleotides by using reverse transcriptase and the remaining RNA library was removed with an RNase treatment, recovering the library for next selection round (Lecocq S, Spinella K, Dubois B, Lista S, Hampel H, Penner G (2018) Aptamers as biomarkers for neurological disorders. Proof of concept in transgenic mice. PLoS ONE 13(1): e0190212. https://doi.org/10.1371/journal.pone.0190212). FIG. 4 is a schematic of the DNA library recovery after each selection round.

B. Aptamers Sequencing

The libraries from selection rounds 6, 8, and 9 in each channel were prepared for next generation sequencing (NGS) through a two-step PCR process. In the first step, a different hex code (6 base sequence) and a portion of a universal sequencing primer was added to the 5' end of each aptamer library. In the second step, complete universal sequencing primers were added to both ends. After the second PCR step, the libraries were purified through acrylamide electrophoresis and balanced for relative quantity. These libraries were then pooled and submitted for NGS sequencing using an Illumina HiSeq instrument (Hospital for Sick Children, Toronto, CA).

The sequencing data was tabulated and analyzed. A total of 36,662,064 sequences were analyzed and each library contained more than 2,000,000 different sequences. The sequences from selection round 9 within each channel were sorted by copy number and named in descending order with the highest copy number sequence being named Mal-1-1, Mal-2-1, Mal-3-1, and Mal-4-1 for target molecules 1 to 4, respectively. These top sequences are listed in Table 1.

For each channel, the copy numbers of the top sequences of selection round 9 (see Table 1) were determined on the libraries obtained from the other selection rounds. Finally, the frequency was computed for each sequence by dividing observed copy number by the total number of sequences observed in the particular library.

Example 16. Analysis of Sequences Similarity

Alignment of SEQ ID NO 1 to SEQ ID NO 400 was performed using the software Align X, a component of Vector NTI Advanced 11.5.4 by Invitrogen. Several groups of sequences have at least 90%, at least 70%, or at least 50% nucleotide sequence identity as illustrated in the alignments of FIGS. 5, 6, and 7. In these alignments, only the central variable region of the aptamers was included for simplicity. Thus, oligonucleotides with at least 50%, at least 70%, or at least 90% nucleotide sequence identity to sequences selected from the group consisting of SEQ ID NO 1 to SEQ ID NO 400 are included as part of the current invention. FIG. 5 shows the alignment of exemplary sequences with at least 90% nucleotide sequence identity that are identified during the selection process. FIG. 6 shows the alignment of exemplary sequences with at least 70% nucleotide sequence identity that are identified during the selection process. FIG. 7 shows the alignment of exemplary sequences with at least 50% nucleotide sequence identity that are identified during the selection process.

Example 17. Motif Analysis

The frequency of motifs of six nucleotides from the random regions of the top aptamers (Mal-1-1, Mal-2-1, Mal-3-1, and Mal-4-1) within all the sequences of selection round 9 library was determined. Then, the average motif frequency was subtracted from the frequency of each motif and this value was divided by the standard deviation of all the motifs frequencies in that selection round, resulting in a Z value for every motif. It stands to reason that sequences containing high frequency motifs also bind to the target molecule and are part of the present invention.

The prediction of the secondary structures of the aptamers was performed with The Vienna RNA Website. (http://rna.tbi.univie.ac.at//cgi-bin/RNAWebSuite/RNAfold.cgi. Gruber A R, Lorenz R, Bernhart S H, Neuböck R, Hofacker I L; Nucleic Acids Research, Volume 36, Issue suppl_2, 1 Jul. 2008, Pages W70-W74, DOI: 10.1093/nar/gkn188) and the motifs are highlighted within these structures.

A. Analysis of Random Region of Aptamer Mal-1.1:

The motifs:

```
SEQ ID NO 401:
5'-AGGAGATAA-3'

Figure 9:
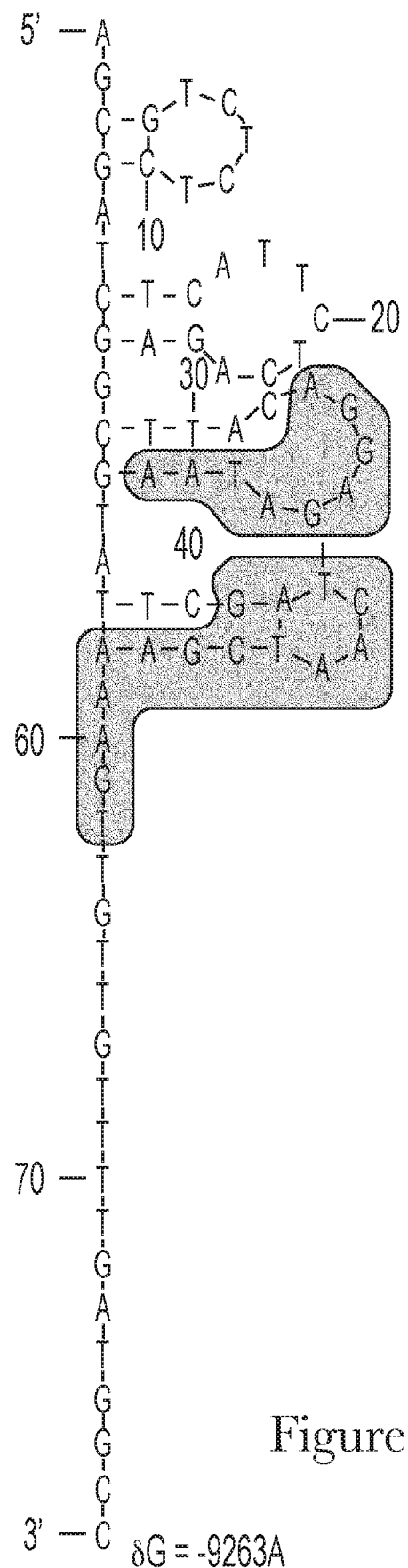
FIG. 9—The predicted secondary structures of aptamer Mal-1-1 and its conserved motifs.

SEQ ID NO 402:
5'-GATCAANNNAAAAGT-3'
``` from the variable region of sequence Mal-1.1 (SEQ ID NO 1):

```
5'-GAGGCTTACAGGAGATAAGTATTCGATCAATCGAAAAGTT-3'
``` where N stands for any nucleotide, were found at a significantly higher frequency than would be expected randomly (see FIG. 8). This finding indicates that these motifs were positively selected for within this molecular target-based aptamer selection process. Any sequences containing these motifs are also expected to bind to the molecular target and are part of the present invention. The predicted secondary structure of aptamer Mal-1.1 with the highlighted motifs is illustrated in FIG. 9.

Figure 10:
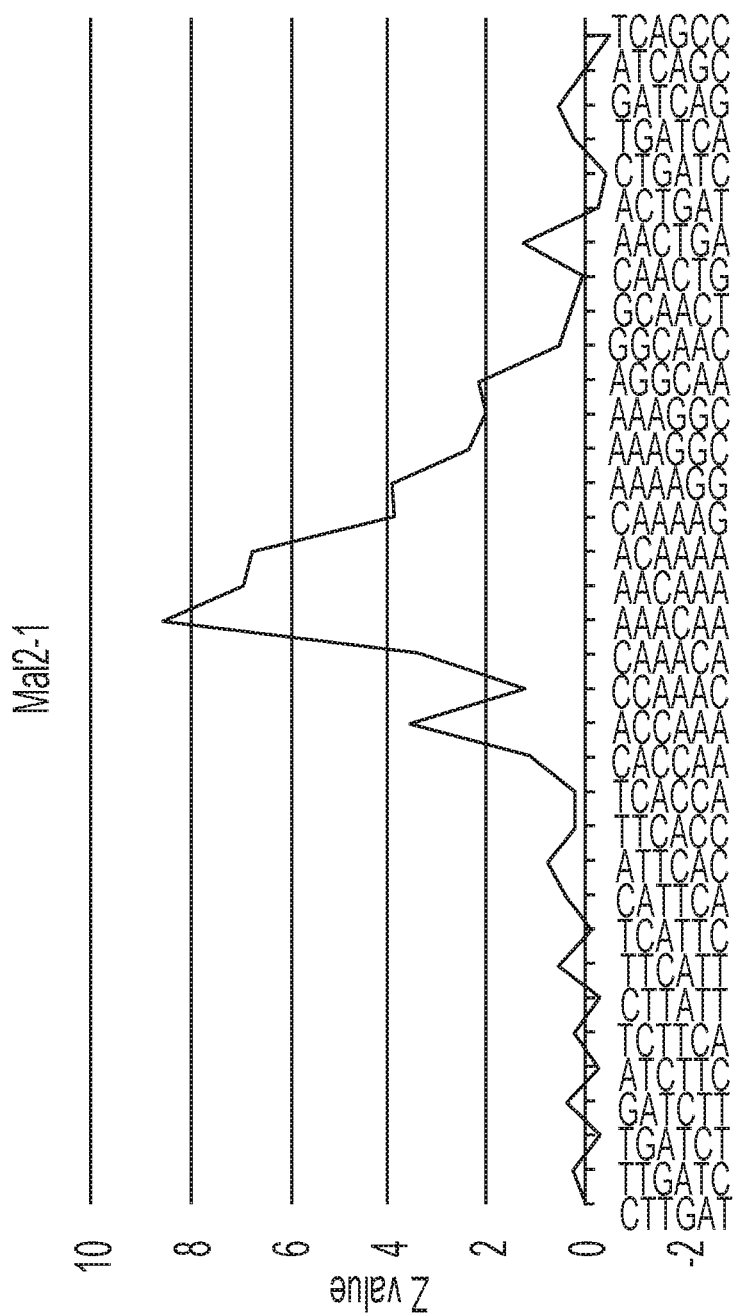
FIG. 10—Motif analysis of random region of aptamer Mal-2-1.

B. Analysis of Random Region of Aptamer Mal-2.1:
The motif:

```
SEQ ID NO 403:
5'-ACCAAANAAAAGGCAA-3'
``` from the variable region of sequence Mal-2.1 (SEQ ID NO 101):

```
5'-CTTGATCTTCATTCACCAAACAAAAGGCAACTGATCAGCC-3'
``` where N stands for any nucleotide, is found at a significantly higher frequency than would be expected randomly (see FIG. 10). This finding indicates that this motif is positively selected for within this molecular target-based aptamer selection process. Any sequences containing this motif are also expected to bind to the molecular target and are part of the present invention. The predicted secondary structure of aptamer Mal-2.1 with the highlighted motif is illustrated in FIG. 11.

C. Analysis of Random Region of Aptamer Mal-3.1:
The motifs:

```
SEQ ID NO 404:
5'-AACGGAANNGA-3'

Figure 12:
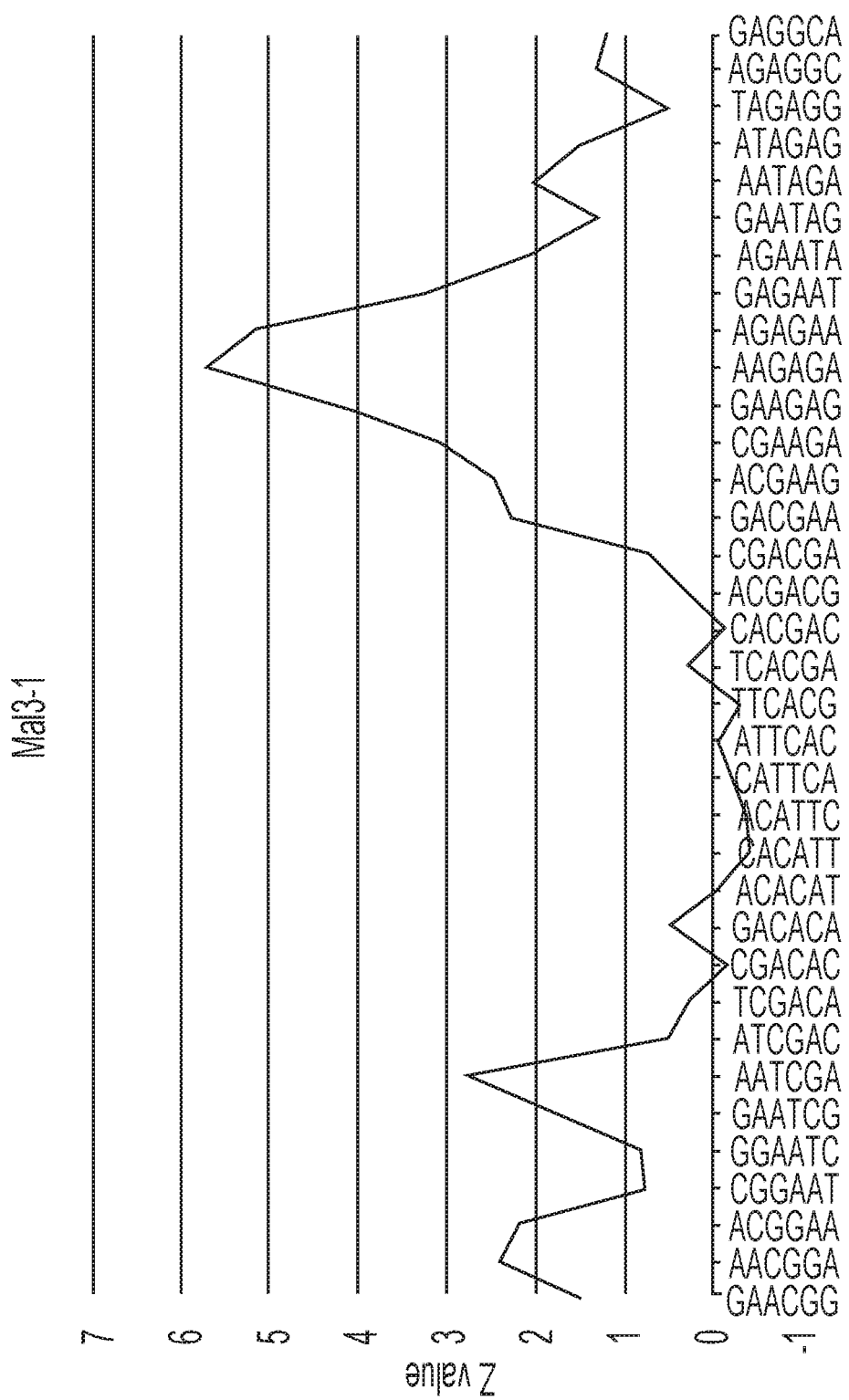
FIG. 12—Motif analysis of random region of aptamer Mal-3-1.
Figure 13:
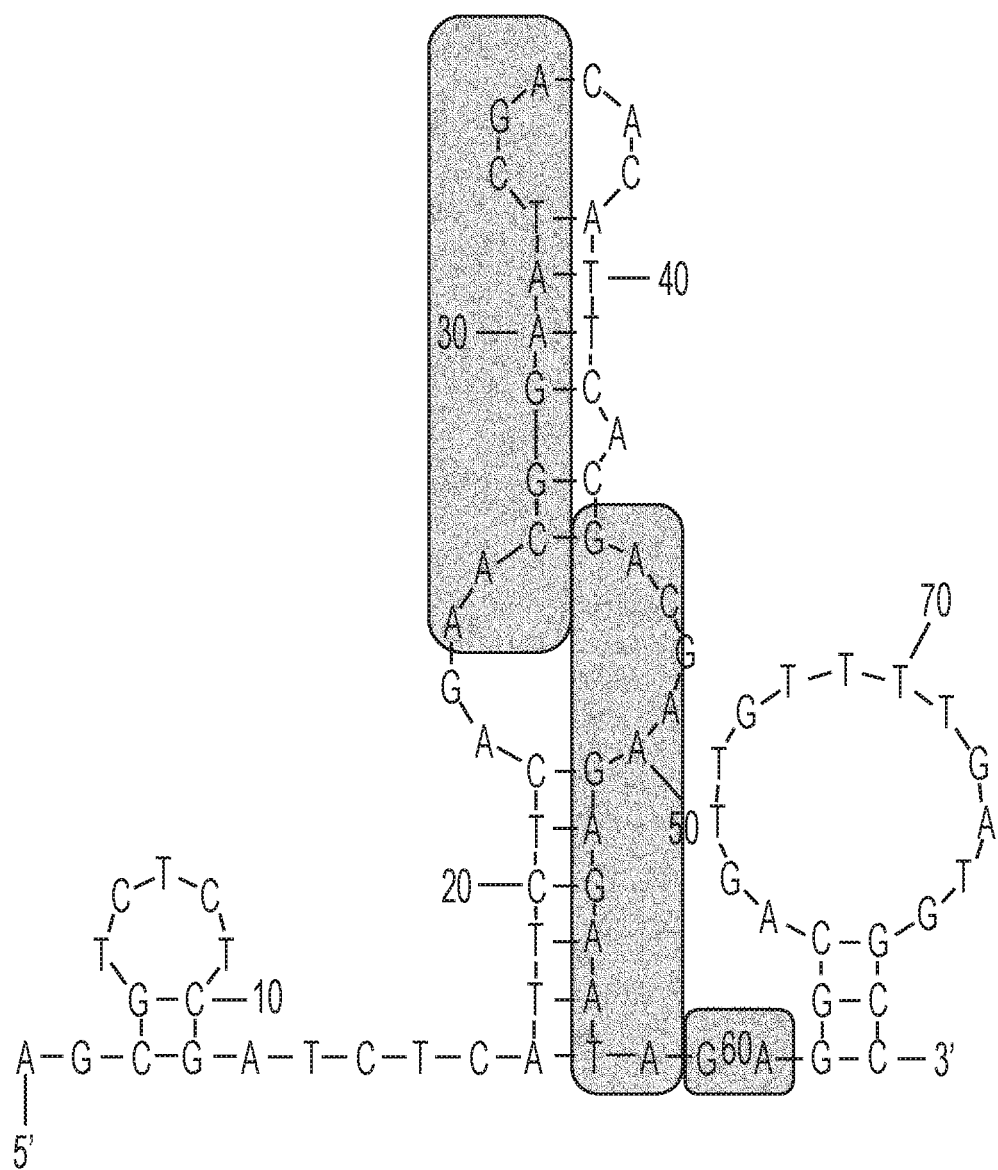
FIG. 13—The predicted secondary structures of aptamer Mal-3-1 and its conserved motifs.

SEQ ID NO 405:
5'-GACGAAGAGAATANA-3'
``` from the variable region of sequence Mal-3.1 (SEQ ID NO 201):

```
5'-GAACGGAATCGACACATTCACGACGAAGAGAATAGAGGC-3'
``` where N stands for any nucleotide, are found at a significantly higher frequency than would be expected randomly (see FIG. 12). This finding indicates that these motifs are positively selected for within this molecular target-based aptamer selection process. Any sequences containing these motifs are also expected to bind to the molecular target and are part of the present invention. The predicted secondary structure of aptamer Mal-3.1 with the highlighted motifs is illustrated in FIG. 13.

Figure 14:
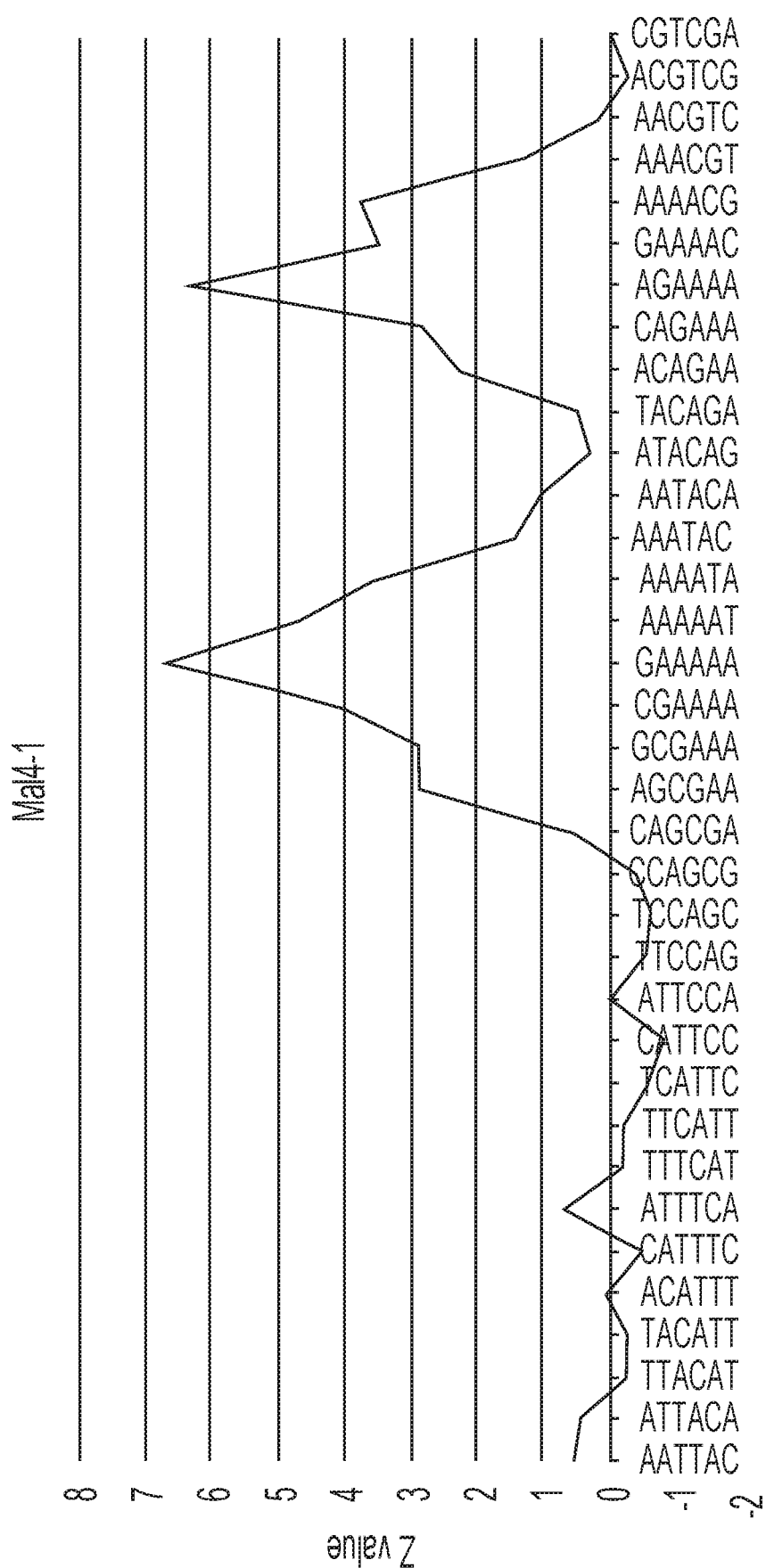
FIG. 14—Motif analysis of random region of aptamer Mal-4-1.
Figure 15:
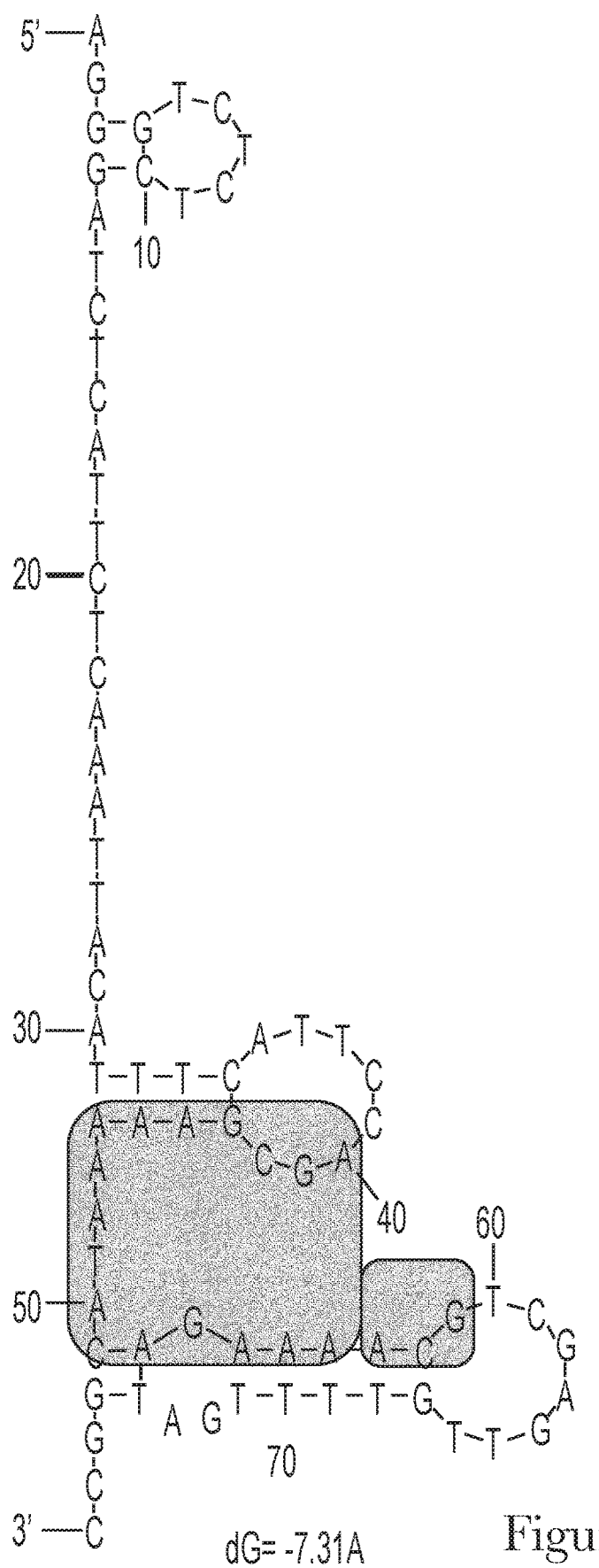
FIG. 15—The predicted secondary structures of aptamer Mal-4-1 and its conserved motif.

D. Analysis of Random Region of Aptamer Mal-4.1:
The motif:

```
SEQ ID NO 406:
5'-AGCGAAAAATANNNAAAACG-3'
``` from the variable region of sequence Mal-4.1 (SEQ ID NO 301):

```
5'-AATTACATTTCATTCCAGCGAAAAATACAGAAAACGTCGA-3'
``` where N stands for any nucleotide, is found at a significantly higher frequency than would be expected randomly (see FIG. 14). This finding suggests that this particular motif is positively selected for within this molecular target-based aptamer selection process. Any sequences containing this motif are also expected to bind to the molecular target may be part of the present invention. The predicted secondary structure of aptamer Mal-4.1 with the highlighted motif is illustrated in FIG. 15.

Example 18. Truncation of Aptamers

Figure 16:
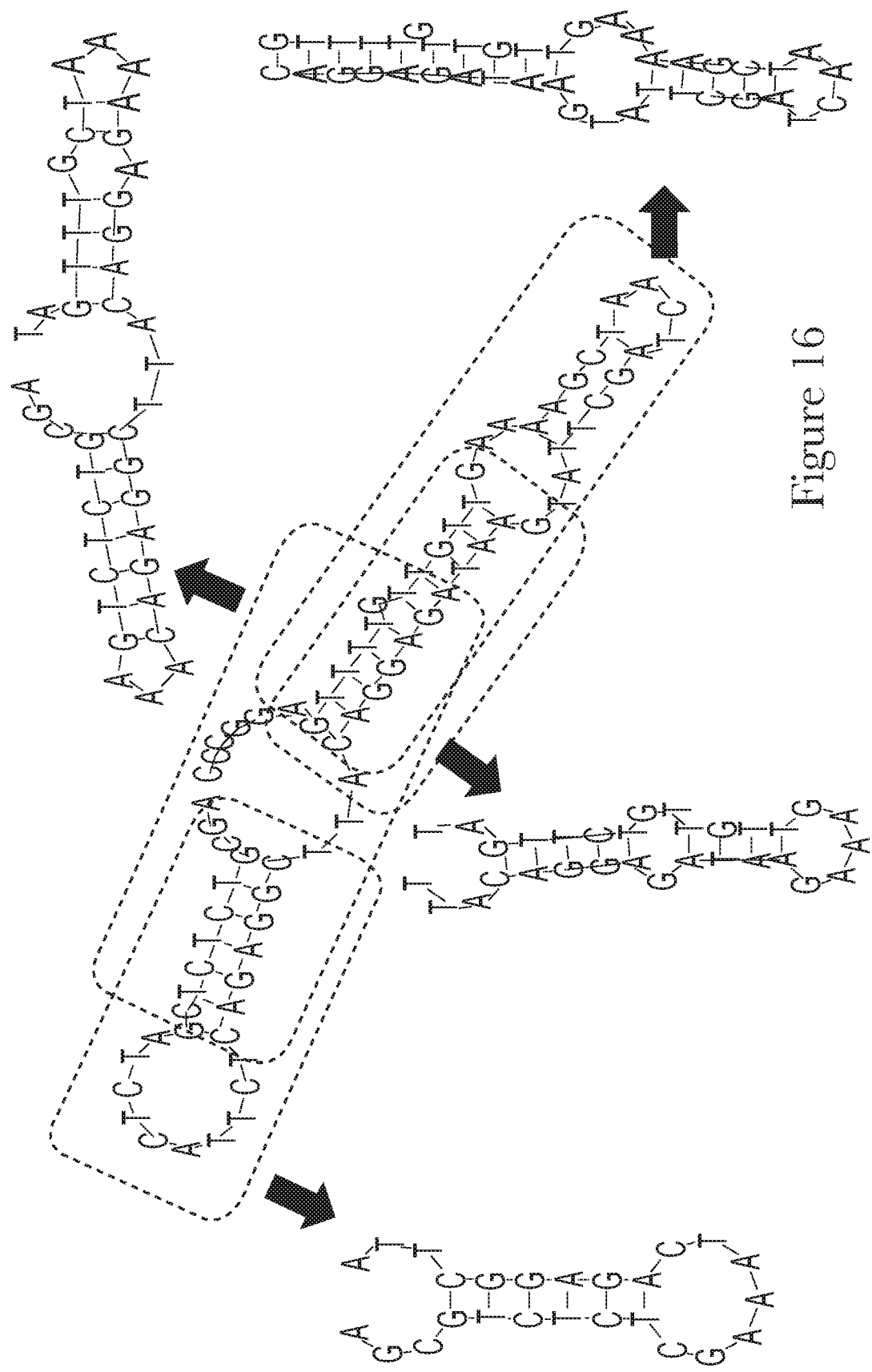
FIG. 16—The predicted secondary structures of aptamer Mal-1-1 and truncated aptamers Mal-1-1.A, Mal-1-1.B, Mal-1-1.C, and Mal-1-1.D.
Figure 17:
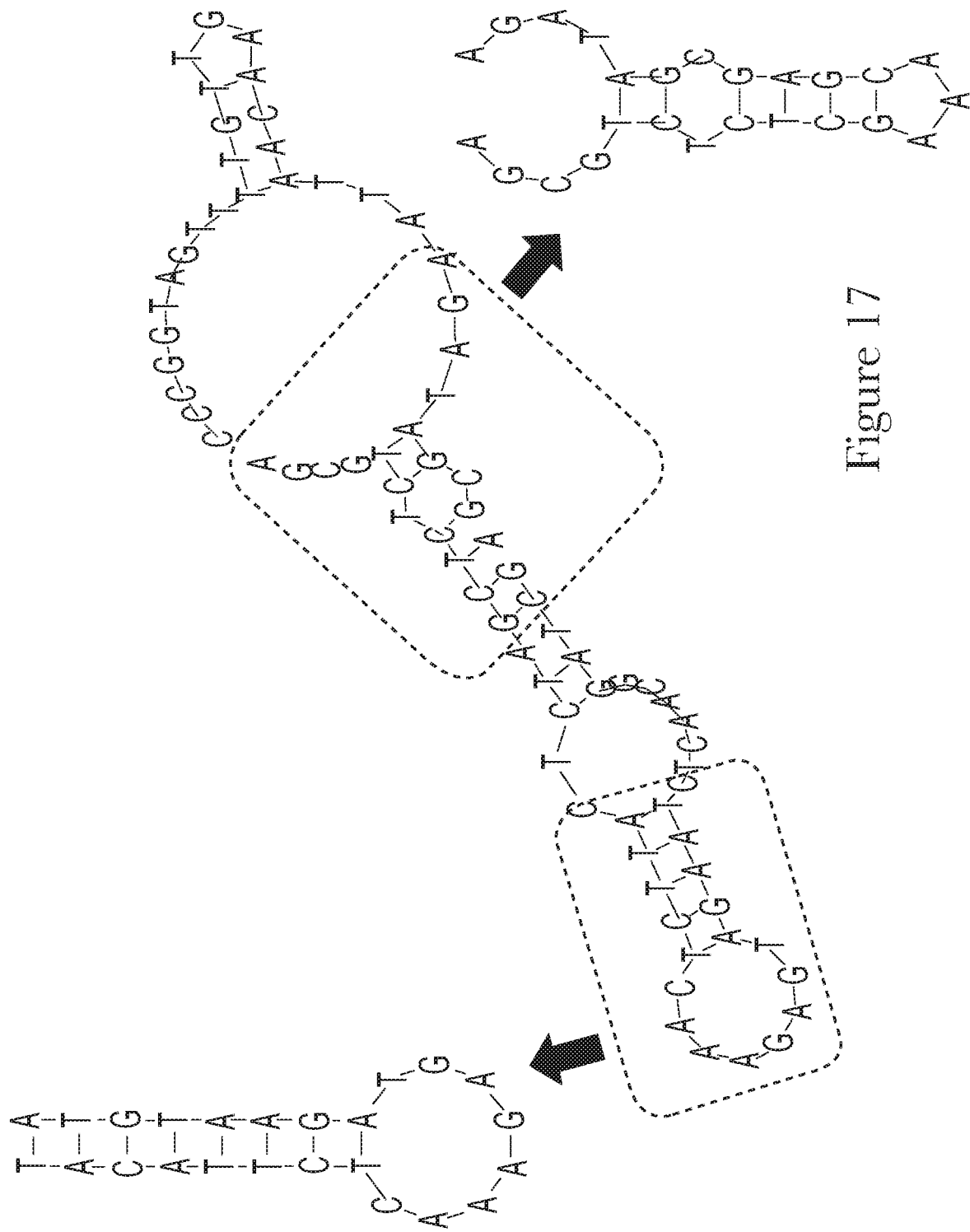
FIG. 17—The predicted secondary structures of aptamer Mal-1-2 and truncated aptamers Mal-1-2.A and Mal-1-2.B.
Figure 18:
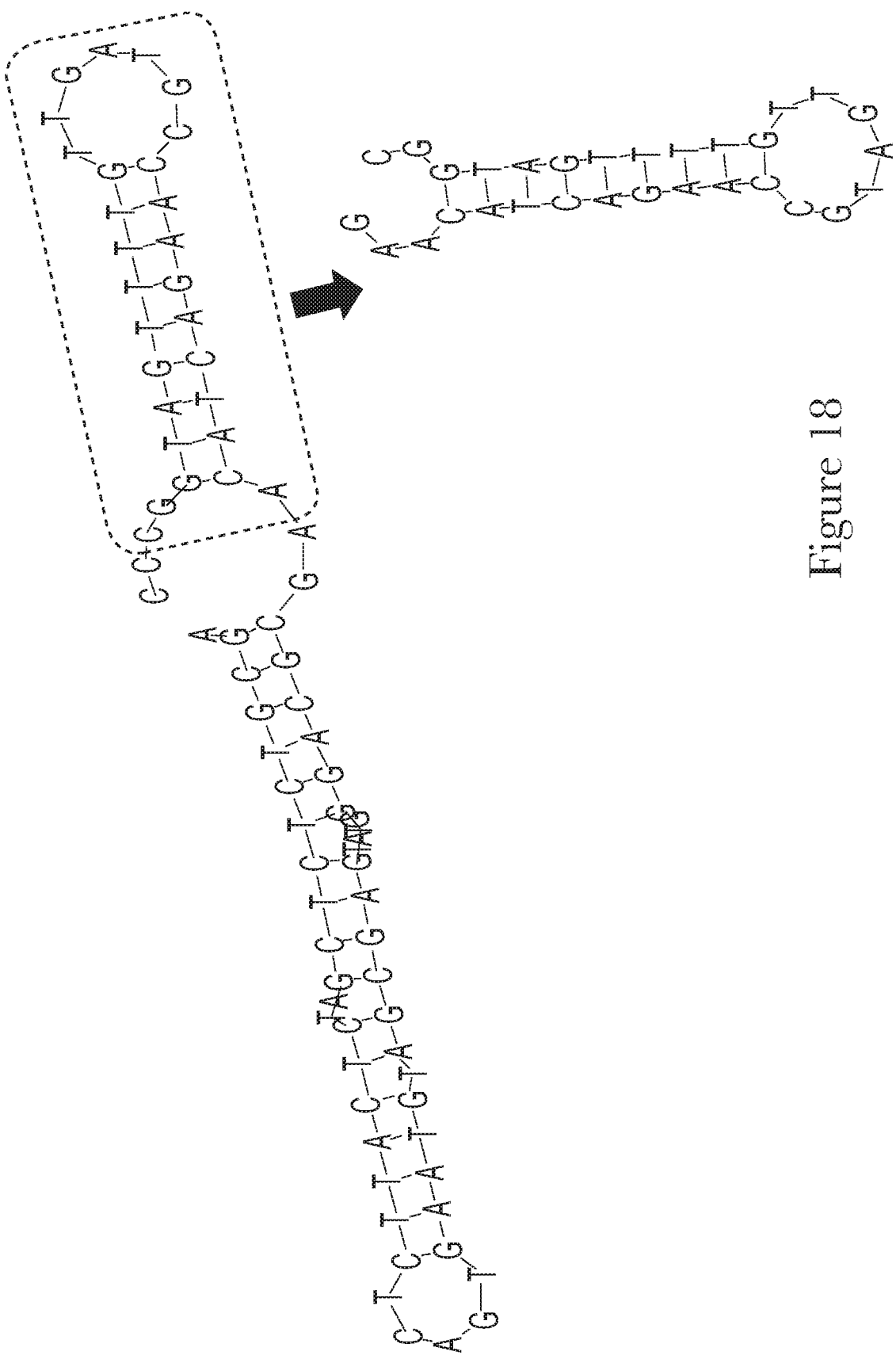
FIG. 18—The predicted secondary structures of aptamer Mal-1-3 and truncated aptamer Mal-1-3.A.
Figure 19:
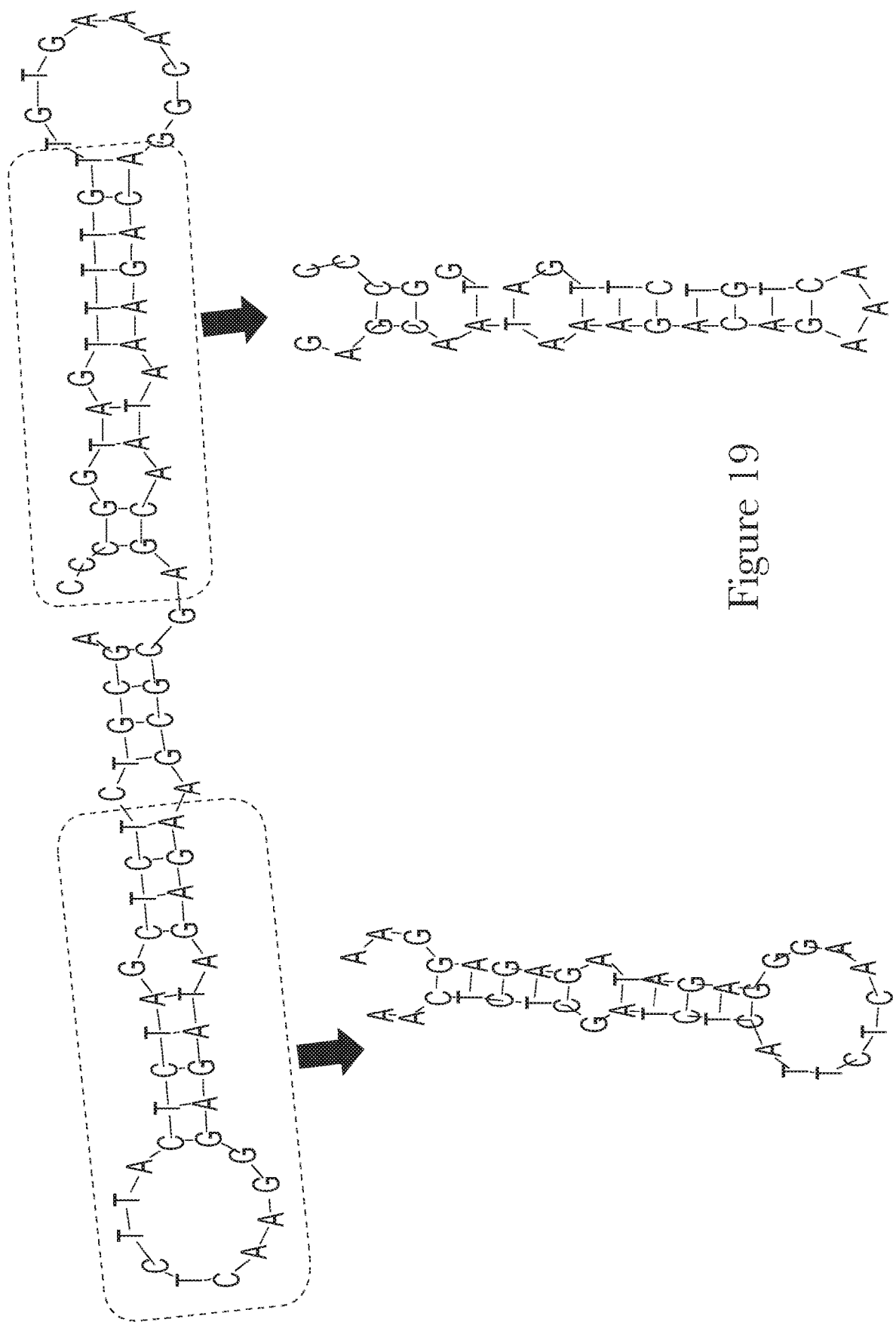
FIG. 19—The predicted secondary structures of aptamer Mal-1-4 and truncated aptamers Mal-1-4.A and Mal-1-4.B.

Starting from the predicted secondary structure of the selected aptamers (Mal-1-1, Mal-1-2, Mal-1-3, and Mal-1-4), smaller oligonucleotides comprising some of the secondary structure elements or segments of the sequence were designed. Mutations were included as necessary to preserve the secondary structures of the parent aptamer. For instance, aptamers Mal-1-1.A (SEQ ID NO 407), Mal-1-1.B (SEQ ID NO 408), Mal-1-1.0 (SEQ ID NO 409), and Mal-1-1.D (SEQ ID NO 410) were derived from aptamer Mal-1-1 (see FIG. 16). Aptamer Mal-1-1.A was designed to preserve the central stems of aptamer Mal 1-1, whiles aptamers Mal-1-1.B, Mal-1-1.C, and Mal-1-1.D are expected to maintain the side stems and loops. Aptamers Mal-1-2.A (SEQ ID NO 411) and Mal-1-2.B (SEQ ID NO 412) were derived from aptamer Mal-1-2 (see FIG. 17). Aptamers Mal-1-3.A (SEQ ID NO 413) was derived from aptamer Mal-1-3 (see FIG. 18). Aptamers Mal-1-4.A (SEQ ID NO 414) and Mal-1-4.B (SEQ ID NO 415) were derived from aptamer Mal-1-4 (see FIG. 19) and both of them are expected to maintain some of the steams and loops of the parent aptamer. The list of sequences of truncated aptamers is included in TABLE 3 and included as part of the current invention.

TABLE 1

List of top sequences from selection experiment.

| SEQ ID NO | Name | Sequence |
|---|---|---|
| 1 | Mal-1-1 | AGCGTCTCTCGATCTCATTCTCAGAGGCTTACAGGAGATAAGTATTCGATCAATCGAAAAGTTGTTGTTTTGATGGCCC |
| 2 | Mal-1-2 | AGCGTCTCTCGATCTCATTCTCAAAGAGTAGAATCTCAACGGATCGAGCGATAGAATTAACAAGTTGTTTTGATGGCCC |
| 3 | Mal-1-3 | AGCGTCTCTCGATCTCATTCTCAGTGAATGTAGCGAGTATGGGACGCGAACATCAGAACCGTAGTTGTTTTGATGGCCC |
| 4 | Mal-1-4 | AGCGTCTCTCGATCTCATTCTCAAGGGAGATAGAGAAGCGCGAGCAATAAAGACAGGCAAAGTGTTGTTTTGATGGCCC |
| 5 | Mal-1-5 | AGCGTCTCTCGATCTCATTCTCACGAGAATGGTCGAAGATGCGGAGGGAAAACTACAAGTAGTGTTGTTTTGATGGCCC |
| 6 | Mal-1-6 | AGCGTCTCTCGATCTCATTCTCATATAATTATGAGACGAGCAGCGAGAGTAGCGAGCCAGAAGGTTGTTTTGATGGCCC |
| 7 | Mal-1-7 | AGCGTCTCTCGATCTCATTCTCAAAAATTAATGAGATTCGGGAATGAGTTATCGAGCACGCGGGTTGTTTTGATGGCCC |
| 8 | Mal-1-8 | AGCGTCTCTCGATCTCATTCTCAAGGGAGGAATGAGGTCTAAGAAGGCGAGGACAAAGCAAGAGTTGTTTTGATGGCCC |

TABLE 1-continued

List of top sequences from selection experiment.

| SEQ ID NO | Name | Sequence |
|---|---|---|
| 9 | Mal-1-9 | AGCGTCTCTCGATCTCATTCTCAAGGGCAGAGAACGACGTCGAGTGATGCGACCGCAAAGACAGTTGTTTTGATGGCCC |
| 10 | Mal-1-10 | AGCGTCTCTCGATCTCATTCTCACGCGTAGTGAAGAAGAAGATGAGTAGCCGCGACAACAAAAGTTGTTTTGATGGCCC |
| 11 | Mal-1-11 | AGCGTCTCTCGATCTCATTCTCAGAAAGGAAATGGAGCGAGAGTGAAGCGGCCGGTGAAACTGGTTGTTTTGATGGCCC |
| 12 | Mal-1-12 | AGCGTCTCTCGATCTCATTCTCAGAATATGTCGAGGTAACGCGAGGAGAAAAAACAACAGTTAGTTGTTTTGATGGCCC |
| 13 | Mal-1-13 | AGCGTCTCTCGATCTCATTCTCAATGTACGTAGAGAGGCGCACGGCCACTCAGAGAACAGTCGGTTGTTTTGATGGCCC |
| 14 | Mal-1-14 | AGCGTCTCTCGATCTCATTCTCAGAACTACATCTGAGAGGATCCGCAAGAGAAGCGGGACAAGGTTGTTTTGATGGCCC |
| 15 | Mal-1-15 | AGCGTCTCTCGATCTCATTCTCAGCAGAGAGCTAAGGGTGAGTAGATCGAGTCAAGAGCGCGGGTTGTTTTGATGGCCC |
| 16 | Mal-1-16 | AGCGTCTCTCGATCTCATTCTCAAAATGGCCTAAGTGCCGAGAGATGAGGCGAGGAGAGAGCCGTTGTTTTGATGGCCC |
| 17 | Mal-1-17 | AGCGTCTCTCGATCTCATTCTCAACGAGAAGGAATCGAAAAGCGTGCGAAATCAATCAGCGAGGTTGTTTTGATGGCCC |
| 18 | Mal-1-18 | AGCGTCTCTCGATCTCATTCTCAAGAGATGAGGGCGAGGGAAGCGGCCAAAAAATTAAGCACGTTGTTTTGATGGCCC |
| 19 | Mal-1-19 | AGCGTCTCTCGATCTCATTCTCAAAGAAAGCCGAGAGAGGCGCATAATCAAAAGCAAATCGAAGTTGTTTTGATGGCCC |
| 20 | Mal-1-20 | AGCGTCTCTCGATCTCATTCTCAACGGAAAGGTGTGAACGAGTAAACGAGAAGCGGCGACCAAGTTGTTTTGATGGCCC |
| 21 | Mal-1-21 | AGCGTCTCTCGATCTCATTCTCACTAGAGAAGGGATCGGGTACGCGGACGAAACGGTAAACAGGTTGTTTTGATGGCCC |
| 22 | Mal-1-22 | AGCGTCTCTCGATCTCATTCTCATAGTGAATAAGGAAAAGGACGCGGAAGCACGAAACACTAGGTTGTTTTGATGGCCC |
| 23 | Mal-1-23 | AGCGTCTCTCGATCTCATTCTCAAAACGAAGAAGGGAATCAGATCGAAAGGCTCCAGAAAAAGTTGTTTTGATGGCCC |
| 24 | Mal-1-24 | AGCGTCTCTCGATCTCATTCTCAAAGAGAATAGCCGAGTAAGCGAGGGCTCAAACGAGTTCACGTTGTTTTGATGGCCC |
| 25 | Mal-1-25 | AGCGTCTCTCGATCTCATTCTCAAAGAGGATCGAGAAGGCGGATCGACAAAGAAAGAAACTTCGTTGTTTTGATGGCCC |
| 26 | Mal-1-26 | AGCGTCTCTCGATCTCATTCTCACAGACGTGAGAATAATCGGTAGATGCGGACCACGAACAGCGTTGTTTTGATGGCCC |
| 27 | Mal-1-27 | AGCGTCTCTCGATCTCATTCTCAGGTGGCCAGTAGAATGGATCGGGAAGCGGTCGAAAAACAGTTGTTTTGATGGCCC |
| 28 | Mal-1-28 | AGCGTCTCTCGATCTCATTCTCATGCGAAGAAAGATAGAGCGACGCGGTACCAAAAGGCAACAGTTGTTTTGATGGCCC |
| 29 | Mal-1-29 | AGCGTCTCTCGATCTCATTCTCAAGTGTGAAAAGGATCGACAACGAGCAGCGCGACCAGACAAGTTGTTTTGATGGCCC |
| 30 | Mal-1-30 | AGCGTCTCTCGATCTCATTCTCACCGGGTGGATATGAATGATCGGAAGTGGGGTGATTGGTCGGTTGTTTTGATGGCCC |
| 31 | Mal-1-31 | AGCGTCTCTCGATCTCATTCTCATTGGTAAGTACGTAGAATGAATCGGGATCGCGACCATCGAGTTGTTTTGATGGCCC |
| 32 | Mal-1-32 | AGCGTCTCTCGATCTCATTCTCAAGAGAGTGGAGTAGAGAGATGCGACGGAGAGGAAAAAGCGTTGTTTTGATGGCCC |
| 33 | Mal-1-33 | AGCGTCTCTCGATCTCATTCTCAGTTAATATGAAATCTAACAAGTCGAGGACGGCAAGTTCTAGTTGTTTTGATGGCCC |
| 34 | Mal-1-34 | AGCGTCTCTCGATCTCATTCTCACTTGATGAACAAGAGAAGAGACAAGCGCGCTGCATCAGAAGTTGTTTTGATGGCCC |
| 35 | Mal-1-35 | AGCGTCTCTCGATCTCATTCTCATGGGAAGCGAGGAAGCGGGACAAATAACAATCAGCTGCTGGTTGTTTTGATGGCCC |
| 36 | Mal-1-36 | AGCGTCTCTCGATCTCATTCTCACTGAGTGATCAAATGAGTTGAGATCGAGGAAAGGCGGAGAGTTGTTTTGATGGCCC |
| 37 | Mal-1-37 | AGCGTCTCTCGATCTCATTCTCAGCAGATGAGATGAGCTGAGCGAGTAACGAGAGTGGCAAGGGTTGTTTTGATGGCCC |
| 38 | Mal-1-38 | AGCGTCTCTCGATCTCATTCTCAGGGGATCGAGGTGCGAGCCAAAAAGAGTTGATGAAAGTGAGTTGTTTTGATGGCCC |
| 39 | Mal-1-39 | AGCGTCTCTCGATCTCATTCTCACCCGTTGGCAAACGGAGATAAAGGGGATCAGAGAGCGCGGGTTGTTTTGATGGCCC |
| 40 | Mal-1-40 | AGCGTCTCTCGATCTCATTCTCAGAAATGAGCGAGAATCGGAGGATGCGCACCATCACCAACAGTTGTTTTGATGGCCC |
| 41 | Mal-1-41 | AGCGTCTCTCGATCTCATTCTCATGAATTGAGGACAAGACGCGGCGCAGTGAAGTAGACCAATGTTGTTTTGATGGCCC |
| 42 | Mal-1-42 | AGCGTCTCTCGATCTCATTCTCAAGGAGACAATAGTGCGAGGAAACGCGGCAAACAAGAGGAAGTTGTTTTGATGGCCC |
| 43 | Mal-1-43 | AGCGTCTCTCGATCTCATTCTCAATGAAGATCGACAAGCGGACACCACAAAAGCTGTGCCGCAGTTGTTTTGATGGCCC |
| 44 | Mal-1-44 | AGCGTCTCTCGATCTCATTCTCAGAAACTTGAATGAGACAGGAGAAGTCGCGGGTATCTGACAGTTGTTTTGATGGCCC |
| 45 | Mal-1-45 | AGCGTCTCTCGATCTCATTCTCAGCAAGGAGATTACAAGAGCGAGAAAGGATGAGACATAGAGGTTGTTTTGATGGCCC |
| 46 | Mal-1-46 | AGCGTCTCTCGATCTCATTCTCATAACTATGAGATATAAACGGTGAGAGAAGAGGCGGACTCAGTTGTTTTGATGGCCC |

TABLE 1-continued

List of top sequences from selection experiment.

| SEQ ID NO | Name | Sequence |
|---|---|---|
| 47 | Mal-1-47 | AGCGTCTCTCGATCTCATTCTCACAATAGTGGAGAATAAAACCGAGAAAACCGCGACAGCATAGTTGTTTTGATGGCCC |
| 48 | Mal-1-48 | AGCGTCTCTCGATCTCATTCTCAAAGAGAGAAGGCGAGCGAGGCAAAGAGAGGAAACTTGGTAGTTGTTTTGATGGCCC |
| 49 | Mal-1-49 | AGCGTCTCTCGATCTCATTCTCAATCAGATCAAGGGAAGTGAGCAGATCATCAAACAAACAACGTTGTTTTGATGGCCC |
| 50 | Mal-1-50 | AGCGTCTCTCGATCTCATTCTCACGCCAGTGAGGCTAGAGAGAGTCCGCGGGCAAGACTAACAGTTGTTTTGATGGCCC |
| 51 | Mal-1-51 | AGCGTCTCTCGATCTCATTCTCACGCTAGTAAGATGACTCGAGGAGCGGGCTCAAACGGACAAGTTGTTTTGATGGCCC |
| 52 | Mal-1-52 | AGCGTCTCTCGATCTCATTCTCAGCGCGTCGATGAGCATAGAGAGATCGGGTAAGACGAGGACGTTGTTTTGATGGCCC |
| 53 | Mal-1-53 | AGCGTCTCTCGATCTCATTCTCAAACGGATCGAGAAGAGGCGCGCTGTCAGAGCAAATCGATAGTTGTTTTGATGGCCC |
| 54 | Mal-1-54 | AGCGTCTCTCGATCTCATTCTCACATATAATACGAGAGAAAGATCCGAGAAGCGGCGAAAAGAGTTGTTTTGATGGCCC |
| 55 | Mal-1-55 | AGCGTCTCTCGATCTCATTCTCAAAGCGGGACGCGAGCATATGAAGATCGAAGAGCAAAAAACGTTGTTTTGATGGCCC |
| 56 | Mal-1-56 | AGCGTCTCTCGATCTCATTCTCAGATGTGATCGTGACGAATGATCGAAAACGCGGGCGAGTAGGTTGTTTTGATGGCCC |
| 57 | Mal-1-57 | AGCGTCTCTCGATCTCATTCTCAAATAAGGTGTAAGAGAAGGACAGAGAGCGGCATAAGAGAGGTTGTTTTGATGGCCC |
| 58 | Mal-1-58 | AGCGTCTCTCGATCTCATTCTCAAGAATGAGGTCGGTGGAAGCGAACCAAGGAAAAAGCTCGAGTTGTTTTGATGGCCC |
| 59 | Mal-1-59 | AGCGTCTCTCGATCTCATTCTCAAGCTGAGGATTGAGAACTGAATCCGAGCGCGGATATCAAAGTTGTTTTGATGGCCC |
| 60 | Mal-1-60 | AGCGTCTCTCGATCTCATTCTCAATGAGACGGTACGCGGACAAAAGCAAGGAACCGTAGGAAAGTTGTTTTGATGGCCC |
| 61 | Mal-1-61 | AGCGTCTCTCGATCTCATTCTCACATAGGTGCAGCCTATGGTGGAAGAGAGAGACGTGGCAATGTTGTTTTGATGGCCC |
| 62 | Mal-1-62 | AGCGTCTCTCGATCTCATTCTCAGAAGAAAAAATCGAGAGGAGCGGAGAGAAACGATACGCAGGTTGTTTTGATGGCCC |
| 63 | Mal-1-63 | AGCGTCTCTCGATCTCATTCTCATGTTATCGAAGATGCGACAGACCAGCAGTTAGAAACAAAAGTTGTTTTGATGGCCC |
| 64 | Mal-1-64 | AGCGTCTCTCGATCTCATTCTCAAATAGAAAAGGAGATTTCGGAAGCGCGGAGACACCATGAAGTTGTTTTGATGGCCC |
| 65 | Mal-1-65 | AGCGTCTCTCGATCTCATTCTCAATAAAGGAGAAAGATGGATCGCGTGCGCGACTCACCAAAAGTTGTTTTGATGGCCC |
| 66 | Mal-1-66 | AGCGTCTCTCGATCTCATTCTCACATGATAATCGAGGGATGCGCCCATATCAAACTGACAGGAGTTGTTTTGATGGCCC |
| 67 | Mal-1-67 | AGCGTCTCTCGATCTCATTCTCAGTATGAGCGGGATCGTAAACGCGAGCTGCAAATAATGGTAGTTGTTTTGATGGCCC |
| 68 | Mal-1-68 | AGCGTCTCTCGATCTCATTCTCATAGACTTTAAGATCGTGATTCTCGGAGGGCAGATTAGTAAGTTGTTTTGATGGCCC |
| 69 | Mal-1-69 | AGCGTCTCTCGATCTCATTCTCAAAGAGAACCGTACAGAGTCGAGCAGAGCTGACAAAATAGAGTTGTTTTGATGGCCC |
| 70 | Mal-1-70 | AGCGTCTCTCGATCTCATTCTCAAAGCGTAAAACGCACGTAAAATGAGTCAAGAGAGCGGCGAGTTGTTTTGATGGCCC |
| 71 | Mal-1-71 | AGCGTCTCTCGATCTCATTCTCAAATGACCTAAGCGATGGGACGCGAGCACAAAAGGACAACGGTTGTTTTGATGGCCC |
| 72 | Mal-1-72 | AGCGTCTCTCGATCTCATTCTCAAGGTACATATACCGGAGATAGAATCGAGCACGAGCCGGAAGTTGTTTTGATGGCCC |
| 73 | Mal-1-73 | AGCGTCTCTCGATCTCATTCTCACGGTGAGAATAGCGAAGACAAGGCAGCGGATAAAAAAGCAGTTGTTTTGATGGCCC |
| 74 | Mal-1-74 | AGCGTCTCTCGATCTCATTCTCAGATGAAGACTAGAGAGCGACAGAAATAACCAACGCAAATCGTTGTTTTGATGGCCC |
| 75 | Mal-1-75 | AGCGTCTCTCGATCTCATTCTCAGCAATAAGGCAGGATGCTGTATGAGCAAGCGAGAGTACATGTTGTTTTGATGGCCC |
| 76 | Mal-1-76 | AGCGTCTCTCGATCTCATTCTCAGTCGATTTTTGTGTGCATGCGGACACTTGGGAGCGATCCGGTTGTTTTGATGGCCC |
| 77 | Mal-1-77 | AGCGTCTCTCGATCTCATTCTCAGTACACTGAGAAGATTGATCGGGAGATTTAGCGACCAGCAGTTGTTTTGATGGCCC |
| 78 | Mal-1-78 | AGCGTCTCTCGATCTCATTCTCATAGGAGAAGCTGGACGAGAAAGCGAGCCACCAATGGACATGTTGTTTTGATGGCCC |
| 79 | Mal-1-79 | AGCGTCTCTCGATCTCATTCTCATGAACGAGAAGTCTGAGAGATGCGGAGAGATCGAAACGAAGTTGTTTTGATGGCCC |
| 80 | Mal-1-80 | AGCGTCTCTCGATCTCATTCTCAATGAAAACAAGCAGCGAGGAGAGGCACTTTCAAACGCGAAGTTGTTTTGATGGCCC |
| 81 | Mal-1-81 | AGCGTCTCTCGATCTCATTCTCACTAAGTGGCTGGATCGAGAAGAACACGACCGTCAGAAAACGTTGTTTTGATGGCCC |
| 82 | Mal-1-82 | AGCGTCTCTCGATCTCATTCTCAGGAGACCGAAGAGCAGACCGCAAAACGATTACGAAGGCGCGTTGTTTTGATGGCCC |
| 83 | Mal-1-83 | AGCGTCTCTCGATCTCATTCTCAGTGAAAAGAGAGACCGGAGGATAGACCAAAGAAAGAGCATGTTGTTTTGATGGCCC |

TABLE 1-continued

List of top sequences from selection experiment.

| SEQ ID NO | Name | Sequence |
|---|---|---|
| 84 | Mal-1-84 | AGCGTCTCTCGATCTCATTCTCAGTTTGTTCTCAACGGAAAGTGAAACAGGGGAGCCCCACGAGTTGTTTTGATGGCCC |
| 85 | Mal-1-85 | AGCGTCTCTCGATCTCATTCTCAAGAGAATAAGAGTCAGAACACGGCACCGAAAGAGAAAAGCGTTGTTTTGATGGCCC |
| 86 | Mal-1-86 | AGCGTCTCTCGATCTCATTCTCAAGTAAAACCGAGAATGAAATGGATGATGCGAGATAGAAAAGTTGTTTTGATGGCCC |
| 87 | Mal-1-87 | AGCGTCTCTCGATCTCATTCTCAATGGAGATCTAGTAGCGCGGAACGATAAAACGGATCACGAGTTGTTTTGATGGCCC |
| 88 | Mal-1-88 | AGCGTCTCTCGATCTCATTCTCACGGGCACAAAGGTGCCTGGGAAACGCGAGATCGGAAACACGTTGTTTTGATGGCCC |
| 89 | Mal-1-89 | AGCGTCTCTCGATCTCATTCTCAGTTGTTAAACAACATAAGAATGCTCGGGTTGCCATGTCGGGTTGTTTTGATGGCCC |
| 90 | Mal-1-90 | AGCGTCTCTCGATCTCATTCTCAAGATCGAAATAAAGCGAGCATCGAACGAGTACAGCAAGAAGTTGTTTTGATGGCCC |
| 91 | Mal-1-91 | AGCGTCTCTCGATCTCATTCTCACTGAGAAAGAGAGCGTTGCGCGAGCAAAAGCAGACATAGGTTGTTTTGATGGCCC |
| 92 | Mal-1-92 | AGCGTCTCTCGATCTCATTCTCAGATGCTGGGAATGAGTGAAAGGGGATGCGAGTTGCAAAAGTTGTTTTGATGGCCC |
| 93 | Mal-1-93 | AGCGTCTCTCGATCTCATTCTCATTGGAGACCCAAGAGCGAGAACGCGAGTTTGGAAAACAAAGTTGTTTTGATGGCCC |
| 94 | Mal-1-94 | AGCGTCTCTCGATCTCATTCTCAAAGCATAGAAAGCGAAAGATCGGAAGGTAGTGGGCGAAGGGTTGTTTTGATGGCCC |
| 95 | Mal-1-95 | AGCGTCTCTCGATCTCATTCTCAAGAACGAGGTAACGAGCGCGGCCGAAGCAATGAAGGACGAGTTGTTTTGATGGCCC |
| 96 | Mal-1-96 | AGCGTCTCTCGATCTCATTCTCACTGAGGAAACAGAGCGAGTCAACGCGGAAATCAGAAATGCGTTGTTTTGATGGCCC |
| 97 | Mal-1-97 | AGCGTCTCTCGATCTCATTCTCACTTCAATACAGTAGAGGGAAAGATCGTGGGTGCCGATGTTGTTGTTTTGATGGCCC |
| 98 | Mal-1-98 | AGCGTCTCTCGATCTCATTCTCAGACGTGAGGATCGACGTAAACGCGCCTCTAGCAAAACGCAGTTGTTTTGATGGCCC |
| 99 | Mal-1-99 | AGCGTCTCTCGATCTCATTCTCAGTGGGATCGAGCAGAGCGGCGGATATAGACAAAAACCGTAGTTGTTTTGATGGCCC |
| 100 | Mal-1-100 | AGCGTCTCTCGATCTCATTCTCAGTGTGCTAATGAGAATAAAACGCGAGAGGATGAGAAACAAGTTGTTTTGATGGCCC |
| 101 | Mal-2-1 | AGCGTCTCTCGATCTCATTCTCACTTGATCTTCATTCACCAAACAAAGGCAACTGATCAGCCGTTGTTTTGATGGCCC |
| 102 | Mal-2-2 | AGCGTCTCTCGATCTCATTCTCATCTCGTAAACAAAAGAAACAAATGGACGACGACCGACAGGTTGTTTTGATGGCCC |
| 103 | Mal-2-3 | AGCGTCTCTCGATCTCATTCTCAATTCACTTGCTCCAAAAAGCAAAAGCAATCGGTCGACCGAGTTGTTTTGATGGCCC |
| 104 | Mal-2-4 | AGCGTCTCTCGATCTCATTCTCACTTTTTCAACTGTATTACACAAAATCAAAAAGCAGCCGCTGTTGTTTTGATGGCCC |
| 105 | Mal-2-5 | AGCGTCTCTCGATCTCATTCTCATAATTTACATACACTGAAAAAAGCGAAACAAGACGTAGAGGTTGTTTTGATGGCCC |
| 106 | Mal-2-6 | AGCGTCTCTCGATCTCATTCTCAGACGAGCAACTCCTCTAGGAGTAGCAAGTCTGTAGCTCTCGTTGTTTTGATGGCCC |
| 107 | Mal-2-7 | AGCGTCTCTCGATCTCATTCTCAATATTGTTTTACTCGTCCAAGTCGCATCCGAAGAAAGCGAGTTGTTTTGATGGCCC |
| 108 | Mal-2-8 | AGCGTCTCTCGATCTCATTCTCAACTTTATCACATCGGAAACAAGGATCAAGAACCATAGAGTTGTTTTGATGGCCC |
| 109 | Mal-2-9 | AGCGTCTCTCGATCTCATTCTCACGTTATACCGTTGTGTGAGGAAACCGAAACACAAGGGCTTGTTGTTTTGATGGCCC |
| 110 | Mal-2-10 | AGCGTCTCTCGATCTCATTCTCATTAATTCACTTAGAGACGAAAGAAAAAGGACTGACCAGGAGTTGTTTTGATGGCCC |
| 111 | Mal-2-11 | AGCGTCTCTCGATCTCATTCTCATTTGTTTAGGCGAGCAAACTACAAAGGTTTGAACGCACTCGTTGTTTTGATGGCCC |
| 112 | Mal-2-12 | AGCGTCTCTCGATCTCATTCTCATTTACTACACTAATCCGGGAAAAAGAACGGAACCGAAGCCGTTGTTTTGATGGCCC |
| 113 | Mal-2-13 | AGCGTCTCTCGATCTCATTCTCACGTCATGCTACTTGATTAAGATCAAAACACAGCCACGCACGTTGTTTTGATGGCCC |
| 114 | Mal-2-14 | AGCGTCTCTCGATCTCATTCTCAGTTATATACAAACACAATTAAACAAGGAATAAAAGTCGAGTTGTTTTGATGGCCC |
| 115 | Mal-2-15 | AGCGTCTCTCGATCTCATTCTCATTATCACGTCTCTGCAAACAAGAAAAAACCAAGGGATCGGGTTGTTTTGATGGCCC |
| 116 | Mal-2-16 | AGCGTCTCTCGATCTCATTCTCACTATACAAACTCGATCGGAATAAAAGTGTTCAAACACAGTTGTTTTGATGGCCC |
| 117 | Mal-2-17 | AGCGTCTCTCGATCTCATTCTCAATTCTTCATCCCCGCAAAACAAAGAACGACAAGCGAAAGTTGTTTTGATGGCCC |
| 118 | Mal-2-18 | AGCGTCTCTCGATCTCATTCTCAAAGGGCTCCGCAAGGAGCAGAAGAGACTCGATTTATATAAGTTGTTTTGATGGCCC |
| 119 | Mal-2-19 | AGCGTCTCTCGATCTCATTCTCATTTACTCGGAAAAAACAGCCAGCGAACCAGCAAGAGCTTAGTTGTTTTGATGGCCC |
| 120 | Mal-2-20 | AGCGTCTCTCGATCTCATTCTCATCTTACCCAAATGAAAACAAATCGGAGGATACAGCGTAGAGTTGTTTTGATGGCCC |
| 121 | Mal-2-21 | AGCGTCTCTCGATCTCATTCTCACCGGTCGAAGGTTCTGGCAAGAACCGAAGAACGAAATCTCGTTGTTTTGATGGCCC |

TABLE 1-continued

List of top sequences from selection experiment.

| SEQ ID NO | Name | Sequence |
|---|---|---|
| 122 | Mal-2-22 | AGCGTCTCTCGATCTCATTCTCACGGAAGAACAACATGACGAAGTGGGAAAGGTATGAGGAGTGTTGTTTTGATGGCCC |
| 123 | Mal-2-23 | AGCGTCTCTCGATCTCATTCTCATTCCTTGTTACACTGCTAGACCAATCATGCAAAACGAGACGTTGTTTTGATGGCCC |
| 124 | Mal-2-24 | AGCGTCTCTCGATCTCATTCTCATTATTTCAACGCAACAACAACCGTCGTGATACAAGATAAGGTTGTTTTGATGGCCC |
| 125 | Mal-2-25 | AGCGTCTCTCGATCTCATTCTCATTCATATGCAATCTCGCAACAAACGACGAACAAAAACGGAGTTGTTTTGATGGCCC |
| 126 | Mal-2-26 | AGCGTCTCTCGATCTCATTCTCAATATTATCCTCATCAGAAAACAGAGCGAAGAAATCAAGCGGTTGTTTTGATGGCCC |
| 127 | Mal-2-27 | AGCGTCTCTCGATCTCATTCTCACCTGCAGCAAGATTCAGCAAGCGCAGCGAGATGAAGCGAGGTTGTTTTGATGGCCC |
| 128 | Mal-2-28 | AGCGTCTCTCGATCTCATTCTCATTGCTCTAATGCGAGTTGAAAACTCACAGGTCTTGGACGAGTTGTTTTGATGGCCC |
| 129 | Mal-2-29 | AGCGTCTCTCGATCTCATTCTCATTATTATCCTTCGATCAAAAAATTAACAAACCACACAAAAGTTGTTTTGATGGCCC |
| 130 | Mal-2-30 | AGCGTCTCTCGATCTCATTCTCACTTAAATTTACAAAAAACGAACCAGCGATCGAAGATAGAGGTTGTTTTGATGGCCC |
| 131 | Mal-2-31 | AGCGTCTCTCGATCTCATTCTCATTCCTTACATATGGCTTCAAGCCTCAAAGCATCTAAACGAGTTGTTTTGATGGCCC |
| 132 | Mal-2-32 | AGCGTCTCTCGATCTCATTCTCATTCAATCACTTCCATCCCCAGAAAAGAAACAACGAAGCTGGTTGTTTTGATGGCCC |
| 133 | Mal-2-33 | AGCGTCTCTCGATCTCATTCTCAATTACACAAGGAATAACCGAGAACAGACGACCGGTGCGAGGTTGTTTTGATGGCCC |
| 134 | Mal-2-34 | AGCGTCTCTCGATCTCATTCTCACTTAAACTACCAAACATAATTTTCAAGCTCCTAATCCCAAGTTGTTTTGATGGCCC |
| 135 | Mal-2-35 | AGCGTCTCTCGATCTCATTCTCAAATTACATTTCATTCCAGCGAAAAATACAGAAAACGTCGAGTTGTTTTGATGGCCC |
| 136 | Mal-2-36 | AGCGTCTCTCGATCTCATTCTCATCTATCCTCTCAAGAAAATACACGAAAACAAACACGAAGAGTTGTTTTGATGGCCC |
| 137 | Mal-2-37 | AGCGTCTCTCGATCTCATTCTCAAGCCTTGCGGACAAAGAGTGAGCGAGGATTGAGTTTACCCGTTGTTTTGATGGCCC |
| 138 | Mal-2-38 | AGCGTCTCTCGATCTCATTCTCAGTTACTTGTTCAACAAACGAGAACAAGGCAGGAAGTTCGAGTTGTTTTGATGGCCC |
| 139 | Mal-2-39 | AGCGTCTCTCGATCTCATTCTCAATTAAGTAATCTACAACGCAAAACAAGCCGCAACGGAGCAGTTGTTTTGATGGCCC |
| 140 | Mal-2-40 | AGCGTCTCTCGATCTCATTCTCATATTTCATCACAATTCAAAACAAGACTGCACGGAAAGCATGTTGTTTTGATGGCCC |
| 141 | Mal-2-41 | AGCGTCTCTCGATCTCATTCTCATTGAAAAGAACGGATCCTACGCGAACCATGGAGAGATCCTGTTGTTTTGATGGCCC |
| 142 | Mal-2-42 | AGCGTCTCTCGATCTCATTCTCATATTACATTTCCAATCGTAACATTGAAACAAATCCCGAAAGTTGTTTTGATGGCCC |
| 143 | Mal-2-43 | AGCGTCTCTCGATCTCATTCTCACTACCACTGCAACGCTAGACTTTGCAGTGTGAACTCGCTTGTTGTTTTGATGGCCC |
| 144 | Mal-2-44 | AGCGTCTCTCGATCTCATTCTCAAAACTTCAATTCAATGCTTCAAAACAGCTATAGAGAACCGGTTGTTTTGATGGCCC |
| 145 | Mal-2-45 | AGCGTCTCTCGATCTCATTCTCATTAATCAAGCAAAAAGAAAGGACGCATATGCTAGCGACGGTTGTTTTGATGGCCC |
| 146 | Mal-2-46 | AGCGTCTCTCGATCTCATTCTCAAACGATTCCGAGGAGGCGAGGAAGAAGTTGCCTACTTATTGTTGTTTTGATGGCCC |
| 147 | Mal-2-47 | AGCGTCTCTCGATCTCATTCTCAACTAAAATTCTCAAACTTCATGCAGCAGAACAAGACCTACGTTGTTTTGATGGCCC |
| 148 | Mal-2-48 | AGCGTCTCTCGATCTCATTCTCACTTATTAAAACTGCAAAAAGACCGAGTTCAGTCGTCGAAGGTTGTTTTGATGGCCC |
| 149 | Mal-2-49 | AGCGTCTCTCGATCTCATTCTCATTTAATTTCAATCTTGAAGAAACAGCAGCGCAAGCGCTGAGTTGTTTTGATGGCCC |
| 150 | Mal-2-50 | AGCGTCTCTCGATCTCATTCTCAATTGTCTTTATTACAGAGAACAACGAGAGCAAGTGCCTCAGTTGTTTTGATGGCCC |
| 151 | Mal-2-51 | AGCGTCTCTCGATCTCATTCTCATTTGACACCCGACCAACTCAGCAGGGTAGACGAAATTAAAGTTGTTTTGATGGCCC |
| 152 | Mal-2-52 | AGCGTCTCTCGATCTCATTCTCAATCTTTTCCGTCAAGCACCAGACAAGCGAAAGAAGGTCTAGTTGTTTTGATGGCCC |
| 153 | Mal-2-53 | AGCGTCTCTCGATCTCATTCTCATATTTAACTCACATCCTGAGAAACAACTAACGACACATAAGTTGTTTTGATGGCCC |
| 154 | Mal-2-54 | AGCGTCTCTCGATCTCATTCTCATCTGTGATAATAATCAAATTATAAGCTGATCGAAGACCGGGTTGTTTTGATGGCCC |
| 155 | Mal-2-55 | AGCGTCTCTCGATCTCATTCTCACTTAATAACTGTTTCAAAGCAAGATCGACCGAAAGGGGATGTTGTTTTGATGGCCC |
| 156 | Mal-2-56 | AGCGTCTCTCGATCTCATTCTCACCAGTACAAAAATAAGACACAAACCCCAGGCCTCGCTTGAGTTGTTTTGATGGCCC |
| 157 | Mal-2-57 | AGCGTCTCTCGATCTCATTCTCAAGTCCGAACAACCGGAAAGAGCCAACCGGCAACGCTCTTCGTTGTTTTGATGGCCC |
| 158 | Mal-2-58 | AGCGTCTCTCGATCTCATTCTCACCTTTTGCAAACACATCTCTAATTAAACGAACCAGGCTCGTTGTTTTGATGGCCC |

TABLE 1-continued

List of top sequences from selection experiment.

| SEQ ID NO | Name | Sequence |
|---|---|---|
| 159 | Mal-2-59 | AGCGTCTCTCGATCTCATTCTCAAGAGCCCGATTGCAGAATTCGGCTCGGTTTAATTAAGTCGGTTGTTTTGATGGCCC |
| 160 | Mal-2-60 | AGCGTCTCTCGATCTCATTCTCAACGAAAGAGACGAGAATAGATTACACCAGCCCTCTTGTTTGTTGTTTTGATGGCCC |
| 161 | Mal-2-61 | AGCGTCTCTCGATCTCATTCTCATTATACTTGAACAAAACCGAAATTACGATCACGGCAGATCGTTGTTTTGATGGCCC |
| 162 | Mal-2-62 | AGCGTCTCTCGATCTCATTCTCATACTTGTCCTTAATTAAAAGCAGAAAGAAATAACGAGTAGTTGTTTTGATGGCCC |
| 163 | Mal-2-63 | AGCGTCTCTCGATCTCATTCTCATGCCCGGAGAAACCGAAGGCGACTTAAATATAAACTCCTTGTTGTTTTGATGGCCC |
| 164 | Mal-2-64 | AGCGTCTCTCGATCTCATTCTCAGGTCACGCGCTGTTGCAAGCAATGAGCGCGACTGACTCTAGTTGTTTTGATGGCCC |
| 165 | Mal-2-65 | AGCGTCTCTCGATCTCATTCTCAGAGATAATCTCTGTGAAGAAAGAAACGGATTTACTTGCTTGTTGTTTTGATGGCCC |
| 166 | Mal-2-66 | AGCGTCTCTCGATCTCATTCTCACTATCACTGGAAGACAAATATAGAGTCTACAAACGATGAAGTTGTTTTGATGGCCC |
| 167 | Mal-2-67 | AGCGTCTCTCGATCTCATTCTCAACTCTCAACATCTGGAGTCAAGAACTTGATGAGCAATGATGTTGTTTTGATGGCCC |
| 168 | Mal-2-68 | AGCGTCTCTCGATCTCATTCTCACAAAGAACAGAAAGAGGAAGAAATGACGAGGCTGGAGTTTGTTGTTTTGATGGCCC |
| 169 | Mal-2-69 | AGCGTCTCTCGATCTCATTCTCATTATTTACTTCACTCGAAACAACATACGGGAATCCCGGCAGTTGTTTTGATGGCCC |
| 170 | Mal-2-70 | AGCGTCTCTCGATCTCATTCTCATTTTCACATCCATCAAAGGATGAAGAATTCATATCGATCGGTTGTTTTGATGGCCC |
| 171 | Mal-2-71 | AGCGTCTCTCGATCTCATTCTCAAGCTACGAACGTAGCGAAAAGTAGAGCTCTTGTTATACCTGTTGTTTTGATGGCCC |
| 172 | Mal-2-72 | AGCGTCTCTCGATCTCATTCTCAATCTTACGTTCAACGACCAAAACAAAGGAAAGACGTGCTCGTTGTTTTGATGGCCC |
| 173 | Mal-2-73 | AGCGTCTCTCGATCTCATTCTCAATCTTATATCTAACAAATGAGTAACACTTAACACACCTCAGTTGTTTTGATGGCCC |
| 174 | Mal-2-74 | AGCGTCTCTCGATCTCATTCTCAAAGCCTTCTACATTCAGCACAAACCACAAAGACCACCCATGTTGTTTTGATGGCCC |
| 175 | Mal-2-75 | AGCGTCTCTCGATCTCATTCTCAACATAGTTTACATTCCTTATAACAACATCTCAAAACAATGGTTGTTTTGATGGCCC |
| 176 | Mal-2-76 | AGCGTCTCTCGATCTCATTCTCATATACTTCATATAGCAAAAGTCTGAACCGACAGGGACAGGTTGTTTTGATGGCCC |
| 177 | Mal-2-77 | AGCGTCTCTCGATCTCATTCTCAGGCTAGAGCGAATGATGATTCGACTCCAACCGGTGCACTAGTTGTTTTGATGGCCC |
| 178 | Mal-2-78 | AGCGTCTCTCGATCTCATTCTCATACTACATGCGTATTCGAAACGATAATACGCAATAACTCGGTTGTTTTGATGGCCC |
| 179 | Mal-2-79 | AGCGTCTCTCGATCTCATTCTCACAGTCGACTGAATGGACTTGTTAAAACGGAGCAAGGTATAGTTGTTTTGATGGCCC |
| 180 | Mal-2-80 | AGCGTCTCTCGATCTCATTCTCACGCAACAACACAGTTCATAGCCGAGGACCGTCCTCTTGCGGTTGTTTTGATGGCCC |
| 181 | Mal-2-81 | AGCGTCTCTCGATCTCATTCTCATCATTTATCCGAAAAGAAAAAACAAGCGGCTTGAGCACGAGTTGTTTTGATGGCCC |
| 182 | Mal-2-82 | AGCGTCTCTCGATCTCATTCTCATTTAATTCACTGCAGAACAACAACGGAAACTAGACGCCAAGTTGTTTTGATGGCCC |
| 183 | Mal-2-83 | AGCGTCTCTCGATCTCATTCTCAAACGAATGGTCCATCGGTGTTACTTAAGAATATGCATGACGTTGTTTTGATGGCCC |
| 184 | Mal-2-84 | AGCGTCTCTCGATCTCATTCTCAATTTACCTGTTACTAGCAACTGAAACAAAGAACATAAGAAGTTGTTTTGATGGCCC |
| 185 | Mal-2-85 | AGCGTCTCTCGATCTCATTCTCACGTTAACCTTTACGAATAGATAACAGAACTAAATCTAGAAGTTGTTTTGATGGCCC |
| 186 | Mal-2-86 | AGCGTCTCTCGATCTCATTCTCACTTGCTTGGTTAGTTCCGCAAAAAGATGGACGAAGGACAGGTTGTTTTGATGGCCC |
| 187 | Mal-2-87 | AGCGTCTCTCGATCTCATTCTCACACATTTTACACGCATACATCACGGATCGAAATACCACCGGTTGTTTTGATGGCCC |
| 188 | Mal-2-88 | AGCGTCTCTCGATCTCATTCTCACATTAATCTCGCTTTAATACAAAACTGCAATCGATAATCGGTTGTTTTGATGGCCC |
| 189 | Mal-2-89 | AGCGTCTCTCGATCTCATTCTCATTTAGCTCTTCACTTGAAAAATCCATACAAAGAAATAAGAGTTGTTTTGATGGCCC |
| 190 | Mal-2-90 | AGCGTCTCTCGATCTCATTCTCAACGCTAGTACATACCCGATGGAAGTACTAGTGCTGATCTTGTTTTGATGGCCC |
| 191 | Mal-2-91 | AGCGTCTCTCGATCTCATTCTCAATTACGTACCTAGACCACAACATAGCATCGGTAGCAGCTAGTTGTTTTGATGGCCC |
| 192 | Mal-2-92 | AGCGTCTCTCGATCTCATTCTCACTTGTTCATGCACAAAGCAAACAACCCGAGACTCGTAGCAGTTGTTTTGATGGCCC |
| 193 | Mal-2-93 | AGCGTCTCTCGATCTCATTCTCATAATCATCTTCAAATAACAAAACATGAAAAGTACCGGACGTTGTTTTGATGGCCC |
| 194 | Mal-2-94 | AGCGTCTCTCGATCTCATTCTCATTTCTACTATTCAAAAACCCGAAAGAAAAACTGAAAGCCCGTTGTTTTGATGGCCC |
| 195 | Mal-2-95 | AGCGTCTCTCGATCTCATTCTCACTTAAATTTACAAAAAACGAACCAGTGATCGAAGATAGAGGTTGTTTTGATGGCCC |
| 196 | Mal-2-96 | AGCGTCTCTCGATCTCATTCTCAGAATCCACAAGCATCAACGGCGATAGCTAATAAAATGCACGTTGTTTTGATGGCCC |

TABLE 1-continued

List of top sequences from selection experiment.

| SEQ ID NO | Name | Sequence |
|---|---|---|
| 197 | Mal-2-97 | AGCGTCTCTCGATCTCATTCTCAAAACGTTTTATAGATATCAAGGAACCATAGTATCAGACAAGTTGTTTTGATGGCCC |
| 198 | Mal-2-98 | AGCGTCTCTCGATCTCATTCTCAAAAGGTGAGGACAGAACCTATGATAGCACGGTTTAATCATGTTGTTTTGATGGCCC |
| 199 | Mal-2-99 | AGCGTCTCTCGATCTCATTCTCACGGACTAATCTAAGAGCTTAAGTACGCGTAGATTAGCACGGTTGTTTTGATGGCCC |
| 200 | Mal-2-100 | AGCGTCTCTCGATCTCATTCTCATTCCTGCTTTACGCACCAAACAATCACGAGCACCAAGAGTGTTGTTTTGATGGCCC |
| 201 | Mal-3-1 | AGCGTCTCTCGATCTCATTCTCAGAACGGAATCGACACATTCACGACGAAGAGAATAGAGGCAGTTGTTTTGATGGCCC |
| 202 | Mal-3-2 | AGCGTCTCTCGATCTCATTCTCACGAAGAGTGGTTGATGGAATCGAGGAGCGCGAGCCCAGATGTTGTTTTGATGGCCC |
| 203 | Mal-3-3 | AGCGTCTCTCGATCTCATTCTCACACGGTGTTCCAAGAGTGAGTAAGAGAACGAAAGGGAAATGTTGTTTTGATGGCCC |
| 204 | Mal-3-4 | AGCGTCTCTCGATCTCATTCTCAATGGAGATCTAGTAGCGCGGAACGACAAAACGGATCACGAGTTGTTTTGATGGCCC |
| 205 | Mal-3-5 | AGCGTCTCTCGATCTCATTCTCAAATTACATTTCATTCCAGCGAAAATACAGAAAACGTCGAGTTGTTTTGATGGCCC |
| 206 | Mal-3-6 | AGCGTCTCTCGATCTCATTCTCACTCACCTTAAACTTTAACGAATTAAAAAACAAGACCGGCAGTTGTTTTGATGGCCC |
| 207 | Mal-3-7 | AGCGTCTCTCGATCTCATTCTCAGGGTGGAAATGAAATCGGAGATGCGGCTGATGTCAGAACGGTTGTTTTGATGGCCC |
| 208 | Mal-3-8 | AGCGTCTCTCGATCTCATTCTCAGGACGGAATCGACACATTCACGACGAAGAGAATAGAGGCAGTTGTTTTGATGGCCC |
| 209 | Mal-3-9 | AGCGTCTCTCGATCTCATTCTCATCCGACCGGCGTGAAAGGGATCCAGAACGCGACCCAAAAGTTGTTTTGATGGCCC |
| 210 | Mal-3-10 | AGCGTCTCTCGATCTCATTCTCAATGTGGTCGAGTGCACGCGGACCAAAGTAAGATCGGACGAGTTGTTTTGATGGCCC |
| 211 | Mal-3-11 | AGCGTCTCTCGATCTCATTCTCATTCATTAAATTCAAACAAAAGAAACGGTGCGACAGACCAGGTTGTTTTGATGGCCC |
| 212 | Mal-3-12 | AGCGTCTCTCGATCTCATTCTCAGAACATTCCGAAGCGAATGTACGGAAAAACGGAGATCGCTGTTGTTTTGATGGCCC |
| 213 | Mal-3-13 | AGCGTCTCTCGATCTCATTCTCACCTAAGGGAAACATGAGTCGGAGAAGCGGACAAACCATAAGTTGTTTTGATGGCCC |
| 214 | Mal-3-14 | AGCGTCTCTCGATCTCATTCTCAAAAATGATGATCGGCAGAAGCGCCAAGTAAGAAGCGATAGGTTGTTTTGATGGCCC |
| 215 | Mal-3-15 | AGCGTCTCTCGATCTCATTCTCATGAGGTGAAGAAACGCGCCAGTCAAAGCGCTACCCGAGGAGTTGTTTTGATGGCCC |
| 216 | Mal-3-16 | AGCGTCTCTCGATCTCATTCTCACACCCGTTGAGAAAAAGATTGAAAGAGGCGACGCACCCAAGTTGTTTTGATGGCCC |
| 217 | Mal-3-17 | AGCGTCTCTCGATCTCATTCTCATAGACGAACGAACCGAAGGGTCAGAGTCAAGCTTACTCGTGTTGTTTTGATGGCCC |
| 218 | Mal-3-18 | AGCGTCTCTCGATCTCATTCTCAGCGGGTCTTAAGAAAATGAGAGAGAAGCGCGAGCCAGACGTTGTTTTGATGGCCC |
| 219 | Mal-3-19 | AGCGTCTCTCGATCTCATTCTCACACCCGCATGGTGTATGGATGATGATCAGGAGATGCGACCGTTGTTTTGATGGCCC |
| 220 | Mal-3-20 | AGCGTCTCTCGATCTCATTCTCAGCAGCGGAGAACGATGTGCAGGAGATGCGCGCCAAGCAAGTTGTTTTGATGGCCC |
| 221 | Mal-3-21 | AGCGTCTCTCGATCTCATTCTCATTATACTTGAACAAAACCGAAATTACGATCACGGCAGATCGTTGTTTTGATGGCCC |
| 222 | Mal-3-22 | AGCGTCTCTCGATCTCATTCTCATGAGAAAGAGCGCGCGAACATGACGAGAGAAACGGCACGAGTTGTTTTGATGGCCC |
| 223 | Mal-3-23 | AGCGTCTCTCGATCTCATTCTCAACTACATCTATACACTGACAAAACAGTCTGACGAAAGCCAGTTGTTTTGATGGCCC |
| 224 | Mal-3-24 | AGCGTCTCTCGATCTCATTCTCAACGTTTTGTAGTGAATGAGGGCGAGTGGCGCGGCTAAACCGTTGTTTTGATGGCCC |
| 225 | Mal-3-25 | AGCGTCTCTCGATCTCATTCTCAGAACGAGTCGGGTGATGCGGATAGCCACTAGCGAAAACTGGTTGTTTTGATGGCCC |
| 226 | Mal-3-26 | AGCGTCTCTCGATCTCATTCTCAATAAGACGTACGAGATCAGGCGGAACGCGAACCATAGAACGTTGTTTTGATGGCCC |
| 227 | Mal-3-27 | AGCGTCTCTCGATCTCATTCTCAGTTGAGTACAAACGGAAAATGCGAGAGATGCGGGAGTCGAGTTGTTTTGATGGCCC |
| 228 | Mal-3-28 | AGCGTCTCTCGATCTCATTCTCAATTACGAGAACAGAGAAGCGCGGATTCCACCAAAGAAAGAGTTGTTTTGATGGCCC |
| 229 | Mal-3-29 | AGCGTCTCTCGATCTCATTCTCAAGGGAGAAGGTGATCGGAAAAAACCCGAAGCGACACCAAGTTGTTTTGATGGCCC |
| 230 | Mal-3-30 | AGCGTCTCTCGATCTCATTCTCATTAAGAATCGATGAGAGAGCGGCGCAGAAGCCACCAACGGGTTGTTTTGATGGCCC |
| 231 | Mal-3-31 | AGCGTCTCTCGATCTCATTCTCATGGGAGAGAGTTAAGGAGAAGCGAGATAGCAAAACGTAGGTTGTTTTGATGGCCC |
| 232 | Mal-3-32 | AGCGTCTCTCGATCTCATTCTCAACGAAGTTGTAACGAACCGAGGGATGCGAGCAAAACGTTGTTGTTTTGATGGCCC |
| 233 | Mal-3-33 | AGCGTCTCTCGATCTCATTCTCAACGAGAAGGAGTCGGTCGGACGCGACAACACAAGCGCGTAGTTGTTTTGATGGCCC |

TABLE 1-continued

List of top sequences from selection experiment.

| SEQ ID NO | Name | Sequence |
|---|---|---|
| 234 | Mal-3-34 | AGCGTCTCTCGATCTCATTCTCAATGAGTGGATCGGTAGAAGCGAGGCTATAAGTCAGAACAGGTTGTTTTGATGGCCC |
| 235 | Mal-3-35 | AGCGTCTCTCGATCTCATTCTCAATTCTTCATCCCCGCAAAAACAAAGAACGACAAGCGAAAAGTTGTTTTGATGGCCC |
| 236 | Mal-3-36 | AGCGTCTCTCGATCTCATTCTCAGTGTCGAAGAGAAGGAGGCGAAGAGAGTACGAGCACAAGTTGTTTTGATGGCCC |
| 237 | Mal-3-37 | AGCGTCTCTCGATCTCATTCTCACTTTACTAGTAACCCCAGCAAAAGAAGATGCGAACAAGGAGTTGTTTTGATGGCCC |
| 238 | Mal-3-38 | AGCGTCTCTCGATCTCATTCTCACAGAGAGAGAAATCCGAGAGGTCGCGGCCAGCTGCGGAGCGTTGTTTTGATGGCCC |
| 239 | Mal-3-39 | AGCGTCTCTCGATCTCATTCTCAGACATGAGATCACAGTCAAGCGGCGCGCAAATAGGAACTTGTTGTTTTGATGGCCC |
| 240 | Mal-3-40 | AGCGTCTCTCGATCTCATTCTCACCTGCAGCAAGATTCAGCAAGCGCAGCGAGATGAAGCGAGGTTGTTTTGATGGCCC |
| 241 | Mal-3-41 | AGCGTCTCTCGATCTCATTCTCATAATTTACATACACTGAAAAAAGCGAAACAAGACGTAGAGGTTGTTTTGATGGCCC |
| 242 | Mal-3-42 | AGCGTCTCTCGATCTCATTCTCATGAGAGTAGAGGAATCGCGCCCCAGAGAAAGATCGAAGAGGTTGTTTTGATGGCCC |
| 243 | Mal-3-43 | AGCGTCTCTCGATCTCATTCTCACTTGTCGTGCGAAGCGCGAAAAGGGAAGCTTAACCTTGATGTTGTTTTGATGGCCC |
| 244 | Mal-3-44 | AGCGTCTCTCGATCTCATTCTCATCGGGTCAGAGTGATGAGAAGGTCAAGAATCAACTCGCGTGTTGTTTTGATGGCCC |
| 245 | Mal-3-45 | AGCGTCTCTCGATCTCATTCTCAACCTTGTCTATTCATGATCAAAATAAAAAATGCGAAGCGAGTTGTTTTGATGGCCC |
| 246 | Mal-3-46 | AGCGTCTCTCGATCTCATTCTCAGAAGAATGAAGCGGAGTAGCGAGCAGCAAGAGCCGTTGCGGTTGTTTTGATGGCCC |
| 247 | Mal-3-47 | AGCGTCTCTCGATCTCATTCTCATGCTATAAGCTGATGAGATGAGTGCGCGACAGAAGGAAAGTTGTTTTGATGGCCC |
| 248 | Mal-3-48 | AGCGTCTCTCGATCTCATTCTCAAAGGAGGTCGAAAGGACGAGCAGGCAATCAAAGTAGAGCTGTTGTTTTGATGGCCC |
| 249 | Mal-3-49 | AGCGTCTCTCGATCTCATTCTCAAGCGAGGTCGAGGGCAGCGGTCAAAGATCAAACGGTTGAAGTTGTTTTGATGGCCC |
| 250 | Mal-3-50 | AGCGTCTCTCGATCTCATTCTCAGTAATGGGAGCGAGCAGCGAGAGCATCGAAACGAGAAACAGTTGTTTTGATGGCCC |
| 251 | Mal-3-51 | AGCGTCTCTCGATCTCATTCTCATATGCTAGCAGAAGAGATGAGCGCAAGACGCGGGCGAACCGTTGTTTTGATGGCCC |
| 252 | Mal-3-52 | AGCGTCTCTCGATCTCATTCTCATGGACAATGGAAGGAGACCGGAGTAGCGCGGCGGAAACGTGTTGTTTTGATGGCCC |
| 253 | Mal-3-53 | AGCGTCTCTCGATCTCATTCTCACGAGAGAGGAGAGCTAGAGAGGCGGACCGCCAGCGAAAAGTTGTTTTGATGGCCC |
| 254 | Mal-3-54 | AGCGTCTCTCGATCTCATTCTCAGACCGAGTGCAAGCGACCGGCAAAAACAAAATGGAACTCCGTTGTTTTGATGGCCC |
| 255 | Mal-3-55 | AGCGTCTCTCGATCTCATTCTCAGATGTGGACAGAGAACGCGACCAAACAAAATCGCGAAAGAGTTGTTTTGATGGCCC |
| 256 | Mal-3-56 | AGCGTCTCTCGATCTCATTCTCATCCAGACTGTGAATGGCAAATAGAGAGCGCGGGCAGTAAGGTTGTTTTGATGGCCC |
| 257 | Mal-3-57 | AGCGTCTCTCGATCTCATTCTCATTGACAAGGCGAGGAAACGAGACCTGGCATACTCTTGCGTGTTGTTTTGATGGCCC |
| 258 | Mal-3-58 | AGCGTCTCTCGATCTCATTCTCAATTTACCTGTTACTAGCAACTGAAACAAAGAACATAAGAAGTTGTTTTGATGGCCC |
| 259 | Mal-3-59 | AGCGTCTCTCGATCTCATTCTCACTTTAATCTAGTTATCCGAAGCAGAACAGAAATCCGACAGGTTGTTTTGATGGCCC |
| 260 | Mal-3-60 | AGCGTCTCTCGATCTCATTCTCAATGAGCGAGGAGGTGTAACGCGCAGAGGAAAAAGACGAAGTTGTTTTGATGGCCC |
| 261 | Mal-3-61 | AGCGTCTCTCGATCTCATTCTCAATTCACTTGCTCCAAAAAGCAAAAGCAATCGGTCGACCGAGTTGTTTTGATGGCCC |
| 262 | Mal-3-62 | AGCGTCTCTCGATCTCATTCTCAATGACAGCGAAGAGCGTCTAGAAGGAACAACCAGAAAGCTGTTGTTTTGATGGCCC |
| 263 | Mal-3-63 | AGCGTCTCTCGATCTCATTCTCAAACTCAGATGAGAAGCAGACGAGAACAGTGATGCCGTAGAGTTGTTTTGATGGCCC |
| 264 | Mal-3-64 | AGCGTCTCTCGATCTCATTCTCAATGAGTGTTGAGGCGACGAGTAGCGAGAACAAAGCCAAGCGTTGTTTTGATGGCCC |
| 265 | Mal-3-65 | AGCGTCTCTCGATCTCATTCTCACTTAAATTTACAAAAAACGAACCAGTGATCGAAGATAGAGGTTGTTTTGATGGCCC |
| 266 | Mal-3-66 | AGCGTCTCTCGATCTCATTCTCACTTCTAATCTGAAAACAAGCCGATGGATGACCACCAAGAGGTTGTTTTGATGGCCC |
| 267 | Mal-3-67 | AGCGTCTCTCGATCTCATTCTCACGATCGGGAAAAGCGCGAGCCAAGCAATACAAGTAGTAAGGTTGTTTTGATGGCCC |
| 268 | Mal-3-68 | AGCGTCTCTCGATCTCATTCTCATTGCTTAATTCAAACAGATCAAAATAAAGCACATACAGCGGTTGTTTTGATGGCCC |
| 269 | Mal-3-69 | AGCGTCTCTCGATCTCATTCTCACGGCGGGAGAAAAAATCAAGAGAAGCGCACATCAGAAGAAGTTGTTTTGATGGCCC |
| 270 | Mal-3-70 | AGCGTCTCTCGATCTCATTCTCAGCGTCACTGAGGAGAGATCCGACGAAGAGCAGATAAAACGGTTGTTTTGATGGCCC |
| 271 | Mal-3-71 | AGCGTCTCTCGATCTCATTCTCATAAGAGAGAGGTCGCGGTGATAAACAAGCCAAGAAGAGTAGTTGTTTTGATGGCCC |

TABLE 1-continued

List of top sequences from selection experiment.

| SEQ ID NO | Name | Sequence |
|---|---|---|
| 272 | Mal-3-72 | AGCGTCTCTCGATCTCATTCTCATTATATTCACAAAGAAAACAGAAAGCTGCTCGCTAGGCAGGTTGTTTTGATGGCCC |
| 273 | Mal-3-73 | AGCGTCTCTCGATCTCATTCTCATTCACTGCTCCAAAAAGCTTAGAAAACAAAGACCGGACAGGTTGTTTTGATGGCCC |
| 274 | Mal-3-74 | AGCGTCTCTCGATCTCATTCTCATTTCAAACTTATTTACGGAAAACGACGGATTCGAAAAGCTGTTGTTTTGATGGCCC |
| 275 | Mal-3-75 | AGCGTCTCTCGATCTCATTCTCAAAAGGAGAGAAGAGCAAGAAGGTAACGCGAACGATCATAAGTTGTTTTGATGGCCC |
| 276 | Mal-3-76 | AGCGTCTCTCGATCTCATTCTCAAAGAAGAAGAGCGGTGAGGCAAGACGCGGCACGAGGAAATGTTGTTTTGATGGCCC |
| 277 | Mal-3-77 | AGCGTCTCTCGATCTCATTCTCACATTATGGTGAGGAAAGATCGCCGCGGCCCAATATCAAAGTTGTTTTGATGGCCC |
| 278 | Mal-3-78 | AGCGTCTCTCGATCTCATTCTCAGTGTAAACGATGAGTCGAGGGTGCGACAAGCAAGAAGAGAGTTGTTTTGATGGCCC |
| 279 | Mal-3-79 | AGCGTCTCTCGATCTCATTCTCATGGGAACGTGAGTAGACTGATGAGAGAGCGCGGGCACTCAGTTGTTTTGATGGCCC |
| 280 | Mal-3-80 | AGCGTCTCTCGATCTCATTCTCACAATAGGTGTGAAAGAGAAAGAGCGGCGACCTAGATGACTGTTGTTTTGATGGCCC |
| 281 | Mal-3-81 | AGCGTCTCTCGATCTCATTCTCACAGGATAGGAGAACACGAGATGTGGAGAGAACCAAATCAAGTTGTTTTGATGGCCC |
| 282 | Mal-3-82 | AGCGTCTCTCGATCTCATTCTCAGAGCGACCGTAGCCACAAGGCAAGGGAGCCTGGATTTCTCGTTGTTTTGATGGCCC |
| 283 | Mal-3-83 | AGCGTCTCTCGATCTCATTCTCATAGGTGATGGGAATGCGGATCGATGGTGACGCGGCCTCGAGTTGTTTTGATGGCCC |
| 284 | Mal-3-84 | AGCGTCTCTCGATCTCATTCTCATTTATTCATTCAAGGAAAAACACAAACAGAAAATAGAGCAGTTGTTTTGATGGCCC |
| 285 | Mal-3-85 | AGCGTCTCTCGATCTCATTCTCAAAATGGAGAGAGAGAGCGCCATCGTGCGAAGCAATACGGAGTTGTTTTGATGGCCC |
| 286 | Mal-3-86 | AGCGTCTCTCGATCTCATTCTCAACGAGAAGCCAGTTCGCGACCAACAAAGAGAGGCGAGAAGGTTGTTTTGATGGCCC |
| 287 | Mal-3-87 | AGCGTCTCTCGATCTCATTCTCAACTTAACATAAATTTCAGTCTAAACAAGATCCGGAACGGGGTTGTTTTGATGGCCC |
| 288 | Mal-3-88 | AGCGTCTCTCGATCTCATTCTCAAGAATGCGTAGCGAGAGATCAAGCGGGATCAAAGCCTGTCGTTGTTTTGATGGCCC |
| 289 | Mal-3-89 | AGCGTCTCTCGATCTCATTCTCAAGGGAGGAGTGTGATCAGAAGTCGCGGAACATCAGCATCGGTTGTTTTGATGGCCC |
| 290 | Mal-3-90 | AGCGTCTCTCGATCTCATTCTCAGAGAGAGACCGCGACAACAAAGAACTTAGGACCGGAACGCGTTGTTTTGATGGCCC |
| 291 | Mal-3-91 | AGCGTCTCTCGATCTCATTCTCAGGGAGGATAACGTTCGACCGAAAATGCTGCAGAGACGCGGGTTGTTTTGATGGCCC |
| 292 | Mal-3-92 | AGCGTCTCTCGATCTCATTCTCAGTAGGACAGAAATGAGGTCAGAAGAAGCGAGGACCTGAAAGTTGTTTTGATGGCCC |
| 293 | Mal-3-93 | AGCGTCTCTCGATCTCATTCTCAAAATACAGTGAGGAGAGAGATTTGAATAGACGCGGAACCAGTTGTTTTGATGGCCC |
| 294 | Mal-3-94 | AGCGTCTCTCGATCTCATTCTCAAGGTTGCAGAGGCAATGTGAGAATGGGCCGAGATGCGTGGGTTGTTTTGATGGCCC |
| 295 | Mal-3-95 | AGCGTCTCTCGATCTCATTCTCAGGGTGGAATCCTTAGAGAAATCGAAAGGAGAGACCAGCATGTTGTTTTGATGGCCC |
| 296 | Mal-3-96 | AGCGTCTCTCGATCTCATTCTCAGTAATAACTGGGTTTGAGACGTGGAAAGCGCGGTATCAAAGTTGTTTTGATGGCCC |
| 297 | Mal-3-97 | AGCGTCTCTCGATCTCATTCTCAGTTAATTATTATTCCAAAAAACGAGCGAGGGACAAGCGATGTTGTTTTGATGGCCC |
| 298 | Mal-3-98 | AGCGTCTCTCGATCTCATTCTCAACAACTGCGATATGGTCACAAAGTGAGACCTCAGTGTATGGTTGTTTTGATGGCCC |
| 299 | Mal-3-99 | AGCGTCTCTCGATCTCATTCTCAATATTGTTTTACTCGTCCAAGTCGCATCCGAAGAAAGCGAGTTGTTTTGATGGCCC |
| 300 | Mal-3-100 | AGCGTCTCTCGATCTCATTCTCACAGAGAACGCGCATAGAGAAGCGGCCGAACAATGCAAATTGTTGTTTTGATGGCCC |
| 301 | Mal-4-1 | AGCGTCTCTCGATCTCATTCTCAAATTACATTTCATTCCAGCGAAAATACAGAAAACGTCGAGTTGTTTTGATGGCCC |
| 302 | Mal-4-2 | AGCGTCTCTCGATCTCATTCTCAGTCTGTTCAATCCACAAGAGAAACAGGATCGCGAAGCCAGGTTGTTTTGATGGCCC |
| 303 | Mal-4-3 | AGCGTCTCTCGATCTCATTCTCAGTTAATTATTATTCCAAAAAACGAGCGAGGGACAAGCGATGTTGTTTTGATGGCCC |
| 304 | Mal-4-4 | AGCGTCTCTCGATCTCATTCTCATATTACATTTCCAATCGTAACATTGAAACAAATCCCGAAAGTTGTTTTGATGGCCC |
| 305 | Mal-4-5 | AGCGTCTCTCGATCTCATTCTCAATTCACTTGCTCCAAAAAGCAAAGCAATCGGTCGACCGAGTTGTTTTGATGGCCC |
| 306 | Mal-4-6 | AGCGTCTCTCGATCTCATTCTCATCTCGTAAACAAAAGAAACAAAATGGACGACGACCGACAGGTTGTTTTGATGGCCC |
| 307 | Mal-4-7 | AGCGTCTCTCGATCTCATTCTCACACAAAACTCGATCTTGATTATTAACAACCGGAAACCGCAGTTGTTTTGATGGCCC |
| 308 | Mal-4-8 | AGCGTCTCTCGATCTCATTCTCACGTTAAGCGAGGAAACGAAGCGAAACTGAGATACTTGCTTGTTGTTTTGATGGCCC |

TABLE 1-continued

List of top sequences from selection experiment.

| SEQ ID NO | Name | Sequence |
|---|---|---|
| 309 | Mal-4-9 | AGCGTCTCTCGATCTCATTCTCATTGCTTAATTCAAACAGATCAAAATAAAGCACATACAGCGGTTGTTTTGATGGCCC |
| 310 | Mal-4-10 | AGCGTCTCTCGATCTCATTCTCATAATTTTCACCTCACAAGATAAAACCGAACGAACCAATGCGTTGTTTTGATGGCCC |
| 311 | Mal-4-11 | AGCGTCTCTCGATCTCATTCTCATTCCTTGTTACACTGCTAGACCAATCATGCAAAACGAGACGTTGTTTTGATGGCCC |
| 312 | Mal-4-12 | AGCGTCTCTCGATCTCATTCTCATTTTTAAAAGGGAACCGAAGCGAAGTGTGAGGTGAACCGAGTTGTTTTGATGGCCC |
| 313 | Mal-4-13 | AGCGTCTCTCGATCTCATTCTCATTCACTGCTCCAAAAAGCTTAGAAAACAAAGACCGGACAGGTTGTTTTGATGGCCC |
| 314 | Mal-4-14 | AGCGTCTCTCGATCTCATTCTCACTACACAAGCGAACGAAAGAGAGCGCTGTAGCCCTGCTTACTTGTTTTGATGGCCC |
| 315 | Mal-4-15 | AGCGTCTCTCGATCTCATTCTCAACTTAACATAAATTTCAGTCTAAACAAGATCCGGAACGGGGTTGTTTTGATGGCCC |
| 316 | Mal-4-16 | AGCGTCTCTCGATCTCATTCTCATACATTGATTCTGAAAACAAAACCAAAGCCAAACGGATCTGTTGTTTTGATGGCCC |
| 317 | Mal-4-17 | AGCGTCTCTCGATCTCATTCTCAACCTTGTCTATTCATGATCAAAATAAAAATGCGAAGCGAGTTGTTTTGATGGCCC |
| 318 | Mal-4-18 | AGCGTCTCTCGATCTCATTCTCACTTTCAATCAAATAAAAACAAGCTCGTTCGCTAGGTAAGGGTTGTTTTGATGGCCC |
| 319 | Mal-4-19 | AGCGTCTCTCGATCTCATTCTCAGATAAGATCGTAGTTAACTCGATTTTACTTGAACACACCAGTTGTTTTGATGGCCC |
| 320 | Mal-4-20 | AGCGTCTCTCGATCTCATTCTCATCATTCCAAATTTACTAACAGAAAAAAGAGACGGAATCGGTTGTTTTGATGGCCC |
| 321 | Mal-4-21 | AGCGTCTCTCGATCTCATTCTCATTTACATTCTTCGATCAAGACAACAACAACCTAAATAAGAGTTGTTTTGATGGCCC |
| 322 | Mal-4-22 | AGCGTCTCTCGATCTCATTCTCAAGGACAAGGAATGAGACCGCAGTTAATTCATTTATCATCTGTTGTTTTGATGGCCC |
| 323 | Mal-4-23 | AGCGTCTCTCGATCTCATTCTCACTCACCTTAAACTTTAACGAATTAAAAAACAAGACCGGCAGTTGTTTTGATGGCCC |
| 324 | Mal-4-24 | AGCGTCTCTCGATCTCATTCTCAAAGCGAGGAACAACAGACCGAGCGGGTTAATTTAAGATTACTTGTTTTGATGGCCC |
| 325 | Mal-4-25 | AGCGTCTCTCGATCTCATTCTCATTAATCTACTAGAAGAAAAGCAAGACGGAACGGAAGCTTGGTTGTTTTGATGGCCC |
| 326 | Mal-4-26 | AGCGTCTCTCGATCTCATTCTCACCGGTCGAAGGTTCTGGCAAGAACCGAAGAACGAAATCTCGTTGTTTTGATGGCCC |
| 327 | Mal-4-27 | AGCGTCTCTCGATCTCATTCTCATTTTCACATTCTCCGCCCAGACAAAAAAAGAAGAGACCCAGTTGTTTTGATGGCCC |
| 328 | Mal-4-28 | AGCGTCTCTCGATCTCATTCTCACTCTTCTTCCAAATAATAACGAGACGGTCAAAGACCAAACGTTGTTTTGATGGCCC |
| 329 | Mal-4-29 | AGCGTCTCTCGATCTCATTCTCAAGTCATTTAACCCGGAAACAAGACGCGCAAATACAAGCGAGTTGTTTTGATGGCCC |
| 330 | Mal-4-30 | AGCGTCTCTCGATCTCATTCTCATAAATAATTATTCAACAGAAAAATAAAATCAAAGTACCTCGTTGTTTTGATGGCCC |
| 331 | Mal-4-31 | AGCGTCTCTCGATCTCATTCTCAATACATACTATAACAAGTAGAAAACAAGCCGAGCAGGTAGGTTGTTTTGATGGCCC |
| 332 | Mal-4-32 | AGCGTCTCTCGATCTCATTCTCAGTTACTTGTTCAACAAACGAGAACAAGGCAGGAAGTTCGAGTTGTTTTGATGGCCC |
| 333 | Mal-4-33 | AGCGTCTCTCGATCTCATTCTCATAGACGAACGAACCGAAGGGTCAGAGTCAAGCTTACTCGTGTTGTTTTGATGGCCC |
| 334 | Mal-4-34 | AGCGTCTCTCGATCTCATTCTCATCATCTTCTCGGAAGCAAGAACGAGGATTGACAAACAAGAGTTGTTTTGATGGCCC |
| 335 | Mal-4-35 | AGCGTCTCTCGATCTCATTCTCACTCCTTTTTTATTAAACCGGAGAAAAAATGAGCAATACGAGTTGTTTTGATGGCCC |
| 336 | Mal-4-36 | AGCGTCTCTCGATCTCATTCTCATTTACTTTAACAATATCAAACAAACGCCAAGCCAAGGTGAGTTGTTTTGATGGCCC |
| 337 | Mal-4-37 | AGCGTCTCTCGATCTCATTCTCACATATAGCGGAACTATCCGCCTACACGAAACTTAATAATCGTTGTTTTGATGGCCC |
| 338 | Mal-4-38 | AGCGTCTCTCGATCTCATTCTCACTTCATATCAACAAGAAAACAAATCGAAAACAGCCTGTGTTGTTTTGATGGCCC |
| 339 | Mal-4-39 | AGCGTCTCTCGATCTCATTCTCACTTGTCGTGCGAAGCGCGAAAAGGGAAGCTTAACCTTGATGTTGTTTTGATGGCCC |
| 340 | Mal-4-40 | AGCGTCTCTCGATCTCATTCTCAGACATGAGAACTACACCGAGACCAACCCTGATTCTTGCTTGTTTTGATGGCCC |
| 341 | Mal-4-41 | AGCGTCTCTCGATCTCATTCTCAAGTTCGAAGAAGGCACGACGGAGAAGTTGTTTACCCCTGTGTTGTTTTGATGGCCC |
| 342 | Mal-4-42 | AGCGTCTCTCGATCTCATTCTCACATTATTAACGAGAAAAATAACCCAAGAGTCGACTGACTGGTTGTTTTGATGGCCC |
| 343 | Mal-4-43 | AGCGTCTCTCGATCTCATTCTCACTTGTTATAAAACTCAAGACTAGAAACCGTAAAGGATCGTGTTGTTTTGATGGCCC |
| 344 | Mal-4-44 | AGCGTCTCTCGATCTCATTCTCAGAACGGAATCGACACATTCACGACGAAGAGAATAGAGGCAGTTGTTTTGATGGCCC |
| 345 | Mal-4-45 | AGCGTCTCTCGATCTCATTCTCATAATCATCTTCAAATAACAAAACATGAAAAGTACCGGACGTTGTTTTGATGGCCC |
| 346 | Mal-4-46 | AGCGTCTCTCGATCTCATTCTCATGTTAATTCAAAGAACAAAACCAGCGAGCTTTAAGCGAACGTTGTTTTGATGGCCC |

TABLE 1-continued

List of top sequences from selection experiment.

| SEQ ID NO | Name | Sequence |
|---|---|---|
| 347 | Mal-4-47 | AGCGTCTCTCGATCTCATTCTCATTTACCAGATAATTTCCAGAAAAACGTCGACCGAGGGTAAGTTGTTTTGATGGCCC |
| 348 | Mal-4-48 | AGCGTCTCTCGATCTCATTCTCACCGCGACAATTCGAAGGGAGATCGAATTGAGCCTCTTCTTGTTGTTTTGATGGCCC |
| 349 | Mal-4-49 | AGCGTCTCTCGATCTCATTCTCATTTTATTCCTGAAAGACGACAAAGCAGGCAAACTGACGCTGTTGTTTTGATGGCCC |
| 350 | Mal-4-50 | AGCGTCTCTCGATCTCATTCTCATGGCATGATCTCTGAAGGAACCAAATGCCAACTTTATCACGTTGTTTTGATGGCCC |
| 351 | Mal-4-51 | AGCGTCTCTCGATCTCATTCTCATTGCGAAATCAAGCGATTAACCTGCTATACCTTAACTGAAGTTGTTTTGATGGCCC |
| 352 | Mal-4-52 | AGCGTCTCTCGATCTCATTCTCACTCAATCGATCAAAAGAAACGAGAGTGCGAAAATCGAGCGGTTGTTTTGATGGCCC |
| 353 | Mal-4-53 | AGCGTCTCTCGATCTCATTCTCAGTTATATACAAACACAATTAAACAAGGAATAAAAAGTCGAGTTGTTTTGATGGCCC |
| 354 | Mal-4-54 | AGCGTCTCTCGATCTCATTCTCATAACATTCATTCTACAAAAAACACGAGGTTCGAAAGGATCGTTGTTTTGATGGCCC |
| 355 | Mal-4-55 | AGCGTCTCTCGATCTCATTCTCATTTAATTTCAATCTTGAAGAAACAGCAGCGCAAGCGCTGAGTTGTTTTGATGGCCC |
| 356 | Mal-4-56 | AGCGTCTCTCGATCTCATTCTCACGTTATACCGTTGTGTGAGGAAACCGAAACACAAGGGCTTGTTGTTTTGATGGCCC |
| 357 | Mal-4-57 | AGCGTCTCTCGATCTCATTCTCACTCTTGAACTTACAAGAAAAAAGGAACTACACCGCTGAGAGTTGTTTTGATGGCCC |
| 358 | Mal-4-58 | AGCGTCTCTCGATCTCATTCTCAAATTATGCTCCAGGCCGAGATTAGATAAGATCAAGCTCGGGTTGTTTTGATGGCCC |
| 359 | Mal-4-59 | AGCGTCTCTCGATCTCATTCTCACAAATCTCCTTGCCAACGAAGGAGATGAAACTTCAATCTCGTTGTTTTGATGGCCC |
| 360 | Mal-4-60 | AGCGTCTCTCGATCTCATTCTCATGCTTTCATCTACCAATCATAACAAAGCACAAATAATGGCGTTGTTTTGATGGCCC |
| 361 | Mal-4-61 | AGCGTCTCTCGATCTCATTCTCATTAAAGTTTTACAAGCAAACTACGAAGCGGAGAGCGAAAAGTTGTTTTGATGGCCC |
| 362 | Mal-4-62 | AGCGTCTCTCGATCTCATTCTCATTCCATTCAACATGGAAAAATAATACCTGAGACCGCAGGTGTTGTTTTGATGGCCC |
| 363 | Mal-4-63 | AGCGTCTCTCGATCTCATTCTCAACACGTGGTTAGGAGAAGGAGACTCGATTATTCATTTCCAGTTGTTTTGATGGCCC |
| 364 | Mal-4-64 | AGCGTCTCTCGATCTCATTCTCAATATTATCCTCATCAGAAAACAGAGCGAAGAAATCAAGCGGTTGTTTTGATGGCCC |
| 365 | Mal-4-65 | AGCGTCTCTCGATCTCATTCTCACATTATATCAATACGAAAAAAAGACGAAAAAAGTAGTCGTGTTGTTTTGATGGCCC |
| 366 | Mal-4-66 | AGCGTCTCTCGATCTCATTCTCACTTTAATCTAGTTATCCGAAGCAGAACAGAAATCCGACAGGTTGTTTTGATGGCCC |
| 367 | Mal-4-67 | AGCGTCTCTCGATCTCATTCTCACCTGCAGCAAGATTCAGCAAGCGCAGCGAGATGAAGCGAGGTTGTTTTGATGGCCC |
| 368 | Mal-4-68 | AGCGTCTCTCGATCTCATTCTCAAGGAGCGAGACCTAGACATAGGCGGAGCGACGCACACCTCGTTGTTTTGATGGCCC |
| 369 | Mal-4-69 | AGCGTCTCTCGATCTCATTCTCACCCAGTTGCAAGGGGAAGGAGCGAAGCGACGAACCCTCGAGTTGTTTTGATGGCCC |
| 370 | Mal-4-70 | AGCGTCTCTCGATCTCATTCTCACTTAATAACTGTTTCAAAGCAAGATCGACCGAAAGGGGATGTTGTTTTGATGGCCC |
| 371 | Mal-4-71 | AGCGTCTCTCGATCTCATTCTCAAGGATCGTGCGGACAAACATCCGCCGAGACTCGTATTCTCGTTGTTTTGATGGCCC |
| 372 | Mal-4-72 | AGCGTCTCTCGATCTCATTCTCAAGATTCTATTCAATTCAAACAGAACAAGGAGCTGACGCGAGTTGTTTTGATGGCCC |
| 373 | Mal-4-73 | AGCGTCTCTCGATCTCATTCTCAAGTTCAAACCCTGATAGAAACCCGAAAATTTTAACCGAACGTTGTTTTGATGGCCC |
| 374 | Mal-4-74 | AGCGTCTCTCGATCTCATTCTCAATTCACACAAAAAACAAGACCGGCGAGCACCTGAGTCGAGGTTGTTTTGATGGCCC |
| 375 | Mal-4-75 | AGCGTCTCTCGATCTCATTCTCAATTCTTCATTTATATAAGAAAAACGAACAAAGACGATTCGGTTGTTTTGATGGCCC |
| 376 | Mal-4-76 | AGCGTCTCTCGATCTCATTCTCATGGACGAAGAAGAAAATCGATGAATAAGTATTCCGCAGATGTTGTTTTGATGGCCC |
| 377 | Mal-4-77 | AGCGTCTCTCGATCTCATTCTCAATCTCGTTAACCACAAAAAACAACCAACTTATACCAAGCAGTTGTTTTGATGGCCC |
| 378 | Mal-4-78 | AGCGTCTCTCGATCTCATTCTCACGAAATATCACTCTCTTAGAGAAAAACTGAAAGAAGGCAGTTGTTTTGATGGCCC |
| 379 | Mal-4-79 | AGCGTCTCTCGATCTCATTCTCACTTCCTCGATCAAAACAGAGGAGAGGCACACAAGGATCGTGTTGTTTTGATGGCCC |
| 380 | Mal-4-80 | AGCGTCTCTCGATCTCATTCTCAGTCCGACGTCAAGCGGCAAATGAGACCGTTAATTCACCTCGTTGTTTTGATGGCCC |
| 381 | Mal-4-81 | AGCGTCTCTCGATCTCATTCTCATTCATTAACTCATTAAAAAATACAACGCAACCCGATCGAAGTTGTTTTGATGGCCC |
| 382 | Mal-4-82 | AGCGTCTCTCGATCTCATTCTCAATTTACCTGTTACTAGCAACTGAAACAAAGAACATAAGAAGTTGTTTTGATGGCCC |
| 383 | Mal-4-83 | AGCGTCTCTCGATCTCATTCTCACACTTCAACTTAACTCACAGAAAAATGTAAAACGACCCGAGTTGTTTTGATGGCCC |

TABLE 1-continued

List of top sequences from selection experiment.

| SEQ ID NO | Name | Sequence |
|---|---|---|
| 384 | Mal-4-84 | AGCGTCTCTCGATCTCATTCTCATTAGAAGAACAAGTACGATGGTACCTGAAGGAGCAGTCGAGTTGTTTTGATGGCCC |
| 385 | Mal-4-85 | AGCGTCTCTCGATCTCATTCTCACGACACGTCGTGAAGGAAAGATCGATTTATTCATGTTCCTGTTGTTTTGATGGCCC |
| 386 | Mal-4-86 | AGCGTCTCTCGATCTCATTCTCAAAGATTTTCAACTACTTCGAGCGAAACAAAGACGGGAGGAGTTGTTTTGATGGCCC |
| 387 | Mal-4-87 | AGCGTCTCTCGATCTCATTCTCAGCCCGATGGACCTAAGCAGCGGACTGCCTTGTCTTATTAAGTTGTTTTGATGGCCC |
| 388 | Mal-4-88 | AGCGTCTCTCGATCTCATTCTCATTATATTCACAAAGAAAACAGAAAGCTGCTCGCTAGGCAGGTTGTTTTGATGGCCC |
| 389 | Mal-4-89 | AGCGTCTCTCGATCTCATTCTCACGCGAACGAACGAAGGAAGTGAAGCAGAGATATATCATCTGTTGTTTTGATGGCCC |
| 390 | Mal-4-90 | AGCGTCTCTCGATCTCATTCTCAGACGAGCAACTCCTCTAGGAGTAGCAAGTCTGTAGCTCTCGTTGTTTTGATGGCCC |
| 391 | Mal-4-91 | AGCGTCTCTCGATCTCATTCTCATAATTAACTCAAATCGAAAACGGCCAGGGAGACCTACATGGTTGTTTTGATGGCCC |
| 392 | Mal-4-92 | AGCGTCTCTCGATCTCATTCTCATTTTACTACAAACCAAAACACGCAGGAACCCGCGAGGTTACTTGTTTTGATGGCCC |
| 393 | Mal-4-93 | AGCGTCTCTCGATCTCATTCTCAACTTGACTCTAGTAAAGAAGGTCGAATCTCGGCCAATTTGGTTGTTTTGATGGCCC |
| 394 | Mal-4-94 | AGCGTCTCTCGATCTCATTCTCAAGTTCAAATTTCAATCGCCAAAATAACAAAGCCACCCGTCGTTGTTTTGATGGCCC |
| 395 | Mal-4-95 | AGCGTCTCTCGATCTCATTCTCACATAATCTTGACAAAACAACGAACAGCGGTCGGTAGCATTGTTGTTTTGATGGCCC |
| 396 | Mal-4-96 | AGCGTCTCTCGATCTCATTCTCACGGGAGAAAATCGCAGATCGATACAAGGTTTCTTTTATTCGTTGTTTTGATGGCCC |
| 397 | Mal-4-97 | AGCGTCTCTCGATCTCATTCTCAGCGGCAATTGAATGAAATGAGATTGACTGTTCCGTTTCTGGTTGTTTTGATGGCCC |
| 398 | Mal-4-98 | AGCGTCTCTCGATCTCATTCTCATCAATTTTCACAAAGCAAAACAAGGAGCACAACCGTTACAGTTGTTTTGATGGCCC |
| 399 | Mal-4-99 | AGCGTCTCTCGATCTCATTCTCATTATTATTTACGAAAGAAACAACTTGGGACGAGCCCAACAGTTGTTTTGATGGCCC |
| 400 | Mal-4-100 | AGCGTCTCTCGATCTCATTCTCATTTACACACAAAATAACGAGAAGGCAGTAATGGATAACGAGTTGTTTTGATGGCCC |

TABLE 2

List of conserved motifs.

| SEQ ID NO | Sequence |
|---|---|
| 401 | AGGAGATAA |
| 402 | GATCAANNNAAAAGT |
| 403 | ACCAAANAAAAGGCAA |
| 404 | AACGGAANNGA |
| 405 | GACGAAGAGAATANA |
| 406 | AGCGAAAAATANNNAAAACG |

TABLE 3

Truncated aptamers.

| SEQ ID NO | Name | Sequence |
|---|---|---|
| 407 | Mal-1-1.A | AGCGTCTCTGAAACAGAGGCTTACAGGAGAAAATCGTTTGAT |
| 408 | Mal-1-1.B | TTACAGGAGATAAGAAAGTTGTTGTCTTGAT |
| 409 | Mal-1-1.C | AGCGTCTCTCGAAATCAGAGGCTTA |
| 410 | Mal-1-1.D | CAGGAGATAAGTATTCGATCAATCGAAAAGTTGTTGTTTTG |
| 411 | Mal-1-2.A | TACATTCTCAAAGAGTAGAATGTA |
| 412 | Mal-1-2.B | AGCGTCTCTCGAAACGAGCGATAGA |
| 413 | Mal-1-3.A | GAACATCAGAACCGTAGTTGTTTTGATGGC |
| 414 | Mal-1-4.A | GAGCAATAAAGACAGAAACTGTCTTGATGGCCC |
| 415 | Mal-1-4.B | AACTCTCGATCTCATTCTCAAGGGAGATAGAGAGGAA |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising an aptamer composition comprising at least one oligonucleotide composed of nucleotides selected from the group consisting of: deoxyribonucleotides, ribonucleotides, derivatives of deoxyribonucleotides, derivatives of ribonucleotides, and mixtures thereof;
   wherein the aptamer composition comprises at least one oligonucleotide selected from the group consisting of SEQ ID NO 1, SEQ ID NO 2, SEQ ID NO 102, and SEQ ID NO 201.

2. The personal care composition of claim 1, wherein the personal care composition is an antiperspirant.

3. The personal care composition of claim 1, wherein the personal care composition is a deodorant that is free of aluminum.

4. A personal care composition comprising an aptamer composition comprising at least one oligonucleotide composed of nucleotides selected from the group consisting of: deoxyribonucleotides, ribonucleotides, derivatives of deoxyribonucleotides, derivatives of ribonucleotides, and mixtures thereof; wherein the aptamer composition comprises at least one oligonucleotide selected from the group consisting of oligonucleotides with at least 50% nucleotide sequence identity to sequences selected from the group consisting of SEQ ID NO 1, SEQ ID NO 2, SEQ ID NO 102, and SEQ ID NO 201.

5. The personal care composition of claim 4, wherein the aptamer composition comprises at least one oligonucleotide selected from the group consisting of oligonucleotides with at least 70% nucleotide sequence identity to sequences selected from the group consisting of SEQ ID NO 1, SEQ ID NO 2, SEQ ID NO 102, and SEQ ID NO 201.

6. The personal care composition of claim 5, wherein the aptamer composition comprises at least one oligonucleotide selected from the group consisting of oligonucleotides with at least 90% nucleotide sequence identity to sequences selected from the group consisting of SEQ ID NO 1, SEQ ID NO 2, SEQ ID NO 102, and SEQ ID NO 201.

7. The personal care composition of claim 4, wherein the personal care composition is an antiperspirant.

8. The personal care composition of claim 1, wherein the personal care composition is a deodorant that is free of aluminum.

* * * * *

```
                        SEQUENCE LISTING

<160> NUMBER OF SEQ ID NOS: 418

<210> SEQ ID NO 1
    <211> LENGTH: 79
    <212> TYPE: DNA
    <213> ORGANISM: Artificial Sequence
    <220> FEATURE:
    <223> OTHER INFORMATION: Synthetic DNA sequence

<400> SEQUENCE: 1
agcgtctctc gatctcattc tcagaggctt acaggagata agtattcgat caatcgaaaa      60
gttgttgttt tgatggccc                                                   79

<210> SEQ ID NO 2
    <211> LENGTH: 79
    <212> TYPE: DNA
    <213> ORGANISM: Artificial Sequence
    <220> FEATURE:
    <223> OTHER INFORMATION: Synthetic DNA sequence

<400> SEQUENCE: 2
agcgtctctc gatctcattc tcaaagagta gaatctcaac ggatcgagcg atagaattaa      60
caagttgttt tgatggccc                                                   79

<210> SEQ ID NO 3
    <211> LENGTH: 79
    <212> TYPE: DNA
    <213> ORGANISM: Artificial Sequence
    <220> FEATURE:
    <223> OTHER INFORMATION: Synthetic DNA sequence

<400> SEQUENCE: 3
agcgtctctc gatctcattc tcagtgaatg tagcgagtat gggacgcgaa catcagaacc      60
gtagttgttt tgatggccc                                                   79

<210> SEQ ID NO 4
    <211> LENGTH: 79
    <212> TYPE: DNA
    <213> ORGANISM: Artificial Sequence
    <220> FEATURE:
    <223> OTHER INFORMATION: Synthetic DNA sequence

<400> SEQUENCE: 4
agcgtctctc gatctcattc tcaagggaga tagagaagcg cgagcaataa agacaggcaa      60
agtgttgttt tgatggccc                                                   79

<210> SEQ ID NO 5
    <211> LENGTH: 79
    <212> TYPE: DNA
    <213> ORGANISM: Artificial Sequence
    <220> FEATURE:
    <223> OTHER INFORMATION: Synthetic DNA sequence

<400> SEQUENCE: 5
```

```
agcgtctctc gatctcattc tcacgagaat ggtcgaagat gcggagggaa aactacaagt    60
agtgttgttt tgatggccc                                                 79
```

<210> SEQ ID NO 6
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 6

```
agcgtctctc gatctcattc tcatataatt atgagacgag cagcgagagt agcgagccag    60
aaggttgttt tgatggccc                                                 79
```

<210> SEQ ID NO 7
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 7

```
agcgtctctc gatctcattc tcaaaaatta atgagattcg ggaatgagtt atcgagcacg    60
cgggttgttt tgatggccc                                                 79
```

<210> SEQ ID NO 8
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 8

```
agcgtctctc gatctcattc tcaagggagg aatgaggtct aagaaggcga ggacaaagca    60
agagttgttt tgatggccc                                                 79
```

<210> SEQ ID NO 9
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 9

```
agcgtctctc gatctcattc tcaagggcag agaacgacgt cgagtgatgc gaccgcaaag    60
acagttgttt tgatggccc                                                 79
```

<210> SEQ ID NO 10
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 10

```
agcgtctctc gatctcattc tcacgcgtag tgaagaagaa gatgagtagc cgcgacaaca    60
aaagttgttt tgatggccc                                                 79
```

<210> SEQ ID NO 11
<211> LENGTH: 79
<212> TYPE: DNA
<213> ORGANISM: Artificial Sequence

```
<220> FEATURE:
<223> OTHER INFORMATION: Synthetic DNA sequence

<400> SEQUENCE: 11
agcgtctctc gatctcattc tcagaaagga aatggagcga gagtgaagcg gccggtgaaa      60
ctggttgttt tgatggccc                                                   79

<210> SEQ ID NO 12
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 12
agcgtctctc gatctcattc tcagaatatg tcgaggtaac gcgaggagaa aaaacaacag      60
ttagttgttt tgatggccc                                                   79

<210> SEQ ID NO 13
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 13
agcgtctctc gatctcattc tcaatgtacg tagagaggcg cacggccact cagagaacag      60
tcggttgttt tgatggccc                                                   79

<210> SEQ ID NO 14
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 14
agcgtctctc gatctcattc tcagaactac atctgagagg atccgcaaga gaagcgggac      60
aaggttgttt tgatggccc                                                   79

<210> SEQ ID NO 15
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 15
agcgtctctc gatctcattc tcagcagaga gctaagggtg agtagatcga gtcaagagcg      60
cgggttgttt tgatggccc                                                   79

<210> SEQ ID NO 16
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 16
agcgtctctc gatctcattc tcaaaatggc ctaagtgccg agagatgagg cgaggagaga      60
gccgttgttt tgatggccc                                                   79
```

<210> SEQ ID NO 17
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 17
agcgtctctc gatctcattc tcaacgagaa ggaatcgaaa agcgtgcgaa atcaatcagc    60
gaggttgttt tgatggccc                                                79

<210> SEQ ID NO 18
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 18
agcgtctctc gatctcattc tcaagagatg agggcgaggg aagcggccaa aaaattaagc    60
acggttgttt tgatggccc                                                79

<210> SEQ ID NO 19
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 19
agcgtctctc gatctcattc tcaaagaaag ccgagagagg cgcataatca aaagcaaatc    60
gaagttgttt tgatggccc                                                79

<210> SEQ ID NO 20
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 20
agcgtctctc gatctcattc tcaacggaaa ggtgtgaacg agtaaacgag aagcggcgac    60
caagttgttt tgatggccc                                                79

<210> SEQ ID NO 21
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 21
agcgtctctc gatctcattc tcactagaga agggatcggg tacgcggacg aaacggtaaa    60
caggttgttt tgatggccc                                                79

<210> SEQ ID NO 22
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 22

```
agcgtctctc gatctcattc tcatagtgaa taaggaaaag gacgcggaag cacgaaacac    60
taggttgttt tgatggccc                                                 79

<210> SEQ ID NO 23
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 23
agcgtctctc gatctcattc tcaaaacgaa gaagggaatc agatcgaaag gctccagaaa    60
aaagttgttt tgatggccc                                                 79

<210> SEQ ID NO 24
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 24
agcgtctctc gatctcattc tcaaagagaa tagccgagta agcgagggct caaacgagtt    60
cacgttgttt tgatggccc                                                 79

<210> SEQ ID NO 25
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 25
agcgtctctc gatctcattc tcaaagagga tcgagaaggc ggatcgacaa agaaagaaac    60
ttcgttgttt tgatggccc                                                 79

<210> SEQ ID NO 26
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 26
agcgtctctc gatctcattc tcacagacgt gagaataatc ggtagatgcg gaccacgaac    60
agcgttgttt tgatggccc                                                 79

<210> SEQ ID NO 27
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 27
agcgtctctc gatctcattc tcaggtggcc agtagaatgg atcgggaagc ggtcgaaaaa    60
acagttgttt tgatggccc                                                 79

<210> SEQ ID NO 28
<211> LENGTH: 79
<212> TYPE: DNA
```

<213> ORGANISM: Artificial Sequence
<220> FEATURE:
<223> OTHER INFORMATION: Synthetic DNA sequence

<400> SEQUENCE: 28
agcgtctctc gatctcattc tcatgcgaag aaagatagag cgacgcggta ccaaaaggca    60
acagttgttt tgatggccc                                                 79

<210> SEQ ID NO 29
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 29
agcgtctctc gatctcattc tcaagtgtga aaaggatcga caacgagcag cgcgaccaga    60
caagttgttt tgatggccc                                                 79

<210> SEQ ID NO 30
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 30
agcgtctctc gatctcattc tcaccgggtg gatatgaatg atcggaagtg gggtgattgg    60
tcggttgttt tgatggccc                                                 79

<210> SEQ ID NO 31
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 31
agcgtctctc gatctcattc tcattggtaa gtacgtagaa tgaatcggga tcgcgaccat    60
cgagttgttt tgatggccc                                                 79

<210> SEQ ID NO 32
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 32
agcgtctctc gatctcattc tcaagagagt ggagtagaga gatgcgacgg agaggaaaaa    60
agcgttgttt tgatggccc                                                 79

<210> SEQ ID NO 33
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 33
agcgtctctc gatctcattc tcagttaata tgaaatctaa caagtcgagg acggcaagtt    60
ctagttgttt tgatggccc                                                 79

<210> SEQ ID NO 34
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 34
agcgtctctc gatctcattc tcacttgatg aacaagagaa gagacaagcg cgctgcatca    60
gaagttgttt tgatggccc                                                 79

<210> SEQ ID NO 35
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 35
agcgtctctc gatctcattc tcatgggaag cgaggaagcg ggacaaataa caatcagctg    60
ctggttgttt tgatggccc                                                 79

<210> SEQ ID NO 36
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 36
agcgtctctc gatctcattc tcactgagtg atcaaatgag ttgagatcga ggaaaggcgg    60
agagttgttt tgatggccc                                                 79

<210> SEQ ID NO 37
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 37
agcgtctctc gatctcattc tcagcagatg agatgagctg agcgagtaac gagagtggca    60
agggttgttt tgatggccc                                                 79

<210> SEQ ID NO 38
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 38
agcgtctctc gatctcattc tcagggatc gaggtgcgag ccaaaaagag ttgatgaaag    60
tgagttgttt tgatggccc                                                 79

<210> SEQ ID NO 39
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 39
agcgtctctc gatctcattc tcacccgttg gcaaacggag ataaagggga tcagagagcg    60
cgggttgttt tgatggccc                                                 79

<210> SEQ ID NO 40
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 40
agcgtctctc gatctcattc tcagaaatga gcgagaatcg gaggatgcgc accatcacca    60
acagttgttt tgatggccc                                                 79

<210> SEQ ID NO 41
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 41
agcgtctctc gatctcattc tcatgaattg aggacaagac gcggcgcagt gaagtagacc    60
aatgttgttt tgatggccc                                                 79

<210> SEQ ID NO 42
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 42
agcgtctctc gatctcattc tcaaggagac aatagtgcga ggaaacgcgg caaacaagag    60
gaagttgttt tgatggccc                                                 79

<210> SEQ ID NO 43
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 43
agcgtctctc gatctcattc tcaatgaaga tcgacaagcg gacaccacaa aagctgtgcc    60
gcagttgttt tgatggccc                                                 79

<210> SEQ ID NO 44
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 44
agcgtctctc gatctcattc tcagaaactt gaatgagaca ggagaagtcg cgggtatctg    60
acagttgttt tgatggccc                                                 79

<210> SEQ ID NO 45
<211> LENGTH: 79

```
<212> TYPE: DNA
<213> ORGANISM: Artificial Sequence
<220> FEATURE:
<223> OTHER INFORMATION: Synthetic DNA sequence

<400> SEQUENCE: 45
agcgtctctc gatctcattc tcagcaagga gattacaaga gcgagaaagg atgagacata      60
gaggttgttt tgatggccc                                                  79

<210> SEQ ID NO 46
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 46
agcgtctctc gatctcattc tcataactat gagatataaa cggtgagaga agaggcggac      60
tcagttgttt tgatggccc                                                  79

<210> SEQ ID NO 47
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 47
agcgtctctc gatctcattc tcacaatagt ggagaataaa accgagaaaa ccgcgacagc      60
atagttgttt tgatggccc                                                  79

<210> SEQ ID NO 48
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 48
agcgtctctc gatctcattc tcaaagagag aaggcgagcg aggcaaagag aggaaacttg      60
gtagttgttt tgatggccc                                                  79

<210> SEQ ID NO 49
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 49
agcgtctctc gatctcattc tcaatcagat caagggaagt gagcagatca tcaaacaaac      60
aacgttgttt tgatggccc                                                  79

<210> SEQ ID NO 50
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 50
agcgtctctc gatctcattc tcacgccagt gaggctagag agagtccgcg ggcaagacta      60
```

```
acagttgttt tgatggccc                                              79

<210> SEQ ID NO 51
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 51
agcgtctctc gatctcattc tcacgctagt aagatgactc gaggagcggg ctcaaacgga    60
caagttgttt tgatggccc                                               79

<210> SEQ ID NO 52
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 52
agcgtctctc gatctcattc tcagcgcgtc gatgagcata gagagatcgg gtaagacgag    60
gacgttgttt tgatggccc                                               79

<210> SEQ ID NO 53
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 53
agcgtctctc gatctcattc tcaaacggat cgagaagagg cgcgctgtca gagcaaatcg    60
atagttgttt tgatggccc                                               79

<210> SEQ ID NO 54
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 54
agcgtctctc gatctcattc tcacatataa tacgagagaa agatccgaga agcggcgaaa    60
agagttgttt tgatggccc                                               79

<210> SEQ ID NO 55
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 55
agcgtctctc gatctcattc tcaaagcggg acgcgagcat atgaagatcg aagagcaaaa    60
aacgttgttt tgatggccc                                               79

<210> SEQ ID NO 56
<211> LENGTH: 79
<212> TYPE: DNA
<213> ORGANISM: Artificial Sequence
<220> FEATURE:
<223> OTHER INFORMATION: Synthetic DNA sequence
```

<400> SEQUENCE: 56
agcgtctctc gatctcattc tcagatgtga tcgtgacgaa tgatcgaaaa cgcgggcgag    60
taggttgttt tgatggccc                                                 79

<210> SEQ ID NO 57
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 57
agcgtctctc gatctcattc tcaaataagg tgtaagagaa ggacagagag cggcataaga    60
gaggttgttt tgatggccc                                                 79

<210> SEQ ID NO 58
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 58
agcgtctctc gatctcattc tcaagaatga ggtcggtgga agcgaaccaa ggaaaaagct    60
cgagttgttt tgatggccc                                                 79

<210> SEQ ID NO 59
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 59
agcgtctctc gatctcattc tcaagctgag gattgagaac tgaatccgag cgcggatatc    60
aaagttgttt tgatggccc                                                 79

<210> SEQ ID NO 60
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 60
agcgtctctc gatctcattc tcaatgagac ggtacgcgga caaaagcaag gaaccgtagg    60
aaagttgttt tgatggccc                                                 79

<210> SEQ ID NO 61
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 61
agcgtctctc gatctcattc tcacataggt gcagcctatg gtggaagaga gagacgtggc    60
aatgttgttt tgatggccc                                                 79

<210> SEQ ID NO 62

<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 62
agcgtctctc gatctcattc tcagaagaaa aaatcgagag gagcggagag aaacgatacg    60
caggttgttt tgatggccc                                                79

<210> SEQ ID NO 63
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 63
agcgtctctc gatctcattc tcatgttatc gaagatgcga cagaccagca gttagaaaca    60
aaagttgttt tgatggccc                                                79

<210> SEQ ID NO 64
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 64
agcgtctctc gatctcattc tcaaatagaa aaggagattt cggaagcgcg gagacaccat    60
gaagttgttt tgatggccc                                                79

<210> SEQ ID NO 65
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 65
agcgtctctc gatctcattc tcaataaagg agaaagatgg atcgcgtgcg cgactcacca    60
aaagttgttt tgatggccc                                                79

<210> SEQ ID NO 66
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 66
agcgtctctc gatctcattc tcacatgata atcgagggat gcgcccatat caaactgaca    60
ggagttgttt tgatggccc                                                79

<210> SEQ ID NO 67
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 67
agcgtctctc gatctcattc tcagtatgag cgggatcgta aacgcgagct gcaaataatg    60
gtagttgttt tgatggccc                                                  79

<210> SEQ ID NO 68
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 68
agcgtctctc gatctcattc tcatagactt aagatcgtg attctcggag ggcagattag    60
taagttgttt tgatggccc                                                  79

<210> SEQ ID NO 69
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 69
agcgtctctc gatctcattc tcaaagagaa ccgtacagag tcgagcagag ctgacaaaat    60
agagttgttt tgatggccc                                                  79

<210> SEQ ID NO 70
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 70
agcgtctctc gatctcattc tcaaagcgta aaacgcacgt aaaatgagtc aagagagcgg    60
cgagttgttt tgatggccc                                                  79

<210> SEQ ID NO 71
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 71
agcgtctctc gatctcattc tcaaatgacc taagcgatgg gacgcgagca caaaaggaca    60
acggttgttt tgatggccc                                                  79

<210> SEQ ID NO 72
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 72
agcgtctctc gatctcattc tcaaggtaca tataccggag atagaatcga gcacgagccg    60
gaagttgttt tgatggccc                                                  79

<210> SEQ ID NO 73
<211> LENGTH: 79
<212> TYPE: DNA
<213> ORGANISM: Artificial Sequence
<220> FEATURE:

<223> OTHER INFORMATION: Synthetic DNA sequence

<400> SEQUENCE: 73
agcgtctctc gatctcattc tcacggtgag aatagcgaag acaaggcagc ggataaaaaa    60
gcagttgttt tgatggccc                                                 79

<210> SEQ ID NO 74
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 74
agcgtctctc gatctcattc tcagatgaag actagagagc gacagaaata accaacgcaa    60
atcgttgttt tgatggccc                                                 79

<210> SEQ ID NO 75
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 75
agcgtctctc gatctcattc tcagcaataa ggcaggatgc tgtatgagca agcgagagta    60
catgttgttt tgatggccc                                                 79

<210> SEQ ID NO 76
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 76
agcgtctctc gatctcattc tcagtcgatt tttgtgtgca tgcggacact tgggagcgat    60
ccggttgttt tgatggccc                                                 79

<210> SEQ ID NO 77
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 77
agcgtctctc gatctcattc tcagtacact gagaagattg atcgggagat ttagcgacca    60
gcagttgttt tgatggccc                                                 79

<210> SEQ ID NO 78
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 78
agcgtctctc gatctcattc tcataggaga agctggacga gaaagcgagc caccaatgga    60
catgttgttt tgatggccc                                                 79

-continued

```
<210> SEQ ID NO 79
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 79
agcgtctctc gatctcattc tcatgaacga gaagtctgag agatgcggag agatcgaaac    60
gaagttgttt tgatggccc                                                79

<210> SEQ ID NO 80
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 80
agcgtctctc gatctcattc tcaatgaaaa caagcagcga ggagaggcac tttcaaacgc    60
gaagttgttt tgatggccc                                                79

<210> SEQ ID NO 81
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 81
agcgtctctc gatctcattc tcactaagtg gctggatcga gaagaacacg accgtcagaa    60
aacgttgttt tgatggccc                                                79

<210> SEQ ID NO 82
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 82
agcgtctctc gatctcattc tcaggagacc gaagagcaga ccgcaaaacg attacgaagg    60
cgcgttgttt tgatggccc                                                79

<210> SEQ ID NO 83
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 83
agcgtctctc gatctcattc tcagtgaaaa gagagaccgg aggatagacc aaagaaagag    60
catgttgttt tgatggccc                                                79

<210> SEQ ID NO 84
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 84
```

```
agcgtctctc gatctcattc tcagtttgtt ctcaacggaa agtgaaacag gggagcccca    60
cgagttgttt tgatggccc                                                 79
```

<210> SEQ ID NO 85
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 85

```
agcgtctctc gatctcattc tcaagagaat aagagtcaga acacggcacc gaaagagaaa    60
agcgttgttt tgatggccc                                                 79
```

<210> SEQ ID NO 86
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 86

```
agcgtctctc gatctcattc tcaagtaaaa ccgagaatga aatggatgat gcgagataga    60
aaagttgttt tgatggccc                                                 79
```

<210> SEQ ID NO 87
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 87

```
agcgtctctc gatctcattc tcaatggaga tctagtagcg cggaacgata aaacggatca    60
cgagttgttt tgatggccc                                                 79
```

<210> SEQ ID NO 88
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 88

```
agcgtctctc gatctcattc tcacgggcac aaaggtgcct gggaaacgcg agatcggaaa    60
cacgttgttt tgatggccc                                                 79
```

<210> SEQ ID NO 89
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 89

```
agcgtctctc gatctcattc tcagttgtta acaacataa gaatgctcgg gttgccatgt     60
cgggttgttt tgatggccc                                                 79
```

<210> SEQ ID NO 90
<211> LENGTH: 79
<212> TYPE: DNA
<213> ORGANISM: Artificial Sequence

```
<220> FEATURE:
<223> OTHER INFORMATION: Synthetic DNA sequence

<400> SEQUENCE: 90
agcgtctctc gatctcattc tcaagatcga ataaagcga gcatcgaacg agtacagcaa      60
gaagttgttt tgatggccc                                                  79

<210> SEQ ID NO 91
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 91
agcgtctctc gatctcattc tcactgagaa agagagcgtt gcgcgagcaa aaagcagaca     60
taggttgttt tgatggccc                                                  79

<210> SEQ ID NO 92
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 92
agcgtctctc gatctcattc tcagatgctg ggaatgagtg aaaggggatg cgagttgcaa     60
aaagttgttt tgatggccc                                                  79

<210> SEQ ID NO 93
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 93
agcgtctctc gatctcattc tcattggaga cccaagagcg agaacgcgag tttggaaaac     60
aaagttgttt tgatggccc                                                  79

<210> SEQ ID NO 94
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 94
agcgtctctc gatctcattc tcaaagcata gaaagcgaaa gatcggaagg tagtgggcga     60
agggttgttt tgatggccc                                                  79

<210> SEQ ID NO 95
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 95
agcgtctctc gatctcattc tcaagaacga ggtaacgagc gcggccgaag caatgaagga     60
cgagttgttt tgatggccc                                                  79
```

<210> SEQ ID NO 96
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 96
agcgtctctc gatctcattc tcactgagga aacagagcga gtcaacgcgg aaatcagaaa    60
tgcgttgttt tgatggccc                                                79

<210> SEQ ID NO 97
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 97
agcgtctctc gatctcattc tcacttcaat acagtagagg gaaagatcgt gggtgccgat    60
gttgttgttt tgatggccc                                                79

<210> SEQ ID NO 98
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 98
agcgtctctc gatctcattc tcagacgtga ggatcgacgt aaacgcgcct ctagcaaaac    60
gcagttgttt tgatggccc                                                79

<210> SEQ ID NO 99
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 99
agcgtctctc gatctcattc tcagtgggat cgagcagagc ggcggatata gacaaaaacc    60
gtagttgttt tgatggccc                                                79

<210> SEQ ID NO 100
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 100
agcgtctctc gatctcattc tcagtgtgct aatgagaata aaacgcgaga ggatgagaaa    60
caagttgttt tgatggccc                                                79

<210> SEQ ID NO 101
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 101
agcgtctctc gatctcattc tcacttgatc ttcattcacc aaacaaaagg caactgatca    60
gccgttgttt tgatggccc                                                 79

<210> SEQ ID NO 102
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 102
agcgtctctc gatctcattc tcatctcgta aacaaaagaa acaaaatgga cgacgaccga    60
caggttgttt tgatggccc                                                 79

<210> SEQ ID NO 103
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 103
agcgtctctc gatctcattc tcaattcact tgctccaaaa agcaaaagca atcggtcgac    60
cgagttgttt tgatggccc                                                 79

<210> SEQ ID NO 104
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 104
agcgtctctc gatctcattc tcacttttc aactgtatta cacaaaatca aaaagcagcc    60
gctgttgttt tgatggccc                                                 79

<210> SEQ ID NO 105
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 105
agcgtctctc gatctcattc tcataattta catacactga aaaaagcgaa acaagacgta    60
gaggttgttt tgatggccc                                                 79

<210> SEQ ID NO 106
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 106
agcgtctctc gatctcattc tcagacgagc aactcctcta ggagtagcaa gtctgtagct    60
ctcgttgttt tgatggccc                                                 79

<210> SEQ ID NO 107
<211> LENGTH: 79
<212> TYPE: DNA

<213> ORGANISM: Artificial Sequence
<220> FEATURE:
<223> OTHER INFORMATION: Synthetic DNA sequence

<400> SEQUENCE: 107

```
agcgtctctc gatctcattc tcaatattgt tttactcgtc caagtcgcat ccgaagaaag    60
cgagttgttt tgatggccc                                                 79
```

<210> SEQ ID NO 108
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 108

```
agcgtctctc gatctcattc tcaactttat cacatcggaa acaaggatca agaaccatag    60
agagttgttt tgatggccc                                                 79
```

<210> SEQ ID NO 109
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 109

```
agcgtctctc gatctcattc tcacgttata ccgttgtgtg aggaaaccga aacacaaggg    60
cttgttgttt tgatggccc                                                 79
```

<210> SEQ ID NO 110
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 110

```
agcgtctctc gatctcattc tcattaattc acttagagac gaaagaaaaa ggactgacca    60
ggagttgttt tgatggccc                                                 79
```

<210> SEQ ID NO 111
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 111

```
agcgtctctc gatctcattc tcatttgttt aggcgagcaa actacaaagg tttgaacgca    60
ctcgttgttt tgatggccc                                                 79
```

<210> SEQ ID NO 112
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 112

```
agcgtctctc gatctcattc tcatttacta cactaatccg ggaaaaagaa cggaaccgaa    60
gccgttgttt tgatggccc                                                 79
```

<210> SEQ ID NO 113
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 113
agcgtctctc gatctcattc tcacgtcatg ctacttgatt aagatcaaaa cacagccacg    60
cacgttgttt tgatggccc                                                 79

<210> SEQ ID NO 114
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 114
agcgtctctc gatctcattc tcagttatat acaaacacaa ttaaacaagg aataaaagt    60 cgagttgttt tgatggccc                                                 79

<210> SEQ ID NO 115
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 115
agcgtctctc gatctcattc tcattatcac gtctctgcaa acaagaaaaa accaagggat    60
cgggttgttt tgatggccc                                                 79

<210> SEQ ID NO 116
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 116
agcgtctctc gatctcattc tcactataca aactcgatcg gaataaaagt gttcaaacac    60
acagttgttt tgatggccc                                                 79

<210> SEQ ID NO 117
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 117
agcgtctctc gatctcattc tcaattcttc atccccgcaa aaacaaagaa cgacaagcga    60
aaagttgttt tgatggccc                                                 79

<210> SEQ ID NO 118
<211> LENGTH: 79
<212> TYPE: DNA
<213> ORGANISM: Artificial Sequence
<220> FEATURE:
<223> OTHER INFORMATION: Synthetic DNA sequence

```
<400> SEQUENCE: 118
agcgtctctc gatctcattc tcaaagggct ccgcaaggag cagaagagac tcgatttata    60
taagttgttt tgatggccc                                                 79

<210> SEQ ID NO 119
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 119
agcgtctctc gatctcattc tcatttactc ggaaaaaaca gccagcgaac cagcaagagc    60
ttagttgttt tgatggccc                                                 79

<210> SEQ ID NO 120
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 120
agcgtctctc gatctcattc tcatcttacc caaatgaaaa caaatcggag gatacagcgt    60
agagttgttt tgatggccc                                                 79

<210> SEQ ID NO 121
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 121
agcgtctctc gatctcattc tcaccggtcg aaggttctgg caagaaccga agaacgaaat    60
ctcgttgttt tgatggccc                                                 79

<210> SEQ ID NO 122
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 122
agcgtctctc gatctcattc tcacggaaga acaacatgac gaagtgggaa aggtatgagg    60
agtgttgttt tgatggccc                                                 79

<210> SEQ ID NO 123
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 123
agcgtctctc gatctcattc tcattccttg ttacactgct agaccaatca tgcaaaacga    60
gacgttgttt tgatggccc                                                 79

<210> SEQ ID NO 124
<211> LENGTH: 79
```

<212> TYPE: DNA
<213> ORGANISM: Artificial Sequence
<220> FEATURE:
<223> OTHER INFORMATION: Synthetic DNA sequence

<400> SEQUENCE: 124
agcgtctctc gatctcattc tcattatttc aacgcaacaa caaccgtcgt gatacaagat    60
aaggttgttt tgatggccc    79

<210> SEQ ID NO 125
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 125
agcgtctctc gatctcattc tcattcatat gcaatctcgc aacaaacgac gaacaaaaac    60
ggagttgttt tgatggccc    79

<210> SEQ ID NO 126
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 126
agcgtctctc gatctcattc tcaatattat cctcatcaga aaacagagcg aagaaatcaa    60
gcggttgttt tgatggccc    79

<210> SEQ ID NO 127
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 127
agcgtctctc gatctcattc tcacctgcag caagattcag caagcgcagc gagatgaagc    60
gaggttgttt tgatggccc    79

<210> SEQ ID NO 128
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 128
agcgtctctc gatctcattc tcattgctct aatgcgagtt gaaaactcac aggtcttgga    60
cgagttgttt tgatggccc    79

<210> SEQ ID NO 129
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 129
agcgtctctc gatctcattc tcattattat ccttcgatca aaaaattaac aaaccacaca    60
aaagttgttt tgatggccc                                            79

<210> SEQ ID NO 130
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 130
agcgtctctc gatctcattc tcacttaaat ttacaaaaaa cgaaccagcg atcgaagata    60
gaggttgttt tgatggccc                                            79

<210> SEQ ID NO 131
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 131
agcgtctctc gatctcattc tcattcctta catatggctt caagcctcaa agcatctaaa    60
cgagttgttt tgatggccc                                            79

<210> SEQ ID NO 132
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 132
agcgtctctc gatctcattc tcattcaatc acttccatcc ccagaaaaga aacaacgaag    60
ctggttgttt tgatggccc                                            79

<210> SEQ ID NO 133
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 133
agcgtctctc gatctcattc tcaattacac aaggaataac cgagaacaga cgaccggtgc    60
gaggttgttt tgatggccc                                            79

<210> SEQ ID NO 134
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 134
agcgtctctc gatctcattc tcacttaaac taccaaacat aattttcaag ctcctaatcc    60
caagttgttt tgatggccc                                            79

<210> SEQ ID NO 135
<211> LENGTH: 79
<212> TYPE: DNA
<213> ORGANISM: Artificial Sequence
<220> FEATURE:
<223> OTHER INFORMATION: Synthetic DNA sequence

```
<400> SEQUENCE: 135
agcgtctctc gatctcattc tcaaattaca tttcattcca gcgaaaaata cagaaaacgt    60
cgagttgttt tgatggccc                                                 79

<210> SEQ ID NO 136
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 136
agcgtctctc gatctcattc tcatctatcc tctcaagaaa atacacgaaa acaaacacga    60
agagttgttt tgatggccc                                                 79

<210> SEQ ID NO 137
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 137
agcgtctctc gatctcattc tcaagccttg cggacaaaga gtgagcgagg attgagttta    60
cccgttgttt tgatggccc                                                 79

<210> SEQ ID NO 138
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 138
agcgtctctc gatctcattc tcagttactt gttcaacaaa cgagaacaag gcaggaagtt    60
cgagttgttt tgatggccc                                                 79

<210> SEQ ID NO 139
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 139
agcgtctctc gatctcattc tcaattaagt aatctacaac gcaaaacaag ccgcaacgga    60
gcagttgttt tgatggccc                                                 79

<210> SEQ ID NO 140
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 140
agcgtctctc gatctcattc tcatatttca tcacaattca aaacaagact gcacggaaag    60
catgttgttt tgatggccc                                                 79

<210> SEQ ID NO 141
```

```
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 141
agcgtctctc gatctcattc tcattgaaaa gaacggatcc tacgcgaacc atggagagat      60
cctgttgttt tgatggccc                                                  79

<210> SEQ ID NO 142
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 142
agcgtctctc gatctcattc tcatattaca tttccaatcg taacattgaa acaaatcccg      60
aaagttgttt tgatggccc                                                  79

<210> SEQ ID NO 143
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 143
agcgtctctc gatctcattc tcactaccac tgcaacgcta gactttgcag tgtgaactcg      60
cttgttgttt tgatggccc                                                  79

<210> SEQ ID NO 144
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 144
agcgtctctc gatctcattc tcaaaacttc aattcaatgc ttcaaaacag ctatagagaa      60
ccggttgttt tgatggccc                                                  79

<210> SEQ ID NO 145
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 145
agcgtctctc gatctcattc tcattaatca agcaaaaaag aaaggacgca tatgctagcg      60
acggttgttt tgatggccc                                                  79

<210> SEQ ID NO 146
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 146
agcgtctctc gatctcattc tcaaacgatt ccgaggaggc gaggaagaag ttgcctactt      60
```
attgttgttt tgatggccc                                          79

<210> SEQ ID NO 147
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 147
agcgtctctc gatctcattc tcaactaaaa ttctcaaact tcatgcagca gaacaagacc    60
tacgttgttt tgatggccc                                          79

<210> SEQ ID NO 148
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 148
agcgtctctc gatctcattc tcacttatta aaactgcaaa aagaccgagt tcagtcgtcg    60
aaggttgttt tgatggccc                                          79

<210> SEQ ID NO 149
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 149
agcgtctctc gatctcattc tcatttaatt tcaatcttga agaaacagca gcgcaagcgc    60
tgagttgttt tgatggccc                                          79

<210> SEQ ID NO 150
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 150
agcgtctctc gatctcattc tcaattgtct ttattacaga gaacaacgag agcaagtgcc    60
tcagttgttt tgatggccc                                          79

<210> SEQ ID NO 151
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 151
agcgtctctc gatctcattc tcatttgaca cccgaccaac tcagcagggt agacgaaatt    60
aaagttgttt tgatggccc                                          79

<210> SEQ ID NO 152
<211> LENGTH: 79
<212> TYPE: DNA
<213> ORGANISM: Artificial Sequence
<220> FEATURE:

<223> OTHER INFORMATION: Synthetic DNA sequence

<400> SEQUENCE: 152
agcgtctctc gatctcattc tcaatctttt ccgtcaagca ccagacaagc gaaagaaggt     60
ctagttgttt tgatggccc                                                  79

<210> SEQ ID NO 153
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 153
agcgtctctc gatctcattc tcatatttaa ctcacatcct gagaaacaac taacgacaca     60
taagttgttt tgatggccc                                                  79

<210> SEQ ID NO 154
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 154
agcgtctctc gatctcattc tcatctgtga taataatcaa attataagct gatcgaagac     60
cgggttgttt tgatggccc                                                  79

<210> SEQ ID NO 155
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 155
agcgtctctc gatctcattc tcacttaata actgtttcaa agcaagatcg accgaaaggg     60
gatgttgttt tgatggccc                                                  79

<210> SEQ ID NO 156
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 156
agcgtctctc gatctcattc tcaccagtac aaaaataaga cacaaacccc aggcctcgct     60
tgagttgttt tgatggccc                                                  79

<210> SEQ ID NO 157
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 157
agcgtctctc gatctcattc tcaagtccga acaaccggaa agagccaacc ggcaacgctc     60
ttcgttgttt tgatggccc                                                  79

```
<210> SEQ ID NO 158
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 158
agcgtctctc gatctcattc tcaccttttg caaacacatc tctaattaaa cgaaaccagg    60
ctcgttgttt tgatggccc                                                 79

<210> SEQ ID NO 159
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 159
agcgtctctc gatctcattc tcaagagccc gattgcagaa ttcggctcgg tttaattaag    60
tcggttgttt tgatggccc                                                 79

<210> SEQ ID NO 160
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 160
agcgtctctc gatctcattc tcaacgaaag agacgagaat agattacacc agccctcttg    60
tttgttgttt tgatggccc                                                 79

<210> SEQ ID NO 161
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 161
agcgtctctc gatctcattc tcattatact tgaacaaaac cgaaattacg atcacggcag    60
atcgttgttt tgatggccc                                                 79

<210> SEQ ID NO 162
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 162
agcgtctctc gatctcattc tcatacttgt ccttaattaa aaagcagaaa gaaataacga    60
gtagttgttt tgatggccc                                                 79

<210> SEQ ID NO 163
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 163
```
agcgtctctc gatctcattc tcatgcccgg agaaaccgaa ggcgacttaa atataaactc    60
cttgttgttt tgatggccc                                                79

<210> SEQ ID NO 164
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 164
agcgtctctc gatctcattc tcaggtcacg cgctgttgca agcaatgagc gcgactgact    60
ctagttgttt tgatggccc                                                79

<210> SEQ ID NO 165
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 165
agcgtctctc gatctcattc tcagagataa tctctgtgaa gaaagaaacg gatttacttg    60
cttgttgttt tgatggccc                                                79

<210> SEQ ID NO 166
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 166
agcgtctctc gatctcattc tcactatcac tggaagacaa atatagagtc tacaaacgat    60
gaagttgttt tgatggccc                                                79

<210> SEQ ID NO 167
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 167
agcgtctctc gatctcattc tcaactctca acatctggag tcaagaactt gatgagcaat    60
gatgttgttt tgatggccc                                                79

<210> SEQ ID NO 168
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 168
agcgtctctc gatctcattc tcacaaagaa cagaaagagg aagaaatgac gaggctggag    60
tttgttgttt tgatggccc                                                79

<210> SEQ ID NO 169
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 169
agcgtctctc gatctcattc tcattattta cttcactcga aacaacatac gggaatcccg    60
gcagttgttt tgatggccc                                                 79

<210> SEQ ID NO 170
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 170
agcgtctctc gatctcattc tcattttcac atccatcaaa ggatgaagaa ttcatatcga    60
tcggttgttt tgatggccc                                                 79

<210> SEQ ID NO 171
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 171
agcgtctctc gatctcattc tcaagctacg aacgtagcga aaagtagagc tcttgttata    60
cctgttgttt tgatggccc                                                 79

<210> SEQ ID NO 172
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 172
agcgtctctc gatctcattc tcaatcttac gttcaacgac caaaacaaag gaaagacgtg    60
ctcgttgttt tgatggccc                                                 79

<210> SEQ ID NO 173
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 173
agcgtctctc gatctcattc tcaatcttat atctaacaaa tgagtaacac ttaacacacc    60
tcagttgttt tgatggccc                                                 79

<210> SEQ ID NO 174
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 174
agcgtctctc gatctcattc tcaaagcctt ctacattcag cacaaaccac aaagaccacc    60
catgttgttt tgatggccc                                                 79

<210> SEQ ID NO 175
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 175
agcgtctctc gatctcattc tcaacatagt ttacattcct tataacaaca tctcaaaaca      60
atggttgttt tgatggccc                                                  79

<210> SEQ ID NO 176
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 176
agcgtctctc gatctcattc tcatatactt catatagcaa aaagtctgaa ccgacaggga      60
caggttgttt tgatggccc                                                  79

<210> SEQ ID NO 177
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 177
agcgtctctc gatctcattc tcaggctaga gcgaatgatg attcgactcc aaccggtgca      60
ctagttgttt tgatggccc                                                  79

<210> SEQ ID NO 178
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 178
agcgtctctc gatctcattc tcatactaca tgcgtattcg aaacgataat acgcaataac      60
tcggttgttt tgatggccc                                                  79

<210> SEQ ID NO 179
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 179
agcgtctctc gatctcattc tcacagtcga ctgaatggac ttgttaaaac ggagcaaggt      60
atagttgttt tgatggccc                                                  79

<210> SEQ ID NO 180
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 180
agcgtctctc gatctcattc tcacgcaaca acacagttca tagccgagga ccgtcctctt    60
gcggttgttt tgatggccc                                                 79

<210> SEQ ID NO 181
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 181
agcgtctctc gatctcattc tcatcattta tccgaaaaga aaaacaagc ggcttgagca     60 cgagttgttt tgatggccc                                                 79

<210> SEQ ID NO 182
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 182
agcgtctctc gatctcattc tcatttaatt cactgcagaa caacaacgga aactagacgc    60
caagttgttt tgatggccc                                                 79

<210> SEQ ID NO 183
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 183
agcgtctctc gatctcattc tcaaacgaat ggtccatcgg tgttacttaa gaatatgcat    60
gacgttgttt tgatggccc                                                 79

<210> SEQ ID NO 184
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 184
agcgtctctc gatctcattc tcaatttacc tgttactagc aactgaaaca aagaacataa    60
gaagttgttt tgatggccc                                                 79

<210> SEQ ID NO 185
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 185
agcgtctctc gatctcattc tcacgttaac ctttacgaat agataacaga actaaatcta    60
gaagttgttt tgatggccc                                                 79

<210> SEQ ID NO 186
<211> LENGTH: 79
<212> TYPE: DNA

<213> ORGANISM: Artificial Sequence
<220> FEATURE:
<223> OTHER INFORMATION: Synthetic DNA sequence

<400> SEQUENCE: 186
agcgtctctc gatctcattc tcacttgctt ggttagttcc gcaaaaagat ggacgaagga    60
caggttgttt tgatggccc                                                 79

<210> SEQ ID NO 187
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 187
agcgtctctc gatctcattc tcacacattt tacacgcata catcacggat cgaaatacca    60
ccggttgttt tgatggccc                                                 79

<210> SEQ ID NO 188
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 188
agcgtctctc gatctcattc tcacattaat ctcgctttaa tacaaaactg caatcgataa    60
tcggttgttt tgatggccc                                                 79

<210> SEQ ID NO 189
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 189
agcgtctctc gatctcattc tcatttagct cttcacttga aaaatccata caaagaaata    60
agagttgttt tgatggccc                                                 79

<210> SEQ ID NO 190
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 190
agcgtctctc gatctcattc tcaacgctag tacatacccg atggaagtac tagtgctgat    60
cttgttgttt tgatggccc                                                 79

<210> SEQ ID NO 191
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 191
agcgtctctc gatctcattc tcaattacgt acctagacca caacatagca tcggtagcag    60
ctagttgttt tgatggccc                                                 79

<210> SEQ ID NO 192
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 192
agcgtctctc gatctcattc tcacttgttc atgcacaaag caaacaaccc gagactcgta    60
gcagttgttt tgatggccc                                                 79

<210> SEQ ID NO 193
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 193
agcgtctctc gatctcattc tcataatcat cttcaaataa caaaacatga aaaagtaccg    60
gacgttgttt tgatggccc                                                 79

<210> SEQ ID NO 194
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 194
agcgtctctc gatctcattc tcatttctac tattcaaaaa cccgaaagaa aaactgaaag    60
cccgttgttt tgatggccc                                                 79

<210> SEQ ID NO 195
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 195
agcgtctctc gatctcattc tcacttaaat ttacaaaaaa cgaaccagtg atcgaagata    60
gaggttgttt tgatggccc                                                 79

<210> SEQ ID NO 196
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 196
agcgtctctc gatctcattc tcagaatcca caagcatcaa cggcgatagc taataaaatg    60
cacgttgttt tgatggccc                                                 79

<210> SEQ ID NO 197
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 197
agcgtctctc gatctcattc tcaaaacgtt ttatagatat caaggaacca tagtatcaga    60
caagttgttt tgatggccc                                                 79

<210> SEQ ID NO 198
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 198
agcgtctctc gatctcattc tcaaaaggtg aggacagaac ctatgatagc acggtttaat    60
catgttgttt tgatggccc                                                 79

<210> SEQ ID NO 199
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 199
agcgtctctc gatctcattc tcacggacta atctaagagc ttaagtacgc gtagattagc    60
acggttgttt tgatggccc                                                 79

<210> SEQ ID NO 200
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 200
agcgtctctc gatctcattc tcattcctgc tttacgcacc aaacaatcac gagcaccaag    60
agtgttgttt tgatggccc                                                 79

<210> SEQ ID NO 201
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 201
agcgtctctc gatctcattc tcagaacgga atcgacacat tcacgacgaa gagaatagag    60
gcagttgttt tgatggccc                                                 79

<210> SEQ ID NO 202
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 202
agcgtctctc gatctcattc tcacgaagag tggttgatgg aatcgaggag cgcgagccca    60
gatgttgttt tgatggccc                                                 79

<210> SEQ ID NO 203
<211> LENGTH: 79

```
<212> TYPE: DNA
<213> ORGANISM: Artificial Sequence
<220> FEATURE:
<223> OTHER INFORMATION: Synthetic DNA sequence

<400> SEQUENCE: 203
agcgtctctc gatctcattc tcacacggtg ttccaagagt gagtaagaga acgaaaggga    60
aatgttgttt tgatggccc                                                 79

<210> SEQ ID NO 204
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 204
agcgtctctc gatctcattc tcaatggaga tctagtagcg cggaacgaca aaacggatca    60
cgagttgttt tgatggccc                                                 79

<210> SEQ ID NO 205
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 205
agcgtctctc gatctcattc tcaaattaca tttcattcca gcgaaaaata cagaaaacgt    60
cgagttgttt tgatggccc                                                 79

<210> SEQ ID NO 206
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 206
agcgtctctc gatctcattc tcactcacct taaactttaa cgaattaaaa aacaagaccg    60
gcagttgttt tgatggccc                                                 79

<210> SEQ ID NO 207
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 207
agcgtctctc gatctcattc tcagggtgga aatgaaatcg gagatgcggc tgatgtcaga    60
acggttgttt tgatggccc                                                 79

<210> SEQ ID NO 208
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 208
agcgtctctc gatctcattc tcaggacgga atcgacacat tcacgacgaa gagaatagag    60
```
gcagttgttt tgatggccc                                            79

<210> SEQ ID NO 209
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 209
agcgtctctc gatctcattc tcatccgacc ggcgtgaaag ggatccagaa cgcgacccaa    60
aaagttgttt tgatggccc                                            79

<210> SEQ ID NO 210
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 210
agcgtctctc gatctcattc tcaatgtggt cgagtgcacg cggaccaaag taagatcgga    60
cgagttgttt tgatggccc                                            79

<210> SEQ ID NO 211
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 211
agcgtctctc gatctcattc tcattcatta aattcaaaca aaagaaacgg tgcgacagac    60
caggttgttt tgatggccc                                            79

<210> SEQ ID NO 212
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 212
agcgtctctc gatctcattc tcagaacatt ccgaagcgaa tgtacggaaa aacggagatc    60
gctgttgttt tgatggccc                                            79

<210> SEQ ID NO 213
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 213
agcgtctctc gatctcattc tcacctaagg gaaacatgag tcggagaagc ggacaaacca    60
taagttgttt tgatggccc                                            79

<210> SEQ ID NO 214
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 214
agcgtctctc gatctcattc tcaaaaatga tgatcggcag aagcgccaag taagaagcga    60
taggttgttt tgatggccc                                                 79

<210> SEQ ID NO 215
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 215
agcgtctctc gatctcattc tcatgaggtg aagaaacgcg ccagtcaaag cgctacccga    60
ggagttgttt tgatggccc                                                 79

<210> SEQ ID NO 216
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 216
agcgtctctc gatctcattc tcacacccgt tgagaaaaag attgaaagag gcgacgcacc    60
caagttgttt tgatggccc                                                 79

<210> SEQ ID NO 217
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 217
agcgtctctc gatctcattc tcatagacga acgaaccgaa gggtcagagt caagcttact    60
cgtgttgttt tgatggccc                                                 79

<210> SEQ ID NO 218
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 218
agcgtctctc gatctcattc tcagcgggtc ttaagaaaat gagagagaag cgcgagccag    60
acagttgttt tgatggccc                                                 79

<210> SEQ ID NO 219
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 219
agcgtctctc gatctcattc tcacacccgc atggtgtatg gatgatgatc aggagatgcg    60
accgttgttt tgatggccc                                                 79

<210> SEQ ID NO 220

```
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 220
agcgtctctc gatctcattc tcagcagcgg agaacgatgt gcaggagatg cgcgccaagc    60
aaagttgttt tgatggccc                                                 79

<210> SEQ ID NO 221
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 221
agcgtctctc gatctcattc tcattatact tgaacaaaac cgaaattacg atcacggcag    60
atcgttgttt tgatggccc                                                 79

<210> SEQ ID NO 222
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 222
agcgtctctc gatctcattc tcatgagaaa gagcgcgcga acatgacgag agaaacggca    60
cgagttgttt tgatggccc                                                 79

<210> SEQ ID NO 223
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 223
agcgtctctc gatctcattc tcaactacat ctatacactg acaaaacagt ctgacgaaag    60
ccagttgttt tgatggccc                                                 79

<210> SEQ ID NO 224
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 224
agcgtctctc gatctcattc tcaacgtttt gtagtgaatg agggcgagtg gcgcggctaa    60
accgttgttt tgatggccc                                                 79

<210> SEQ ID NO 225
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 225
agcgtctctc gatctcattc tcagaacgag tcgggtgatg cggatagcca ctagcgaaaa    60
```
ctggttgttt tgatggccc                                                    79

<210> SEQ ID NO 226
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 226
agcgtctctc gatctcattc tcaataagac gtacgagatc aggcggaacg cgaaccatag      60
aacgttgttt tgatggccc                                                    79

<210> SEQ ID NO 227
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 227
agcgtctctc gatctcattc tcagttgagt acaaacggaa aatgcgagag atgcgggagt      60
cgagttgttt tgatggccc                                                    79

<210> SEQ ID NO 228
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 228
agcgtctctc gatctcattc tcaattacga gaacagagaa gcgcggattc caccaaagaa      60
agagttgttt tgatggccc                                                    79

<210> SEQ ID NO 229
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 229
agcgtctctc gatctcattc tcaagggaga aggtgatcgg aaaaaaaccc gaagcgacac      60
caagttgttt tgatggccc                                                    79

<210> SEQ ID NO 230
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 230
agcgtctctc gatctcattc tcattaagaa tcgatgagag agcggcgcag aagccaccaa      60
cgggttgttt tgatggccc                                                    79

<210> SEQ ID NO 231
<211> LENGTH: 79
<212> TYPE: DNA
<213> ORGANISM: Artificial Sequence
<220> FEATURE:

<223> OTHER INFORMATION: Synthetic DNA sequence

<400> SEQUENCE: 231

```
agcgtctctc gatctcattc tcatgggaga gagttaagga gaagcgagat agcaaaaacg    60
taggttgttt tgatggccc                                                 79
```

<210> SEQ ID NO 232
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 232

```
agcgtctctc gatctcattc tcaacgaagt tgtaacgaac cgagggatgc gagcaaaaac    60
gttgttgttt tgatggccc                                                 79
```

<210> SEQ ID NO 233
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 233

```
agcgtctctc gatctcattc tcaacgagaa ggagtcggtc ggacgcgaca acacaagcgc    60
gtagttgttt tgatggccc                                                 79
```

<210> SEQ ID NO 234
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 234

```
agcgtctctc gatctcattc tcaatgagtg gatcggtaga agcgaggcta taagtcagaa    60
caggttgttt tgatggccc                                                 79
```

<210> SEQ ID NO 235
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 235

```
agcgtctctc gatctcattc tcaattcttc atccccgcaa aaacaaagaa cgacaagcga    60
aaagttgttt tgatggccc                                                 79
```

<210> SEQ ID NO 236
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 236

```
agcgtctctc gatctcattc tcagtgtcga agagagaagg aggcgaagag agtacgagca    60
caagttgttt tgatggccc                                                 79
```

```
<210> SEQ ID NO 237
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 237
agcgtctctc gatctcattc tcactttact agtaacccca gcaaaagaag atgcgaacaa      60
ggagttgttt tgatggccc                                                  79

<210> SEQ ID NO 238
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 238
agcgtctctc gatctcattc tcacagagag agaaatccga gaggtcgcgg ccagctgcgg      60
agcgttgttt tgatggccc                                                  79

<210> SEQ ID NO 239
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 239
agcgtctctc gatctcattc tcagacatga gatcacagtc aagcggcgcg caaataggaa      60
cttgttgttt tgatggccc                                                  79

<210> SEQ ID NO 240
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 240
agcgtctctc gatctcattc tcacctgcag caagattcag caagcgcagc gagatgaagc      60
gaggttgttt tgatggccc                                                  79

<210> SEQ ID NO 241
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 241
agcgtctctc gatctcattc tcataattta catacactga aaaagcgaa acaagacgta       60 gaggttgttt tgatggccc                                                  79

<210> SEQ ID NO 242
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 242
```
agcgtctctc gatctcattc tcatgagagt agaggaatcg cgccccagag aaagatcgaa    60
gaggttgttt tgatggccc                                                 79

<210> SEQ ID NO 243
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 243
agcgtctctc gatctcattc tcacttgtcg tgcgaagcgc gaaaagggaa gcttaacctt    60
gatgttgttt tgatggccc                                                 79

<210> SEQ ID NO 244
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 244
agcgtctctc gatctcattc tcatcgggtc agagtgatga gaaggtcaag aatcaactcg    60
cgtgttgttt tgatggccc                                                 79

<210> SEQ ID NO 245
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 245
agcgtctctc gatctcattc tcaaccttgt ctattcatga tcaaaataaa aaatgcgaag    60
cgagttgttt tgatggccc                                                 79

<210> SEQ ID NO 246
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 246
agcgtctctc gatctcattc tcagaagaat gaagcggagt agcgagcagc aagagccgtt    60
gcggttgttt tgatggccc                                                 79

<210> SEQ ID NO 247
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 247
agcgtctctc gatctcattc tcatgctata agctgatgag atgagtgcgc gacagaagga    60
aaagttgttt tgatggccc                                                 79

<210> SEQ ID NO 248
<211> LENGTH: 79
<212> TYPE: DNA
<213> ORGANISM: Artificial Sequence

```
<220> FEATURE:
<223> OTHER INFORMATION: Synthetic DNA sequence

<400> SEQUENCE: 248
agcgtctctc gatctcattc tcaaaggagg tcgaaaggac gagcaggcaa tcaaagtaga      60
gctgttgttt tgatggccc                                                   79

<210> SEQ ID NO 249
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 249
agcgtctctc gatctcattc tcaagcgagg tcgagggcag cggtcaaaga tcaaacggtt      60
gaagttgttt tgatggccc                                                   79

<210> SEQ ID NO 250
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 250
agcgtctctc gatctcattc tcagtaatgg gagcgagcag cgagagcatc gaaacgagaa      60
acagttgttt tgatggccc                                                   79

<210> SEQ ID NO 251
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 251
agcgtctctc gatctcattc tcatatgcta gcagaagaga tgagcgcaag acgcgggcga      60
accgttgttt tgatggccc                                                   79

<210> SEQ ID NO 252
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 252
agcgtctctc gatctcattc tcatggacaa tggaaggaga ccggagtagc gcggcggaaa      60
cgtgttgttt tgatggccc                                                   79

<210> SEQ ID NO 253
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 253
agcgtctctc gatctcattc tcacgagaga ggagagctag agaggcggac cgccagcgga      60
aaagttgttt tgatggccc                                                   79
```

<210> SEQ ID NO 254
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 254
agcgtctctc gatctcattc tcagaccgag tgcaagcgac cggcaaaaac aaaatggaac    60
tccgttgttt tgatggccc                                                79

<210> SEQ ID NO 255
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 255
agcgtctctc gatctcattc tcagatgtgg acagagaacg cgaccaaaca aaatcgcgaa    60
agagttgttt tgatggccc                                                79

<210> SEQ ID NO 256
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 256
agcgtctctc gatctcattc tcatccagac tgtgaatggc aaatagagag cgcgggcagt    60
aaggttgttt tgatggccc                                                79

<210> SEQ ID NO 257
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 257
agcgtctctc gatctcattc tcattgacaa ggcgaggaaa cgagacctgg catactcttg    60
cgtgttgttt tgatggccc                                                79

<210> SEQ ID NO 258
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 258
agcgtctctc gatctcattc tcaatttacc tgttactagc aactgaaaca aagaacataa    60
gaagttgttt tgatggccc                                                79

<210> SEQ ID NO 259
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 259

```
agcgtctctc gatctcattc tcactttaat ctagttatcc gaagcagaac agaaatccga    60
caggttgttt tgatggccc                                                 79

<210> SEQ ID NO 260
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 260
agcgtctctc gatctcattc tcaatgagcg aggaggtgta acgcgcagag gaaaaaagac    60
gaagttgttt tgatggccc                                                 79

<210> SEQ ID NO 261
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 261
agcgtctctc gatctcattc tcaattcact tgctccaaaa agcaaaagca atcggtcgac    60
cgagttgttt tgatggccc                                                 79

<210> SEQ ID NO 262
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 262
agcgtctctc gatctcattc tcaatgacag cgaagagcgt ctagaaggaa caaccagaaa    60
gctgttgttt tgatggccc                                                 79

<210> SEQ ID NO 263
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 263
agcgtctctc gatctcattc tcaaactcag atgagaagca gacgagaaca gtgatgccgt    60
agagttgttt tgatggccc                                                 79

<210> SEQ ID NO 264
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 264
agcgtctctc gatctcattc tcaatgagtg ttgaggcgac gagtagcgag aacaaagcca    60
agcgttgttt tgatggccc                                                 79

<210> SEQ ID NO 265
<211> LENGTH: 79
<212> TYPE: DNA
```

```
<213> ORGANISM: Artificial Sequence
<220> FEATURE:
<223> OTHER INFORMATION: Synthetic DNA sequence

<400> SEQUENCE: 265
agcgtctctc gatctcattc tcacttaaat ttacaaaaaa cgaaccagtg atcgaagata     60
gaggttgttt tgatggccc                                                  79

<210> SEQ ID NO 266
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 266
agcgtctctc gatctcattc tcacttctaa tctgaaaaca agccgatgga tgaccaccaa     60
gaggttgttt tgatggccc                                                  79

<210> SEQ ID NO 267
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 267
agcgtctctc gatctcattc tcacgatcgg gaaaagcgcg agccaagcaa tacaagtagt     60
aaggttgttt tgatggccc                                                  79

<210> SEQ ID NO 268
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 268
agcgtctctc gatctcattc tcattgctta attcaaacag atcaaaataa agcacataca     60
gcggttgttt tgatggccc                                                  79

<210> SEQ ID NO 269
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 269
agcgtctctc gatctcattc tcacggcggg agaaaaaatc aagagaagcg cacatcagaa     60
gaagttgttt tgatggccc                                                  79

<210> SEQ ID NO 270
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 270
agcgtctctc gatctcattc tcagcgtcac tgaggagaga tccgacgaag agcagataaa     60
acggttgttt tgatggccc                                                  79
```

<210> SEQ ID NO 271
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 271
agcgtctctc gatctcattc tcataagaga gaggtcgcgg tgataaacaa gccaagaaga    60
gtagttgttt tgatggccc                                                79

<210> SEQ ID NO 272
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 272
agcgtctctc gatctcattc tcattatatt cacaaagaaa acagaaagct gctcgctagg    60
caggttgttt tgatggccc                                                79

<210> SEQ ID NO 273
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 273
agcgtctctc gatctcattc tcattcactg ctccaaaaag cttagaaaac aaagaccgga    60
caggttgttt tgatggccc                                                79

<210> SEQ ID NO 274
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 274
agcgtctctc gatctcattc tcatttcaaa cttatttacg gaaaacgacg gattcgaaaa    60
gctgttgttt tgatggccc                                                79

<210> SEQ ID NO 275
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 275
agcgtctctc gatctcattc tcaaaaggag agaagagcaa gaaggtaacg cgaacgatca    60
taagttgttt tgatggccc                                                79

<210> SEQ ID NO 276
<211> LENGTH: 79
<212> TYPE: DNA
<213> ORGANISM: Artificial Sequence
<220> FEATURE:
<223> OTHER INFORMATION: Synthetic DNA sequence

```
<400> SEQUENCE: 276
agcgtctctc gatctcattc tcaaagaaga agagcggtga ggcaagacgc ggcacgagga      60
aatgttgttt tgatggccc                                                  79

<210> SEQ ID NO 277
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 277
agcgtctctc gatctcattc tcacattatg gtgaggaaag atcgccgcgg cccaatatca      60
aaagttgttt tgatggccc                                                  79

<210> SEQ ID NO 278
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 278
agcgtctctc gatctcattc tcagtgtaaa cgatgagtcg agggtgcgac aagcaagaag      60
agagttgttt tgatggccc                                                  79

<210> SEQ ID NO 279
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 279
agcgtctctc gatctcattc tcatgggaac gtgagtagac tgatgagaga gcgcgggcac      60
tcagttgttt tgatggccc                                                  79

<210> SEQ ID NO 280
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 280
agcgtctctc gatctcattc tcacaatagg tgtgaaagag aaagagcggc gacctagatg      60
actgttgttt tgatggccc                                                  79

<210> SEQ ID NO 281
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 281
agcgtctctc gatctcattc tcacaggata ggagaacacg agatgtggag agaaccaaat      60
caagttgttt tgatggccc                                                  79

<210> SEQ ID NO 282
<211> LENGTH: 79
```

```
<212> TYPE: DNA
<213> ORGANISM: Artificial Sequence
<220> FEATURE:
<223> OTHER INFORMATION: Synthetic DNA sequence

<400> SEQUENCE: 282
agcgtctctc gatctcattc tcagagcgac cgtagccaca aggcaaggga gcctggattt      60
ctcgttgttt tgatggccc                                                   79

<210> SEQ ID NO 283
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 283
agcgtctctc gatctcattc tcataggtga tgggaatgcg gatcgatggt gacgcggcct      60
cgagttgttt tgatggccc                                                   79

<210> SEQ ID NO 284
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 284
agcgtctctc gatctcattc tcatttattc attcaaggaa aaacacaaac agaaaataga      60
gcagttgttt tgatggccc                                                   79

<210> SEQ ID NO 285
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 285
agcgtctctc gatctcattc tcaaaatgga gagagagagc gccatcgtgc gaagcaatac      60
ggagttgttt tgatggccc                                                   79

<210> SEQ ID NO 286
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 286
agcgtctctc gatctcattc tcaacgagaa gccagttcgc gaccaacaaa gagaggcgag      60
aaggttgttt tgatggccc                                                   79

<210> SEQ ID NO 287
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 287
agcgtctctc gatctcattc tcaacttaac ataaatttca gtctaaacaa gatccggaac      60
```
ggggttgttt tgatggccc                                              79

<210> SEQ ID NO 288
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 288
agcgtctctc gatctcattc tcaagaatgc gtagcgagag atcaagcggg atcaaagcct    60
gtcgttgttt tgatggccc                                              79

<210> SEQ ID NO 289
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 289
agcgtctctc gatctcattc tcaagggagg agtgtgatca gaagtcgcgg aacatcagca    60
tcggttgttt tgatggccc                                              79

<210> SEQ ID NO 290
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 290
agcgtctctc gatctcattc tcagagagag accgcgacaa caaagaactt aggaccggaa    60
cgcgttgttt tgatggccc                                              79

<210> SEQ ID NO 291
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 291
agcgtctctc gatctcattc tcagggagga taacgttcga ccgaaaatgc tgcagagacg    60
cgggttgttt tgatggccc                                              79

<210> SEQ ID NO 292
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 292
agcgtctctc gatctcattc tcagtaggac agaaatgagg tcagaagaag cgaggacctg    60
aaagttgttt tgatggccc                                              79

<210> SEQ ID NO 293
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 293
agcgtctctc gatctcattc tcaaaataca gtgaggagag agatttgaat agacgcggaa    60
ccagttgttt tgatggccc                                                 79

<210> SEQ ID NO 294
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 294
agcgtctctc gatctcattc tcaaggttgc agaggcaatg tgagaatggg ccgagatgcg    60
tgggttgttt tgatggccc                                                 79

<210> SEQ ID NO 295
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 295
agcgtctctc gatctcattc tcagggtgga atccttagag aaatcgaaag gagagaccag    60
catgttgttt tgatggccc                                                 79

<210> SEQ ID NO 296
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 296
agcgtctctc gatctcattc tcagtaataa ctgggtttga dacgtggaaa gcgcggtatc    60
aaagttgttt tgatggccc                                                 79

<210> SEQ ID NO 297
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 297
agcgtctctc gatctcattc tcagttaatt attattccaa aaaacgagcg agggacaagc    60
gatgttgttt tgatggccc                                                 79

<210> SEQ ID NO 298
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 298
agcgtctctc gatctcattc tcaacaactg cgatatggtc acaaagtgag acctcagtgt    60
atggttgttt tgatggccc                                                 79

<210> SEQ ID NO 299

```
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 299
agcgtctctc gatctcattc tcaatattgt tttactcgtc caagtcgcat ccgaagaaag      60
cgagttgttt tgatggccc                                                  79

<210> SEQ ID NO 300
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 300
agcgtctctc gatctcattc tcacagagaa cgcgcataga gaagcggccg aacaatgcaa      60
attgttgttt tgatggccc                                                  79

<210> SEQ ID NO 301
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 301
agcgtctctc gatctcattc tcaaattaca tttcattcca gcgaaaaata cagaaaacgt      60
cgagttgttt tgatggccc                                                  79

<210> SEQ ID NO 302
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 302
agcgtctctc gatctcattc tcagtctgtt caatccacaa gagaaacagg atcgcgaagc      60
caggttgttt tgatggccc                                                  79

<210> SEQ ID NO 303
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 303
agcgtctctc gatctcattc tcagttaatt attattccaa aaaacgagcg agggacaagc      60
gatgttgttt tgatggccc                                                  79

<210> SEQ ID NO 304
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 304
agcgtctctc gatctcattc tcatattaca tttccaatcg taacattgaa acaaatcccg      60
```
aaagttgttt tgatggccc                                                        79

<210> SEQ ID NO 305
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 305
agcgtctctc gatctcattc tcaattcact tgctccaaaa agcaaaagca atcggtcgac            60
cgagttgttt tgatggccc                                                        79

<210> SEQ ID NO 306
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 306
agcgtctctc gatctcattc tcatctcgta aacaaaagaa acaaaatgga cgacgaccga            60
caggttgttt tgatggccc                                                        79

<210> SEQ ID NO 307
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 307
agcgtctctc gatctcattc tcacacaaaa ctcgatcttg attattaaca accggaaacc            60
gcagttgttt tgatggccc                                                        79

<210> SEQ ID NO 308
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 308
agcgtctctc gatctcattc tcacgttaag cgaggaaacg aagcgaaact gagatacttg            60
cttgttgttt tgatggccc                                                        79

<210> SEQ ID NO 309
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 309
agcgtctctc gatctcattc tcattgctta attcaaacag atcaaaataa agcacataca            60
gcggttgttt tgatggccc                                                        79

<210> SEQ ID NO 310
<211> LENGTH: 79
<212> TYPE: DNA
<213> ORGANISM: Artificial Sequence
<220> FEATURE:

<223> OTHER INFORMATION: Synthetic DNA sequence

<400> SEQUENCE: 310
agcgtctctc gatctcattc tcataatttt cacctcacaa gataaaaccg aacgaaccaa        60
tgcgttgttt tgatggccc                                                    79

<210> SEQ ID NO 311
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 311
agcgtctctc gatctcattc tcattccttg ttacactgct agaccaatca tgcaaaacga        60
gacgttgttt tgatggccc                                                    79

<210> SEQ ID NO 312
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 312
agcgtctctc gatctcattc tcatttttaa aagggaaccg aagcgaagtg tgaggtgaac        60
cgagttgttt tgatggccc                                                    79

<210> SEQ ID NO 313
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 313
agcgtctctc gatctcattc tcattcactg ctccaaaaag cttagaaaac aaagaccgga        60
caggttgttt tgatggccc                                                    79

<210> SEQ ID NO 314
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 314
agcgtctctc gatctcattc tcactacaca agcgaacgaa agagagcgct gtagccctgc        60
ttagttgttt tgatggccc                                                    79

<210> SEQ ID NO 315
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 315
agcgtctctc gatctcattc tcaacttaac ataaatttca gtctaaacaa gatccggaac        60
ggggttgttt tgatggccc                                                    79

<210> SEQ ID NO 316
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 316
agcgtctctc gatctcattc tcatacattg attctgaaaa caaaaccaaa gccaaacgga    60
tctgttgttt tgatggccc                                                79

<210> SEQ ID NO 317
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 317
agcgtctctc gatctcattc tcaaccttgt ctattcatga tcaaaataaa aaatgcgaag    60
cgagttgttt tgatggccc                                                79

<210> SEQ ID NO 318
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 318
agcgtctctc gatctcattc tcactttcaa tcaaataaaa acaagctcgt tcgctaggta    60
agggttgttt tgatggccc                                                79

<210> SEQ ID NO 319
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 319
agcgtctctc gatctcattc tcagataaga tcgtagttaa ctcgatttta cttgaacaca    60
ccagttgttt tgatggccc                                                79

<210> SEQ ID NO 320
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 320
agcgtctctc gatctcattc tcatcattcc aaatttacta acagaaaaaa agagacggaa    60
tcggttgttt tgatggccc                                                79

<210> SEQ ID NO 321
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 321
agcgtctctc gatctcattc tcatttacat tcttcgatca agacaacaac aacctaaata    60
agagttgttt tgatggccc                                                 79

<210> SEQ ID NO 322
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 322
agcgtctctc gatctcattc tcaaggacaa ggaatgagac cgcagttaat tcatttatca    60
tctgttgttt tgatggccc                                                 79

<210> SEQ ID NO 323
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 323
agcgtctctc gatctcattc tcactcacct taaactttaa cgaattaaaa aacaagaccg    60
gcagttgttt tgatggccc                                                 79

<210> SEQ ID NO 324
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 324
agcgtctctc gatctcattc tcaaagcgag gaacaacaga ccgagcgggt taatttaaga    60
ttagttgttt tgatggccc                                                 79

<210> SEQ ID NO 325
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 325
agcgtctctc gatctcattc tcattaatct actagaagaa aagcaagacg gaacggaagc    60
ttggttgttt tgatggccc                                                 79

<210> SEQ ID NO 326
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 326
agcgtctctc gatctcattc tcaccggtcg aaggttctgg caagaaccga agaacgaaat    60
ctcgttgttt tgatggccc                                                 79

<210> SEQ ID NO 327
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 327
agcgtctctc gatctcattc tcattttcac attctccgcc cagacaaaaa aagaagagac    60
ccagttgttt tgatggccc                                                 79

<210> SEQ ID NO 328
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 328
agcgtctctc gatctcattc tcactcttct tccaaataat aacgagacgg tcaaagacca    60
aacgttgttt tgatggccc                                                 79

<210> SEQ ID NO 329
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 329
agcgtctctc gatctcattc tcaagtcatt taacccggaa acaagacgcg caaatacaag    60
cgagttgttt tgatggccc                                                 79

<210> SEQ ID NO 330
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 330
agcgtctctc gatctcattc tcataaataa ttattcaaca gaaaaataaa atcaaagtac    60
ctcgttgttt tgatggccc                                                 79

<210> SEQ ID NO 331
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 331
agcgtctctc gatctcattc tcaatacata ctataacaag tagaaaacaa gccgagcagg    60
taggttgttt tgatggccc                                                 79

<210> SEQ ID NO 332
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 332
agcgtctctc gatctcattc tcagttactt gttcaacaaa cgagaacaag gcaggaagtt    60
cgagttgttt tgatggccc                                                 79

<210> SEQ ID NO 333
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 333
agcgtctctc gatctcattc tcatagacga acgaaccgaa gggtcagagt caagcttact    60
cgtgttgttt tgatggccc                                                 79

<210> SEQ ID NO 334
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 334
agcgtctctc gatctcattc tcatcatctt ctcggaagca agaacgagga ttgacaaaca    60
agagttgttt tgatggccc                                                 79

<210> SEQ ID NO 335
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 335
agcgtctctc gatctcattc tcactccttt tttattaaac cggagaaaaa atgagcaata    60
cgagttgttt tgatggccc                                                 79

<210> SEQ ID NO 336
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 336
agcgtctctc gatctcattc tcatttactt taacaatatc aaacaaacgc caagccaagg    60
tgagttgttt tgatggccc                                                 79

<210> SEQ ID NO 337
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 337
agcgtctctc gatctcattc tcacatatag cggaactatc cgcctacacg aaacttaata    60
atcgttgttt tgatggccc                                                 79

<210> SEQ ID NO 338
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 338

```
agcgtctctc gatctcattc tcacttcata tcaacaagaa aaacaaatcg aaaaacagcc    60
tgtgttgttt tgatggccc                                                79

<210> SEQ ID NO 339
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 339
agcgtctctc gatctcattc tcacttgtcg tgcgaagcgc gaaaagggaa gcttaacctt    60
gatgttgttt tgatggccc                                                79

<210> SEQ ID NO 340
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 340
agcgtctctc gatctcattc tcagacatga gaactacacc gagaccaacc ctgattcttg    60
cttgttgttt tgatggccc                                                79

<210> SEQ ID NO 341
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 341
agcgtctctc gatctcattc tcaagttcga agaaggcacg acggagaagt tgtttacccc    60
tgtgttgttt tgatggccc                                                79

<210> SEQ ID NO 342
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 342
agcgtctctc gatctcattc tcacattatt aacgagaaaa ataacccaag agtcgactga    60
ctggttgttt tgatggccc                                                79

<210> SEQ ID NO 343
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 343
agcgtctctc gatctcattc tcacttgtta taaaactcaa gactagaaac cgtaaggat    60 cgtgttgttt tgatggccc                                                79

<210> SEQ ID NO 344
<211> LENGTH: 79
<212> TYPE: DNA
```

<213> ORGANISM: Artificial Sequence
<220> FEATURE:
<223> OTHER INFORMATION: Synthetic DNA sequence

<400> SEQUENCE: 344
agcgtctctc gatctcattc tcagaacgga atcgacacat tcacgacgaa gagaatagag    60
gcagttgttt tgatggccc                                                 79

<210> SEQ ID NO 345
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 345
agcgtctctc gatctcattc tcataatcat cttcaaataa caaaacatga aaagtaccg     60 gacgttgttt tgatggccc                                                 79

<210> SEQ ID NO 346
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 346
agcgtctctc gatctcattc tcatgttaat tcaaagaaca aaaccagcga gctttaagcg    60
aacgttgttt tgatggccc                                                 79

<210> SEQ ID NO 347
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 347
agcgtctctc gatctcattc tcatttacca gataatttcc agaaaaacgt cgaccgaggg    60
taagttgttt tgatggccc                                                 79

<210> SEQ ID NO 348
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 348
agcgtctctc gatctcattc tcaccgcgac aattcgaagg gagatcgaat tgagcctctt    60
cttgttgttt tgatggccc                                                 79

<210> SEQ ID NO 349
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 349
agcgtctctc gatctcattc tcattttatt cctgaaagac gacaaagcag gcaaactgac    60
gctgttgttt tgatggccc                                                 79

<210> SEQ ID NO 350
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 350
agcgtctctc gatctcattc tcatggcatg atctctgaag gaaccaaatg ccaactttat    60
cacgttgttt tgatggccc                                                 79

<210> SEQ ID NO 351
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 351
agcgtctctc gatctcattc tcattgcgaa atcaagcgat taacctgcta taccttaact    60
gaagttgttt tgatggccc                                                 79

<210> SEQ ID NO 352
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 352
agcgtctctc gatctcattc tcactcaatc gatcaaaaga aacgagagtg cgaaaatcga    60
gcggttgttt tgatggccc                                                 79

<210> SEQ ID NO 353
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 353
agcgtctctc gatctcattc tcagttatat acaaacacaa ttaaacaagg aataaaaagt    60
cgagttgttt tgatggccc                                                 79

<210> SEQ ID NO 354
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 354
agcgtctctc gatctcattc tcataacatt cattctacaa aaaacacgag gttcgaaagg    60
atcgttgttt tgatggccc                                                 79

<210> SEQ ID NO 355
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 355
agcgtctctc gatctcattc tcatttaatt tcaatcttga agaaacagca gcgcaagcgc    60
tgagttgttt tgatggccc                                                 79

<210> SEQ ID NO 356
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 356
agcgtctctc gatctcattc tcacgttata ccgttgtgtg aggaaaccga aacacaaggg    60
cttgttgttt tgatggccc                                                 79

<210> SEQ ID NO 357
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 357
agcgtctctc gatctcattc tcactcttga acttacaaga aaaaggaac tacaccgctg     60 agagttgttt tgatggccc                                                 79

<210> SEQ ID NO 358
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 358
agcgtctctc gatctcattc tcaaattatg ctccaggccg agattagata agatcaagct    60
cgggttgttt tgatggccc                                                 79

<210> SEQ ID NO 359
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 359
agcgtctctc gatctcattc tcacaaatct ccttgccaac gaaggagatg aaacttcaat    60
ctcgttgttt tgatggccc                                                 79

<210> SEQ ID NO 360
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 360
agcgtctctc gatctcattc tcatgctttc atctaccaat cataacaaag cacaaataat    60
ggcgttgttt tgatggccc                                                 79

<210> SEQ ID NO 361
<211> LENGTH: 79

```
<212> TYPE: DNA
<213> ORGANISM: Artificial Sequence
<220> FEATURE:
<223> OTHER INFORMATION: Synthetic DNA sequence

<400> SEQUENCE: 361
agcgtctctc gatctcattc tcattaaagt tttacaagca aactacgaag cggagagcga    60
aaagttgttt tgatggccc                                                 79

<210> SEQ ID NO 362
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 362
agcgtctctc gatctcattc tcattccatt caacatggaa aaataatacc tgagaccgca    60
ggtgttgttt tgatggccc                                                 79

<210> SEQ ID NO 363
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 363
agcgtctctc gatctcattc tcaacacgtg gttaggagaa ggagactcga ttattcattt    60
ccagttgttt tgatggccc                                                 79

<210> SEQ ID NO 364
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 364
agcgtctctc gatctcattc tcaatattat cctcatcaga aaacagagcg aagaaatcaa    60
gcggttgttt tgatggccc                                                 79

<210> SEQ ID NO 365
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 365
agcgtctctc gatctcattc tcacattata tcaatacgaa aaaagacga aaaagtagt     60 cgtgttgttt tgatggccc                                                 79

<210> SEQ ID NO 366
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 366
agcgtctctc gatctcattc tcactttaat ctagttatcc gaagcagaac agaaatccga    60
```
caggttgttt tgatggccc            79

<210> SEQ ID NO 367
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 367
agcgtctctc gatctcattc tcacctgcag caagattcag caagcgcagc gagatgaagc            60
gaggttgttt tgatggccc            79

<210> SEQ ID NO 368
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 368
agcgtctctc gatctcattc tcaaggagcg agacctagac ataggcggag cgacgcacac            60
ctcgttgttt tgatggccc            79

<210> SEQ ID NO 369
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 369
agcgtctctc gatctcattc tcacccagtt gcaaggggaa ggagcgaagc gacgaaccct            60
cgagttgttt tgatggccc            79

<210> SEQ ID NO 370
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 370
agcgtctctc gatctcattc tcacttaata actgtttcaa agcaagatcg accgaaaggg            60
gatgttgttt tgatggccc            79

<210> SEQ ID NO 371
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 371
agcgtctctc gatctcattc tcaaggatcg tgcggacaaa catccgccga gactcgtatt            60
ctcgttgttt tgatggccc            79

<210> SEQ ID NO 372
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 372
agcgtctctc gatctcattc tcaagattct attcaattca aacagaacaa ggagctgacg    60
cgagttgttt tgatggccc                                                 79

<210> SEQ ID NO 373
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 373
agcgtctctc gatctcattc tcaagttcaa accctgatag aaacccgaaa attttaaccg    60
aacgttgttt tgatggccc                                                 79

<210> SEQ ID NO 374
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 374
agcgtctctc gatctcattc tcaattcaca caaaaaacaa gaccggcgag cacctgagtc    60
gaggttgttt tgatggccc                                                 79

<210> SEQ ID NO 375
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 375
agcgtctctc gatctcattc tcaattcttc atttatataa gaaaaacgaa caaagacgat    60
tcggttgttt tgatggccc                                                 79

<210> SEQ ID NO 376
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 376
agcgtctctc gatctcattc tcatggacga agaagaaaat cgatgaataa gtattccgca    60
gatgttgttt tgatggccc                                                 79

<210> SEQ ID NO 377
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 377
agcgtctctc gatctcattc tcaatctcgt taaccacaaa aaacaaccaa cttataccaa    60
gcagttgttt tgatggccc                                                 79

<210> SEQ ID NO 378

```
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 378
agcgtctctc gatctcattc tcacgaaata tcactctctt agagaaaaaa ctgaaagaag    60
gcagttgttt tgatggccc                                                 79

<210> SEQ ID NO 379
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 379
agcgtctctc gatctcattc tcacttcctc gatcaaaaca gaggagaggc acacaaggat    60
cgtgttgttt tgatggccc                                                 79

<210> SEQ ID NO 380
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 380
agcgtctctc gatctcattc tcagtccgac gtcaagcggc aaatgagacc gttaattcac    60
ctcgttgttt tgatggccc                                                 79

<210> SEQ ID NO 381
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 381
agcgtctctc gatctcattc tcattcatta actcattaaa aaatacaacg caacccgatc    60
gaagttgttt tgatggccc                                                 79

<210> SEQ ID NO 382
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 382
agcgtctctc gatctcattc tcaatttacc tgttactagc aactgaaaca aagaacataa    60
gaagttgttt tgatggccc                                                 79

<210> SEQ ID NO 383
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 383
agcgtctctc gatctcattc tcacacttca acttaactca cagaaaaatg taaaacgacc    60
```
cgagttgttt tgatggccc                                                      79

<210> SEQ ID NO 384
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 384
agcgtctctc gatctcattc tcattagaag aacaagtacg atggtacctg aaggagcagt      60
cgagttgttt tgatggccc                                                      79

<210> SEQ ID NO 385
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 385
agcgtctctc gatctcattc tcacgacacg tcgtgaagga aagatcgatt tattcatgtt      60
cctgttgttt tgatggccc                                                      79

<210> SEQ ID NO 386
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 386
agcgtctctc gatctcattc tcaaagattt tcaactactt cgagcgaaac aaagacggga      60
ggagttgttt tgatggccc                                                      79

<210> SEQ ID NO 387
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 387
agcgtctctc gatctcattc tcagcccgat ggacctaagc agcggactgc cttgtcttat      60
taagttgttt tgatggccc                                                      79

<210> SEQ ID NO 388
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 388
agcgtctctc gatctcattc tcattatatt cacaaagaaa acagaaagct gctcgctagg      60
caggttgttt tgatggccc                                                      79

<210> SEQ ID NO 389
<211> LENGTH: 79
<212> TYPE: DNA
<213> ORGANISM: Artificial Sequence
<220> FEATURE:

<223> OTHER INFORMATION: Synthetic DNA sequence

<400> SEQUENCE: 389
agcgtctctc gatctcattc tcacgcgaac gaacgaagga agtgaagcag agatatatca    60
tctgttgttt tgatggccc                                                79

<210> SEQ ID NO 390
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 390
agcgtctctc gatctcattc tcagacgagc aactcctcta ggagtagcaa gtctgtagct    60
ctcgttgttt tgatggccc                                                79

<210> SEQ ID NO 391
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 391
agcgtctctc gatctcattc tcataattaa ctcaaatcga aaacggccag ggagacctac    60
atggttgttt tgatggccc                                                79

<210> SEQ ID NO 392
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 392
agcgtctctc gatctcattc tcattttact acaaaccaaa acacgcagga acccgcgagg    60
ttagttgttt tgatggccc                                                79

<210> SEQ ID NO 393
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 393
agcgtctctc gatctcattc tcaacttgac tctagtaaag aaggtcgaat ctcggccaat    60
ttggttgttt tgatggccc                                                79

<210> SEQ ID NO 394
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 394
agcgtctctc gatctcattc tcaagttcaa atttcaatcg ccaaaataac aaagccaccc    60
gtcgttgttt tgatggccc                                                79

```
<210> SEQ ID NO 395
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 395
agcgtctctc gatctcattc tcacataatc ttgacaaaac aacgaacagc ggtcggtagc      60
attgttgttt tgatggccc                                                  79

<210> SEQ ID NO 396
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 396
agcgtctctc gatctcattc tcacgggaga aaatcgcaga tcgatacaag gtttcttta      60 ttcgttgttt tgatggccc                                                  79

<210> SEQ ID NO 397
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 397
agcgtctctc gatctcattc tcagcggcaa ttgaatgaaa tgagattgac tgttccgttt      60
ctggttgttt tgatggccc                                                  79

<210> SEQ ID NO 398
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 398
agcgtctctc gatctcattc tcatcaattt tcacaaagca aaacaaggag cacaaccgtt      60
acagttgttt tgatggccc                                                  79

<210> SEQ ID NO 399
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 399
agcgtctctc gatctcattc tcattattat ttacgaaaga aacaacttgg gacgagccca      60
acagttgttt tgatggccc                                                  79

<210> SEQ ID NO 400
<211> LENGTH: 79
<212> TYPE: DNA
<213> ORGANISM: Artificial Sequence
<220> FEATURE:
<223> OTHER INFORMATION: Synthetic DNA sequence

<400> SEQUENCE: 400
```
agcgtctctc gatctcattc tcatttacac acaaaataac gagaaggcag taatggataa    60
cgagttgttt tgatggccc                                                 79

<210> SEQ ID NO 401
<211> LENGTH: 10
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (10)..(10)
<223> OTHER INFORMATION: n is a, c, g, or t

<400> SEQUENCE: 401 aggagataan                                                           10

<210> SEQ ID NO 402
<211> LENGTH: 15
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (7)..(9)
<223> OTHER INFORMATION: n is a, c, g, or t

<400> SEQUENCE: 402
gatcaannna aaagt                                                     15

<210> SEQ ID NO 403
<211> LENGTH: 16
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (7)..(7)
<223> OTHER INFORMATION: n is a, c, g, or t

<400> SEQUENCE: 403
accaaanaaa aggcaa                                                    16

<210> SEQ ID NO 404
<211> LENGTH: 11
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (8)..(9)
<223> OTHER INFORMATION: n is a, c, g, or t

<400> SEQUENCE: 404
aacggaanng a                                                         11

<210> SEQ ID NO 405
<211> LENGTH: 15
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (14)..(14)
<223> OTHER INFORMATION: n is a, c, g, or t

<400> SEQUENCE: 405
gacgaagaga atana                                                      15

<210> SEQ ID NO 406
<211> LENGTH: 20
<212> TYPE: DNA
<213> ORGANISM: Artificial Sequence
<220> FEATURE:
<223> OTHER INFORMATION: Synthetic DNA sequence
<220> FEATURE:
<221> NAME/KEY: misc_feature
<222> LOCATION: (12)..(14)
<223> OTHER INFORMATION: n is a, c, g, or t

<400> SEQUENCE: 406
agcgaaaaat annnaaaacg                                                 20

<210> SEQ ID NO 407
<211> LENGTH: 42
<212> TYPE: DNA
<213> ORGANISM: Artificial Sequence
<220> FEATURE:
<223> OTHER INFORMATION: Synthetic DNA sequence

<400> SEQUENCE: 407
agcgtctctg aaacagaggc ttacaggaga aaatcgtttg at                        42

<210> SEQ ID NO 408
<211> LENGTH: 31
<212> TYPE: DNA
<213> ORGANISM: Artificial Sequence
<220> FEATURE:
<223> OTHER INFORMATION: Synthetic DNA sequence

<400> SEQUENCE: 408
ttacaggaga taagaaagtt gttgtcttga t                                    31

<210> SEQ ID NO 409
<211> LENGTH: 25
<212> TYPE: DNA
<213> ORGANISM: Artificial Sequence
<220> FEATURE:
<223> OTHER INFORMATION: Synthetic DNA sequence

<400> SEQUENCE: 409
agcgtctctc gaaatcagag gctta                                           25

<210> SEQ ID NO 410
<211> LENGTH: 41
<212> TYPE: DNA
<213> ORGANISM: Artificial Sequence
<220> FEATURE:
<223> OTHER INFORMATION: Synthetic DNA sequence

<400> SEQUENCE: 410
caggagataa gtattcgatc aatcgaaaag ttgttgtttt g                         41

<210> SEQ ID NO 411
<211> LENGTH: 24
<212> TYPE: DNA
<213> ORGANISM: Artificial Sequence
<220> FEATURE:
<223> OTHER INFORMATION: Synthetic DNA sequence

<400> SEQUENCE: 411
tacattctca aagagtagaa tgta                                          24

<210> SEQ ID NO 412
<211> LENGTH: 25
<212> TYPE: DNA
<213> ORGANISM: Artificial Sequence
<220> FEATURE:
<223> OTHER INFORMATION: Synthetic DNA sequence

<400> SEQUENCE: 412
agcgtctctc gaaacgagcg ataga                                         25

<210> SEQ ID NO 413
<211> LENGTH: 30
<212> TYPE: DNA
<213> ORGANISM: Artificial Sequence
<220> FEATURE:
<223> OTHER INFORMATION: Synthetic DNA sequence

<400> SEQUENCE: 413
gaacatcaga accgtagttg ttttgatggc                                    30

<210> SEQ ID NO 414
<211> LENGTH: 33
<212> TYPE: DNA
<213> ORGANISM: Artificial Sequence
<220> FEATURE:
<223> OTHER INFORMATION: Synthetic DNA sequence

<400> SEQUENCE: 414
gagcaataaa gacagaaact gtcttgatgg ccc                                33

<210> SEQ ID NO 415
<211> LENGTH: 37
<212> TYPE: DNA
<213> ORGANISM: Artificial Sequence
<220> FEATURE:
<223> OTHER INFORMATION: Synthetic DNA sequence

<400> SEQUENCE: 415
aactctcgat ctcattctca agggagatag agaggaa                            37

<210> SEQ ID NO 416
<211> LENGTH: 23
<212> TYPE: DNA
<213> ORGANISM: Artificial Sequence
<220> FEATURE:
<223> OTHER INFORMATION: Forward primer

<400> SEQUENCE: 416
agcgtctctc gatctcattc tca                                           23

<210> SEQ ID NO 417
<211> LENGTH: 16
<212> TYPE: DNA
<213> ORGANISM: Artificial Sequence
<220> FEATURE:
<223> OTHER INFORMATION: Reverse primer

<400> SEQUENCE: 417
gttgttttga tggccc                                                   16

<210> SEQ ID NO 418
<211> LENGTH: 79
<212> TYPE: DNA
<213> ORGANISM: Artificial Sequence

```
<220> FEATURE:
<223> OTHER INFORMATION: Synthetic DNA sequence
<220> FEATURE:
<221> NAME/KEY: misc_feature
<222> LOCATION: (24)..(63)
<223> OTHER INFORMATION: n is a, c, g, or t

<400> SEQUENCE: 418
agcgtctctc gatctcattc tcannnnnnn nnnnnnnnnn nnnnnnnnnn nnnnnnnnnn    60
nnngttgttt tgatggccc                                                  79
```